(12) United States Patent
Fusaki et al.

(10) Patent No.: US 9,127,256 B2
(45) Date of Patent: Sep. 8, 2015

(54) METHOD FOR PRODUCTION OF REPROGRAMMED CELL USING CHROMOSOMALLY UNINTEGRATED VIRUS VECTOR

(75) Inventors: Noemi Fusaki, Ibaraki (JP); Hiroshi Ban, Ibaraki (JP); Mamoru Hasegawa, Ibaraki (JP); Yoshikazu Yonemitsu, Chiba (JP)

(73) Assignee: DNAVEC CORPORATION, Ibaraki (JP)

(*) Notice: Subject to any disclaimer, the term of this patent is extended or adjusted under 35 U.S.C. 154(b) by 1179 days.

(21) Appl. No.: 13/054,022

(22) PCT Filed: Jul. 16, 2009

(86) PCT No.: PCT/JP2009/062911
§ 371 (c)(1),
(2), (4) Date: Aug. 8, 2011

(87) PCT Pub. No.: WO2010/008054
PCT Pub. Date: Jan. 21, 2010

(65) Prior Publication Data
US 2011/0287538 A1 Nov. 24, 2011

(30) Foreign Application Priority Data

Jul. 16, 2008 (JP) ................................. 2008-185049
Oct. 3, 2008 (JP) ................................. 2008-258883
May 26, 2009 (JP) ................................. 2009-126753

(51) Int. Cl.
*C12N 5/00* (2006.01)
*C12N 5/02* (2006.01)
*C12N 5/074* (2010.01)
*C07K 14/47* (2006.01)

(52) U.S. Cl.
CPC .......... *C12N 5/0696* (2013.01); *C07K 14/4702* (2013.01); *C12N 2501/60* (2013.01); *C12N 2501/602* (2013.01); *C12N 2501/603* (2013.01); *C12N 2501/604* (2013.01); *C12N 2501/606* (2013.01); *C12N 2510/00* (2013.01); *C12N 2760/18622* (2013.01); *C12N 2760/18643* (2013.01); *C12N 2760/18645* (2013.01); *C12N 2760/18662* (2013.01)

(58) Field of Classification Search
None
See application file for complete search history.

(56) References Cited

U.S. PATENT DOCUMENTS

| 7,964,401 | B2 | 6/2011 | Yamanaka | |
|---|---|---|---|---|
| 8,058,065 | B2 * | 11/2011 | Yamanaka et al. | 435/377 |
| 2003/0166252 | A1 | 9/2003 | Kitazato et al. | |
| 2005/0130123 | A1 | 6/2005 | Inoue et al. | |
| 2009/0047263 | A1 | 2/2009 | Yamanaka et al. | |
| 2009/0068742 | A1 | 3/2009 | Yamanaka | |
| 2010/0323428 | A1 | 12/2010 | Yoshizaki et al. | |

FOREIGN PATENT DOCUMENTS

| EP | 1437593 A1 | 7/2004 |
|---|---|---|
| EP | 1970446 A1 | 9/2008 |
| WO | WO 03/025570 A1 | 3/2003 |
| WO | WO 2005/080598 A1 | 9/2005 |
| WO | WO-2006/052646 A2 | 5/2006 |
| WO | WO-2006/066320 A1 | 6/2006 |
| WO | WO-2006/079854 A1 | 8/2006 |
| WO | WO-2006/126574 A1 | 11/2006 |
| WO | WO 2007/069666 A1 | 6/2007 |
| WO | WO 2008/096811 A1 | 8/2008 |
| WO | WO 2008/133206 A1 | 11/2008 |

OTHER PUBLICATIONS

Ren et al. Stem Cells, 24(5): 1338-1347, 2006.*
Djuric and Ellis, 202, Stem Cell Research and Therapy, 2010,1:3.*
Takahashi (2006;Cell. 126:663-676.*
Yu (2009. Science, 324:797-801).*
Buganim (2012,Cell, 150:1209-1222.*
Yu, Sciencexpress, Nov. 20, 2007, pp. 1-8.*
Maherali (2008, Cell Stem Cell, 3:595-605.*
Okita et al., "Generation of mouse induced pluripotent stem cells without viral vectors," Science 322: 949-953 (2008) (published online on Oct. 9, 2008).
Okita et al., "Generation of mouse induced pluripotent stem cells without viral vectors," Science 322: 949-953 (Supporting Online Material; 2008) (published online on Oct. 9, 2008).
Stadtfeld et al., "Induced pluripotent stem cells generated without viral integration," Science 322: 945-949 (2008) (published online on Sep. 25, 2008).
Stadtfeld et al., "Induced pluripotent stem cells generated without viral integration," Science 322: 945-949 (Supporting Online Material; 2008) (published online on Sep. 25, 2008).
U.S. Appl. No. 13/819,235, Hiroshi Ban.
Anzen ni Taisaibo, Reset e, Asahi Shimbun Publishing Co., p. 27 (2008).
Anzen na iPS Saibo' ni Michi, The Yomiuri Shimbum. p. 2 (2008).
Bitzer et al. "Sendai virus vectors as an emerging negative-strand RNA viral vector system," J. Gene. Med. 5(7):543-553 (2003).
Fusaki et al. "Efficient induction of transgene-free human pluripotent stem cells using a vector based on Sendai virus, an RNA virus that does not intergrate into the host genome," Proc. Jpn. Acad. Ser. B. 85(8):348-362 (2009).
Ganka Shinikui iPS Saiboyo Saibo o Juritsu• "Sendai Virus Vector Riyo," Yakuji Nippo Ltd. (2008).
Gan Risk Sake iPS Saibo Kaihatsu, Nihon Keizai Shimbun, p. 13 (2008).

(Continued)

Primary Examiner — Valarie Bertoglio
(74) Attorney, Agent, or Firm — Clark & Elbing LLP

(57) ABSTRACT

An objective of the present invention is to provide vectors for conveniently and efficiently producing ES-like cells in which foreign genes are not integrated into the chromosome. The present inventors discovered methods for producing ES-like cells from somatic cells using chromosomally non-integrating viral vectors. Since no foreign gene is integrated into the chromosome of the produced ES-like cells, they are advantageous in tests and research, and immunological rejection and ethical problems can be avoided in disease treatments.

4 Claims, 15 Drawing Sheets

(56) References Cited

OTHER PUBLICATIONS

Hanna et al. "Treatment of sickle cell anemia mouse model with iPS cells generated from autologous skin," *Science* 318(5858):1920-1923 (2007); e-published Dec. 6, 2007.

Hanna et al. "Direct reprogramming of terminally differentiated mature B lymphocytes to pluripotency," *Cell* 133(2):250-264 (2008).

Iida. "2. Sendai virus vector: vector development and its application to health care technology," *Virus* 57:29-36 (2007); includes English abstract.

Lowry et al. "Generation of human induced pluripotent stem cells from dermal fibroblasts," *Proc. Nat'l. Acad. Sci. U.S.A.* 26(8):2883-2888 (2008).

Nakagawa et al. "Generation of induced pluripotent stem cells without Myc from mouse and human fibroblasts," *Nat. Biotechnol.* 26(1):101-106 (2008); e-published Nov. 30, 2007.

Nakanishi et al. "Jizoku Hatsugengata RNA virus vector no kaihatsu to oyo," *Idenshi Delivery Kenkyukai Dai 8 Kai Symposium Yoshishu* p. 5, I-3 (2008).

Nishimura et al. "Persistant and stable gene expression by cytoplasmic RNA replicon based on noncytopathic variant Sendai virus," *J. Biol. Chem.* 282(37):27383-27391 (2007).

Nishimura et al. "Analysis andmedical application of cytoplasmic persistent expression RNA vector," *Journal of Japanese Biochemical Society*, 4T26-7 (2008).

Park et al. "Reprogramming of human somatic cells to pluripotency with defined factors," *Nature* 451(7175):141-146 (2008); e-published Dec. 23, 2007.

Stadtfeld et al. "Defining molecular cornerstones during fibroblast to iPS cell reprogramming in mouse," *Cell Stem Cell* 2(3):230-240 (2008).

Takahashi et al. "Induction of pluripotent stem cells from human fibroblasts by defined factors," *Cell*. 131(5):861-872 (2007).

Tesar et al. "New cell lines from mouse epiblast share defining features with human embryonic stem cells," *Nature*. 448(7150):196-199 (2007); e-published Jun. 27, 2007.

Yu et al. "Induced pluipotent stem cell lines derived from human somatic cells," *Science*. 318(5858):1917-1920 (2007); e-published Nov. 20, 2007.

International Search Report for PCT/JP2009/062911 (2 pages), mailed Sep. 29, 2009.

Supplementary European Search Report for EP 09 79 7978 (2 pages), completed Mar. 12, 2012.

English Language Translation of International Preliminary Report on Patentability for International Patent Application No. PCT/JP2009/062911, mailed Mar. 17, 2011.

* cited by examiner

A. HUMAN iPS CELL INDUCTION USING Lm (Y1214F)/ΔF/SeV

B. HUMAN iPS CELL INDUCTION USING THOMSON FACTORS (Oct4, Sox2, Nanog, Lin28/TSΔF/SeV)

Oct3/4, Sox2, Klf4, c-Myc (YAMANAKA FACTORS)     Oct3/4, Sox2, Nanog, Lin28 (THOMSON FACTORS)

METHOD FOR PRODUCTION OF REPROGRAMMED CELL USING CHROMOSOMALLY UNINTEGRATED VIRUS VECTOR

CROSS-REFERENCE TO RELATED APPLICATIONS

This application is a U.S. National Stage Application of International Patent Application No. PCT/JP2009/062911, filed Jul. 16, 2009, which claims the benefit of Japanese Patent Application Serial No. JP 2009-126753, filed May 26, 2009, Japanese Patent Application Serial No. JP 2008-258883, filed Oct. 3, 2008, and Japanese Patent Application Serial No. JP 2008-185049, filed Jul. 16, 2008.

TECHNICAL FIELD

The present invention relates to methods for producing reprogrammed cells, cells produced by these methods, compositions used in these methods, and such. In particular, the present invention relates to methods for producing pluripotent stem cells from differentiated somatic cells, and pluripotent stem cells prepared by such methods.

BACKGROUND ART

Embryonic stem cells are stem cells established from the inner cell mass of mammalian blastocysts, and they can be proliferated infinitely while maintaining the ability to differentiate into all types of cells (differentiation pluripotency). This property anticipates stem cell therapy of myocardial infarction, Parkinson's disease patients, or such, which is achieved by transplanting myocardial cells or nerve cells induced and prepared in large quantities from ES cells. Furthermore, uses in basic pathological and pharmacological studies and as a development tool in drug discovery are also anticipated. However, these ES cells have the ethical problem of utilizing and sacrificing human fertilized eggs. There is also the problem of immune rejection where the histocompatibility antigens of limited donor fertilized eggs do not match with the patient. On the other hand, tissue stem cells such as neural stem cells, hematopoietic stem cells, and mesenchymal stem cells are present in every tissue of the living body. Since tissue stem cells do not use fertilized eggs, there are few or no ethical problems, and since cells of the patients themselves can be used, immune rejection reactions can also be avoided. However, properties of tissue stem cells are not necessarily understood, and therefore they are difficult to isolate, and their numbers are also very few. Their proliferative ability and differentiation ability are also much more limited compared to ES cells. If somatic cells such as tissue stem cells and differentiated cells can be converted by some means into cells similar to ES cells having a high proliferative ability and differentiation pluripotency (referred to as ES-like cells), such ES-like cells will be ideal stem cells in clinical applications and such.

Specifically, cells of mammals, particularly somatic cells of patients (tissues of the skin, stomach or lung, blood cells, and such) are collected, and these cells are cultured and then stimulated with nuclear reprogramming factors (factors that induce nuclear reprogramming) to produce ES-like cells (they may also be called "artificial pluripotent stem cells", "induced pluripotent stem cells (iPS cells)", or "embryonic stem cell-like cells"). These produced cells are expected to be applied clinically as stem cells or used in basic research including pharmacological or pathological research (Patent Document 1) just as they are, or after storage in cell banks. Furthermore, experiments to confirm pharmaceutical effects can also be carried out using artificial pluripotent stem cells established from patients.

Examples of nuclear reprogramming factors include the Oct gene, the Klf gene, the Myc gene, the Sox gene, the Nanog gene, the Lin28 gene, the TERT gene, and the SV40 Large T gene (Patent Document 2, Non-Patent Documents 1 to 7).

For example, it is known that the above-mentioned ES-like cells can be produced from the above-mentioned somatic cells using the following four recombinant virus vectors (Non-Patent Document 1 to 7). When the produced ES-like cells described above are used clinically, they may be able to avoid problems of immune rejection and ethical problems.

(1) gamma retroviral vector or lentiviral vector (hereinafter, these vectors will be collectively referred to as "retroviral vectors") containing the Oct3/4 gene
(2) retroviral vector containing the Klf4 gene
(3) retroviral vector containing the c-Myc gene
(4) retroviral vector containing the Sox2 gene The above-mentioned patent documents and non-patent documents are as follows:

PRIOR ART DOCUMENTS

Patent Documents

Patent Document 1: International Publication WO 2005/080598
Patent Document 2: International Publication WO 2007/069666

Non-Patent Documents

Non-Patent Document 1: Cell. 2007 Nov. 30; 131(5):861-872
Non-Patent Document 2: Science. 2007 Dec. 21; 318(5858): 1917-1920
Non-Patent Document 3: Nat Biotechnol. 2008 January; 26(1):101-106
Non-Patent Document 4: Science. 2007 Dec. 21; 318(5858): 1920-1923
Non-Patent Document 5: Nature. 2008 Jan. 10; 451(7175): 141-146
Non-Patent Document 6: PNAS. 2008 Feb. 26; 105(8):2883-2888
Non-Patent Document 7: Cell. 2008 Apr. 18; 133(2):250-264

SUMMARY OF THE INVENTION

Problems to be Solved by the Invention

However, it should be noted that the ES-like cells produced using the above-mentioned retroviral vectors have their chromosomes structurally modified by integration of the vectors into the host chromosomes. They may have unanticipated abnormalities in chromosomal functions, and in particular the cells may become cancerous. The reason is because retroviral vectors are used. When retroviral vectors are used, there is the risk that random integration of the vectors into the chromosomes of the transduced cells might cause inactivation of tumor suppressor genes in the chromosomes or activation of genes involved in cancer formation near the insertion site (Jikken Igaku (Experimental Medicine) Vol. 26, No. 5 (supplement): pp. 35-40, 2008). Furthermore, when they are integrated into other genes or genes that modify the expression of those genes, the cells may change into cells with unexpected properties. In addition, since the so-called noncoding regions of the chromosome are recently considered to have certain chromosomal functions as well, unfavorable consequences brought about due to integration of the retroviral vectors into the noncoding regions must also be considered. Additionally, in the case vectors are inserted into genes involved in the differentiation of the pluripotent stem cells, there is a possibility that treatments or studies using the cells obtained by differentiation of the stem cells cannot be carried out, since differentiation does not occur and cells cannot be obtained. Accordingly, with cell reprogramming by conventional methods, problems of safety remain in treatments that use the obtained ES-like cells. In addition, in drug efficacy and pathological analyses using ES-like cells established from patients, effects caused by inactivation or activation of genes originally functioning in cells as a result of insertion of foreign genes into the chromosome must be considered, and such analyses will become extremely difficult operations. Furthermore, when retroviral vectors are used, the established ES-like cells will have the retroviral vectors inserted into different sites in the chromosome depending on the lot even when production is carried out by the same researcher or by different producers according to the same protocol; therefore, there is also the problem that homogeneity of artificial pluripotent stem cells cannot be guaranteed.

The present invention was accomplished with the objective of fundamentally solving such situations, and provides methods for easily and efficiently producing ES-like cells in which foreign genes are not integrated into the chromosome, i.e. chromosomally non-integrating ES cells. Furthermore, the present invention provides gene transfer compositions that are useful for inducing reprogramming by the above-mentioned methods. The present invention also provides pluripotent stem cells obtained by the methods of the present invention.

Means for Solving the Problems

The present inventors discovered that pluripotent stem cells in which foreign genes are not integrated into the chromosomes can be produced by using vector types with no chromosomal integration.

That is, the present invention relates to methods for producing pluripotent stem cells using chromosomally non-integrating vectors, ES-like cells produced by the methods of the present invention, and such, and more specifically relates to the inventions described in each of the claims. Inventions consisting of any combination of two or more inventions described in claims that cite the same claim are also inventions intended herein. Accordingly, the present invention relates to the following:

[1] A method for introducing a gene into a cell to reprogram the cell, wherein the gene is introduced into the cell using a chromosomally non-integrating viral vector.
[2] The method of [1], wherein the reprogramming is induction of a pluripotent stem cell.
[3] The method of [1] or [2], wherein the chromosomally non-integrating viral vector is an RNA viral vector.
[4] The method of [3], wherein the RNA viral vector is a minus-strand RNA viral vector.
[5] The method of [4], wherein the minus-strand RNA viral vector is a paramyxovirus vector.
[6] The method of [5], wherein the paramyxovirus vector is a Sendai virus vector.
[7] The method of any one of [1] to [6], wherein the gene is selected from the group consisting of:
  (1) the Oct gene;
  (2) the Klf gene;
  (3) the Myc gene;
  (4) the Sox gene;
  (5) the Nanog gene;
  (6) the Lin28 gene;
  (7) the SV40 Large T antigen gene; and
  (8) the TERT gene.
[8] A composition for use in gene introduction for reprogramming a cell, which comprises a chromosomally non-integrating viral vector.
[9] The composition of [8], wherein the reprogramming is induction of a pluripotent stem cell.
[10] The composition of [8] or [9], wherein the chromosomally non-integrating viral vector is an RNA viral vector.
[11] The composition of [10], wherein the RNA viral vector is a minus-strand RNA viral vector.
[12] The composition of [11], wherein the minus-strand RNA viral vector is a paramyxovirus vector.
[13] The composition of [12], wherein the paramyxovirus vector is a Sendai virus vector.
[14] The composition of any one of [8] to [13], wherein the gene is selected from the group consisting of:
  (1) the Oct gene;
  (2) the Klf gene;
  (3) the Myc gene;
  (4) the Sox gene;
  (5) the Nanog gene;
  (6) the Lin28 gene;
  (7) the SV40 Large T antigen gene; and
  (8) the TERT gene.

Moreover, the present invention relates to the following:
[1] A method for producing a reprogrammed cell, which comprises the step of contacting a differentiated cell with at least one chromosomally non-integrating viral vector.
[2] The method of [1], wherein the reprogrammed cell is an artificial pluripotent stem cell.
[3] The method of [1] or [2], wherein the vector is at least one chromosomally non-integrating viral vector that carries at least one gene encoding a nuclear reprogramming factor.
[4] The method of [3], wherein the gene is selected from the group consisting of:
  (1) the Oct gene;
  (2) the Klf gene;
  (3) the Myc gene;
  (4) the Sox gene;
  (5) the Nanog gene;
  (6) the Lin28 gene;
  (7) the SV40 Large T antigen gene; and
  (8) the TERT gene.
[5] The method of any one of [1] to [4], wherein the vectors are used in combination so that at least the three genes, Oct, Klf, and Sox genes, or at least the four genes, Oct, Sox, Nanog, and Lin28 genes, are expressed in a cell endogenously or exogenously.
[6] The method of [5], wherein the vectors are used in combination so that at least the four genes, Oct, Klf, Sox, and Myc genes are expressed in a cell endogenously or exogenously.
[7] The method of any one of [1] to [6], wherein the chromosomally non-integrating viral vector is an RNA viral vector.
[8] The method of [7], wherein the RNA viral vector is a minus-strand RNA viral vector.
[9] The method of [8], wherein the minus-strand RNA viral vector is a paramyxovirus vector.
[10] The method of [9], wherein the paramyxovirus vector is a Sendai virus vector.

[11] A method of producing a differentiated cell, which further comprises the step of differentiating a cell produced by the method of any one of [1] to [10].
[12] A cell produced by the method of any one of [1] to [11].
[13] The cell of [12], wherein the vector is not integrated into the chromosome in the step of reprogramming.
[14] A composition for use in reprogramming of a cell, which comprises a chromosomally non-integrating viral vector as an expression vector.
[15] The composition of [14], wherein the reprogramming is induction of a pluripotent stem cell.
[16] The composition of [14] or [15], wherein the chromosomally non-integrating viral vector is an RNA viral vector.
[17] The composition of [16], wherein the RNA viral vector is a minus-strand RNA viral vector.
[18] The composition of [17], wherein the minus-strand RNA viral vector is a paramyxovirus vector.
[19] The composition of [18], wherein the paramyxovirus vector is a Sendai virus vector.
[20] The composition of any one of [14] to [19], wherein the vector carries at least a reprogramming factor-encoding gene which is selected from the group consisting of:
 (1) the Oct gene;
 (2) the Klf gene;
 (3) the Myc gene;
 (4) the Sox gene;
 (5) the Nanog gene;
 (6) the Lin28 gene;
 (7) the SV40 Large T antigen gene; and
 (8) the TERT gene.
[21] Use of a chromosomally non-integrating viral vector in the production of an agent for reprogramming a differentiated cell.
[22] The use of [21], wherein the reprogramming is induction of a pluripotent stem cell from a differentiated cell.
[23] The use of [21] or [22], wherein the chromosomally non-integrating viral vector is an RNA viral vector.
[24] The use of [23], wherein the RNA viral vector is a minus-strand RNA viral vector.
[25] The use of [24], wherein the minus-strand RNA viral vector is a paramyxovirus vector.
[26] The use of [25], wherein the paramyxovirus vector is a Sendai virus vector.
[27] The use of any one of [21] to [26], wherein the vector carries at least a gene encoding a reprogramming factor which is selected from the group consisting of:
 (1) the Oct gene;
 (2) the Klf gene;
 (3) the Myc gene;
 (4) the Sox gene;
 (5) the Nanog gene;
 (6) the Lin28 gene;
 (7) the SV40 Large T antigen gene; and
 (8) the TERT gene.
Further, the present invention relates to the following:
[1] A chromosomally non-integrating viral vector, which carries a gene selected from the group consisting of:
 (1) the Oct gene;
 (2) the Klf gene;
 (3) the Myc gene;
 (4) the Sox gene;
 (5) the Nanog gene;
 (6) the Lin28 gene;
 (7) the SV40 Large T antigen gene; and
 (8) the TERT gene.

[2] The vector of [1], wherein the chromosomally non-integrating viral vector is an RNA viral vector.
[3] The vector of [2], wherein the RNA viral vector is a minus-strand RNA viral vector.
[4] The vector of [3], wherein the minus-strand RNA viral vector is a paramyxovirus vector.
[5] The vector of [4], wherein the paramyxovirus vector is a Sendai virus vector.

Any components of the inventions described herein and any combination thereof are intended herein. In these inventions, inventions excluding any components described herein, or any combinations thereof are also intended herein. Furthermore, certain specific embodiments described herein regarding the present invention not only disclose these embodiments, but also disclose inventions excluding these embodiments from generic inventions disclosed herein which include these embodiments.

Effects of the Invention

As described above, since cells produced by the methods of this invention do not have foreign genes incorporated into the chromosomes, they are not only advantageous in tests and studies utilizing these cells, but can avoid immune rejection problems or ethical problems in the treatment of diseases. Further, they can also help avoid the risk of genotoxicity-based transformation, unexpected side-effects due to alterations in chromosomal functions, and alterations of cellular properties. Furthermore, pluripotent stem cells can be induced from desired cell types including adult skin cells with significantly higher efficiency (for example, approximately 10 times) using the methods of the present invention, compared to conventional methods using retroviruses. Furthermore, with conventional methods using retroviruses, even if cells are produced by completely identical protocols, the ES-like cells that are established will have the retroviral vectors inserted into different sites in the chromosome; thus, the homogeneity of the artificial pluripotent stem cells cannot be guaranteed. In contrast, with the methods of the present invention, since the vectors are not inserted into the chromosomes, cells that are more genetically homogeneous can be stably produced. Furthermore, retroviruses generally have strong tropism, and for example, with ecotropic retroviral vectors currently used in common reprogramming methods, presence of retrovirus receptors, or their introduction from outside, becomes necessary prior to reprogramming, and establishment of artificial pluripotent stem cells in animal species not expressing them has been difficult. In contrast, the methods of the present invention can be applied to a wide range of animal species (mammals in general). For example, this enables application to biological species in strong demand as disease model animals, such as monkeys and pigs.

MODE FOR CARRYING OUT THE INVENTION

Figure 1:
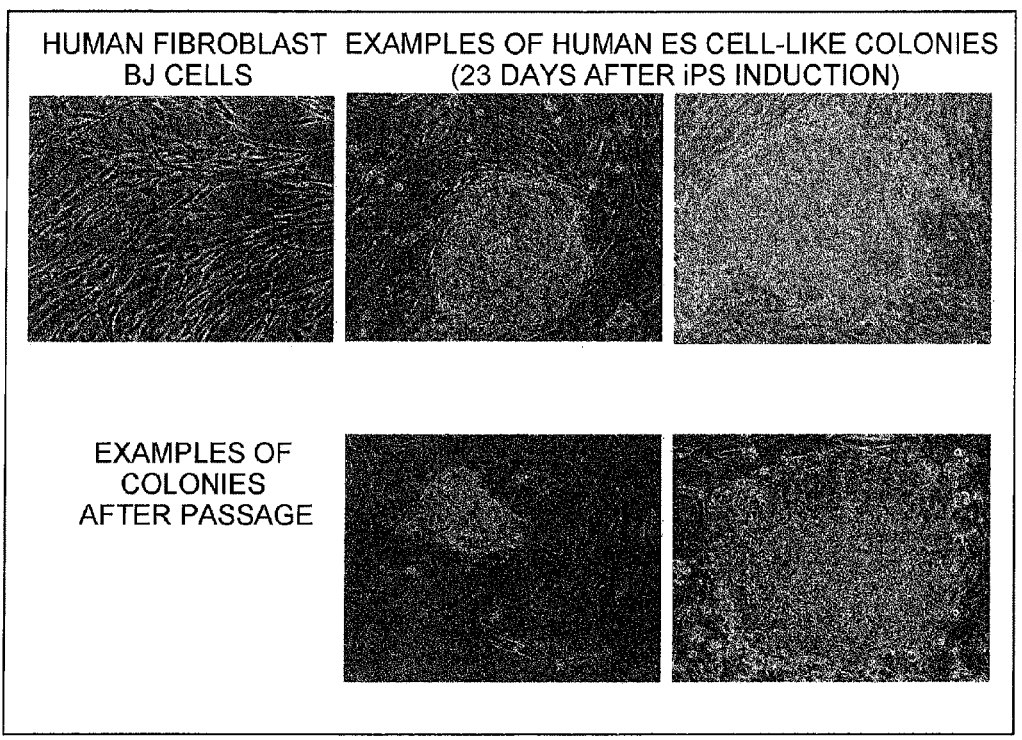
FIG. 1 shows photographs indicating the morphology of cells obtained by the methods according to the present invention. The panels at the center and on the right in the top row show the colonies 23 days after vector introduction. The panels at the bottom row show the passaged colonies.

Hereinafter, the mode for carrying out the present invention will be described in detail.

The present invention provides methods for inducing reprogramming of differentiated cells using a chromosomally non-integrating-type virus vector, in particular, methods for producing pluripotent stem cells from somatic cells. The methods comprise the step of contacting a chromosomally non-integrating virus vector carrying a gene encoding, for example, a nuclear reprogramming factor to be introduced with differentiated cells such as somatic cells. More specifically, the present invention provides methods for introducing genes in the reprogramming of cells, in which the genes are introduced using a chromosomally non-integrating virus vector into cells in need thereof, and compositions containing a chromosomally non-integrating virus vector for that purpose. In the present invention, pluripotent stem cells refer to stem cells produced from the inner cell mass of an embryo of an animal in the blastocyst stage or cells having phenotypes similar to those cells. Specifically, pluripotent stem cells induced in the present invention are cells that express alkaline phosphatase which is an indicator of ES-like cells. Furthermore, preferably, when pluripotent stem cells are cultured, they form flat colonies containing cells with a higher proportion of nucleus than cytoplasm. Culturing can be carried out suitably with a feeder. Moreover, while cultured cells such as MEF stop proliferating in a few weeks, pluripotent stem cells can be passaged for a long period of time, and this can be confirmed based on their proliferative character that is not lost even when they are passaged, for example, 15 times or more, preferably 20 times or more, 25 times or more, 30 times or more, 35 times or more, or 40 times or more every three days. Furthermore, pluripotent stem cells preferably express endogenous Oct3/4 or Nanog, or more preferably, they express both of them. Furthermore, pluripotent stem cells preferably express TERT, and show telomerase activity (activity to synthesize telomeric repeat sequences). Moreover, pluripotent stem cells preferably have the ability to differentiate into three germ layers (the endoderm, mesoderm, and ectoderm) (for example, during teratoma formation and/or embryoid body formation). More preferably, pluripotent stem cells produce germline chimera when they are transplanted into blastocysts. Pluripotent stem cells capable of germline transmission are called germline-competent pluripotent stem cells. Confirmation of these phenotypes can be carried out by known methods (WO 2007/69666; Ichisaka T. et al., Nature 448 (7151):313-7, 2007).

Furthermore, in the present invention, "differentiated" refers to, for example, being more differentiated as compared to pluripotent stem cells, and includes states still possessing the ability to differentiate into multiple cell lineages (for example, somatic stem cells) and terminally differentiated states. Differentiated cells are cells (other than pluripotent stem cells) derived from pluripotent stem cells. Differentiated cells may be, for example, cells that do not have the ability to differentiate into the three germ layers (the endoderm, mesoderm, and ectoderm). Such cells will not have the ability to form the three germ layers unless they are reprogrammed. Furthermore, differentiated cells may be, for example, cells that cannot produce cells that are not of the germ layer type to which they belong. Differentiated cells may be somatic cells, and for example, they may be cells other than germ cells.

In the present invention, reprogramming refers to converting the differentiation state of a particular cell to a less differentiated state, and includes for example, dedifferentiation of differentiated cells, such as inducing cells with differentiation pluripotency, for example pluripotent stem cells, from cells without differentiation pluripotency. Furthermore, in the present invention, dedifferentiation refers to converting a particular cell into a more premature (for example, undifferentiated) state. Dedifferentiation may be reverting a cell to its initial state or intermediate state in its path of differentiation. Furthermore, dedifferentiation may be a change from a cell unable to produce cells that are not of the same germ layer type, into a cell that can differentiate into other germ layer type cells. Dedifferentiation also includes, for example, cells not having triploblastic differentiation ability acquiring this triploblastic differentiation ability. Additionally, dedifferentiation includes the production of pluripotent stem cells.

Furthermore, in the present invention, somatic cells are, for example, cells other than pluripotent stem cells. Somatic cells include, for example, multicellular organism-constituting cells other than pluripotent stem cells, and cultured cells thereof. Somatic cells include for example, somatic stem cells and terminally differentiated cells.

In the present invention, virus vectors are vectors having genomic nucleic acids derived from the virus, and that can express transgenes by integrating the transgenes into the nucleic acids. Furthermore, chromosomally non-integrating virus vectors for producing pluripotent stem cells in the present description are virus vectors derived from viruses and which can introduce genes into target cells, and refer to carriers that do not involve the risk of having the introduced gene integrated into the chromosome (nucleus-derived chromosome) of the host. By constructing chromosomally non-integrating virus vectors such as those that harbor foreign genes, recombinant non-integrating virus vectors used in the present invention can be obtained. Furthermore, in the present invention, virus vectors include infecting virus particles, as well as complexes of the viral core, viral genome, and viral proteins and complexes containing non-infectious viral particles and such, which are complexes having the ability to express loaded genes upon introduction into cells. For example, in RNA viruses, ribonucleoproteins containing a viral genome and viral proteins that bind to it (the viral core portion) can express transgenes in cells when they are introduced into cells (WO00/70055). Introduction into cells can be carried out using appropriate transfection reagents and the like. Such ribonucleoproteins (RNPs) are also included in the virus vectors of the present invention.

In the present invention, "no risk of integration into the host chromosome" indicates that the frequency of integration into the host chromosome, when the viral vector is introduced, is sufficiently low. Preferably, the frequency of integration into a host chromosome is, for example, $5 \times 10^{-4}$ or less, more preferably $10^{-4}$ or less, more preferably $10^{-5}$ or less, more preferably $10^{-6}$ or less, or more preferably $10^{-7}$ or less when infecting human fibrosarcoma-derived cell line HT1080 (ATCC CCL121) at 10 PFU/cell. The non-integrating virus vectors used in the present invention are particularly preferably RNA viruses. In the present invention, RNA viruses refer to viruses having an RNA genome, and not having a DNA phase during their lifecycle. In the present invention, RNA viruses do not carry reverse transcriptases (that is, retroviruses are not included). Thus, in viral proliferation, the viral genome is replicated by RNA-dependent RNA polymerases without the mediation of DNA. Since RNA viruses do not have a DNA phase, the use of RNA virus vectors helps to keep the risk of integration into the host chromosome at a minimum. RNA viruses include single-stranded RNA viruses (including plus strand RNA viruses and minus-strand RNA viruses) and double-stranded RNA viruses. Furthermore, they include viruses with envelope (enveloped viruses) and viruses without envelopes (non-enveloped viruses), but preferably, vectors derived from enveloped viruses are used. In the present invention, RNA viruses specifically include viruses belonging to the following families:

Arenaviridae family such as Lassa virus;
Orthomyxoviridae family such as influenza virus;
Coronaviridae family such as SARS virus;
Togaviridae family such as rubella virus;
Paramyxoviridae family such as mumps virus, measles virus, Sendai virus, and RS virus;
Picornaviridae family such as poliovirus, Coxsackie virus, and echovirus;
Filoviridae family such as Marburg virus and Ebola virus;
Flaviviridae family such as yellow fever virus, dengue fever virus, hepatitis C virus, and hepatitis
G virus;
Bunyaviridae family (including the genera Bunyavirus, Hantavirus, Nairovirus, and Phlebovirus);
Rhabdoviridae family such as rabies virus; and
Reoviridae family.

Examples of chromosomally non-integrating virus vectors used in the present invention include minus-strand RNA virus vectors. Minus-strand RNA virus vectors are vectors consisting of a virus containing a minus strand (an antisense strand of a viral protein-encoding sense strand) RNA as the genome. A minus-strand RNA is also referred to as a negative-strand RNA. The minus-strand RNA viruses presented as examples in the present invention particularly include single-stranded minus-strand RNA viruses (also referred to as non-segmented minus-strand RNA viruses). "Single-stranded negative-strand RNA virus" refers to a virus having a single-stranded negative-strand (i.e., minus-strand) RNA as genome. Such viruses include viruses belonging to families such as Paramyxoviridae (including the genera Paramyxovirus, Morbillivirus, Rubulavirus, and Pneumovirus), Rhabdoviridae (including the genera Vesiculovirus, Lyssavirus, and Ephemerovirus), and Filoviridae, and taxonomically belong to Mononegavirales (Virus vol. 57, no. 1, pp. 29-36, 2007; Annu. Rev. Genet. 32, 123-162, 1998; Fields virology fourth edition, Philadelphia, Lippincott-Raven, 1305-1340, 2001; Microbiol. Immunol. 43, 613-624, 1999; Field Virology, Third edition pp. 1205-1241, 1996).

Minus-strand RNA virus vectors exemplified in the present invention include paramyxovirus vectors. Paramyxovirus vector is a virus vector derived from a Paramyxoviridae family virus. Examples of a Paramyxoviridae virus include Sendai virus. Other examples include Newcastle disease virus, mumps virus, measles virus, respiratory syncytial virus (RS virus), rinderpest virus, distemper virus, simian parainfluenza virus (SV5), and human parainfluenza viruses I, II, and III; influenza virus belonging to the Orthomyxoviridae family; and the vesicular stomatitis virus and Rabies virus belonging to the Rhabdoviridae family.

Further examples of viruses that may be used in the present invention include Sendai virus (SeV), human parainfluenza virus-1 (HPIV-1), human parainfluenza virus-3 (HPIV-3), phocine distemper virus (PDV), canine distemper virus (CDV), dolphin molbillivirus (DMV), peste-des-petits-ruminants virus (PDPR), measles virus (MV), rinderpest virus (RPV), Hendra virus (Hendra), Nipah virus (Nipah), human parainfluenza virus-2 (HPIV-2), simian parainfluenza virus 5 (SV5), human parainfluenza virus-4a (HPIV-4a), human parainfluenza virus-4b (HPIV-4b), mumps virus (Mumps), and Newcastle disease virus (NDV). More preferably, examples include viruses selected from the group consisting of Sendai virus (SeV), human parainfluenza virus-1 (HPIV-1), human parainfluenza virus-3 phocine distemper virus (PDV), canine distemper virus (CDV), dolphin molbillivirus (DMV), peste-des-petits-ruminants virus (PDPR), measles virus (MV), rinderpest virus (RPV), Hendra virus (Hendra), and Nipah virus (Nipah).

Vectors used in the present invention are, for example, viruses belonging to the Paramyxoviridae subfamily (including the genera respirovirus, rubulavirus, and morbillivirus) or derivatives thereof, and examples include viruses belonging to the genus Respirovirus (also referred to as the genus Paramyxovirus) or derivatives thereof. Derivatives include chemically modified viruses and viruses whose viral genes have been modified such that the gene transfer ability of the virus is not impaired. Examples of Respirovirus viruses to which the present invention can be applied include human parainfluenza virus 1 (HPIV-1), human parainfluenza virus 3 (HPIV-3), bovine parainfluenza virus 3 (HPIV-3), Sendai virus (also called mouse parainfluenza virus 1), and simian parainfluenza virus 10 (SPIV-10).

Minus strand RNA viruses exemplified in the present invention more specifically include Sendai viruses. The genome of wild-type Sendai virus includes a short 3' leader region followed by a nucleocapsid (N) gene, a phospho (P) gene, a matrix (M) gene, a fusion (F) gene, a hemagglutinin-neuraminidase (HN) gene, and a large (L) gene, and then a short 5' trailer region, in this order. Production of recombinant vectors corresponding to wild-type viruses, and of various mutant vectors are already known. Furthermore, it has been shown that gene transfer is possible using the RNP alone without its envelope (WO00/70055). Therefore, reprogramming using RNP is also included in the present invention. The same is true with other viral RNPs.

Chromosomally non-integrating viruses in the present invention may be derived from natural strains, wild-type strains, mutant strains, laboratory-passaged strains, artificially constructed strains, and such. That is, these viruses may be virus vectors having similar structures as viruses isolated from nature, or viruses artificially modified by genetic recombination, as long as the desired reprogramming can be induced. For example, they may have mutations or deletions in any of the genes of the wild-type virus. Furthermore, incomplete viruses such as DI particles (J. Virol. 68: 8413-8417, 1994) may also be used. For example, viruses having a mutation or deletion in at least one gene encoding a viral envelope protein or a coat protein can be suitably used. Such virus vectors are, for example, virus vectors that can replicate the genome in infected cells but cannot form infectious virus particles. Since there is no worry of spreading the infection to the surroundings, such replication-defective virus vectors are very safe. For example, minus-strand RNA viruses that do not contain at least one gene encoding an envelope protein such as F, H, HN, or G, or a spike protein, or a combination thereof may be used (WO00/70055 and WO00/70070; Li, H.-O. et al., J. Virol. 74(14) 6564-6569 (2000)). If proteins necessary for genome replication (for example, N, P, and L proteins) are encoded in the genomic RNA, the genome can be amplified in infected cells. To produce detective type of viruses, for example, the defective gene product or a protein that can complement it is externally supplied in the virus-producing cell (WO00/70055 and WO00/70070; Li, H.-O. et al., J. Virol. 74(14) 6564-6569 (2000)). Furthermore, a method of collecting virus vectors as noninfective virus particles (VLP) without completely complementing the defective viral protein is also known (WO00/70070). Furthermore, when virus vectors are collected as RNPs (for example, RNPs containing the N, L, and P proteins and genomic RNA), vectors can be produced without complementing the envelope proteins.

Furthermore, the use of virus vectors carrying a mutant viral protein gene is also preferred. The present invention particularly provides methods of gene transfer in reprogramming and methods for producing reprogrammed cells using RNA virus vectors having mutations and/or deletions in the viral gene. For example, in the envelope protein and coat proteins, many mutations including attenuation mutations and temperature-sensitive mutations are known. RNA viruses having these mutant protein genes can be used favorably in the present invention. In the present invention, vectors with lowered cytotoxicity are desirably used. Cytotoxicity can be measured, for example by quantifying the release of lactic acid dehydrogenase (LDH) from cells. For example, vectors with significantly lowered cytotoxicity compared to the wild type can be used. Regarding the degree of lowering of cytotoxicity, for example, vectors showing a significant decrease of, for example 20% or more, 25% or more, 30% or more, 35% or more, 40% or more, or 50% or more in the LDH release level compared to the wild-type in a culture medium of HeLa (ATCC CCL-2) or simian CV-1 (ATCC CCL 70) infected at MOI 3 and cultured for three days can be used. Furthermore, mutations that decrease cytotoxicity also include temperature-sensitive mutations. Temperature-sensitive mutations refer to mutations which significantly decrease the activity at the viral host's ordinary temperature (for example, 37° C. to 38° C.) when compared to that at a low temperature (for example, 30° C. to 32° C.). Such proteins with temperature-sensitive mutations are useful since the viruses can be produced under permissive temperatures (low temperatures). When infected at 37° C., the virus vectors having useful temperature-sensitive mutations in the present invention show, a growth rate or gene expression level of, for example, ½ or less, preferably ⅓ or less, more preferably ⅕ or less, more preferably ⅒ or less, and more preferably 1/20 or less compared to when cultured cells are infected at 30° C.

A chromosomally non-integrating virus vector used in the present invention may be a wild type as long as it does not inhibit reprogramming and can induce reprogramming by reprogramming factors, and has deletions or mutations in preferably at least one, more preferably at least 2, 3, 4, 5, or more viral genes. Deletions and mutations may be arbitrarily combined and introduced to each of the genes. Herein, a mutation may be a function-impairing mutation or a temperature-sensitive mutation, and is a mutation that decreases the viral proliferation rate or the expression level of the carried gene to preferably ½ or less, more preferably ⅓ or less, more preferably ⅕ or less, more preferably ⅒ or less, and more preferably 1/20 or less compared to the wild type at least at 37° C. The use of such modified virus vectors can be important particularly for the induction of pluripotent stem cells. For example, minus-strand RNA virus vectors used favorably in the present invention have at least two deleted or mutated viral genes. Such viruses include those with deletions of at least two viral genes, those with mutations in at least two viral genes, and those with a mutation in at least one viral gene and a deletion of at least one viral gene. The at least two mutated or deleted viral genes are preferably genes encoding envelope-constituting proteins. For example, vectors with deletion of the F gene with further deletion of the M and/or the HN (or H) gene or further mutation (for example, temperature-sensitive mutation) in the M and/or the HN (or H) gene are used favorably in the present invention. Furthermore, for example, vectors with deletion of the F gene with further deletion of the M or the HN (or H) gene and further mutation in the remaining M and/or the HN (or H) gene (for example, temperature-sensitive mutation) are also used favorably in the present invention. Vectors used in the present invention more preferably have at least three deleted or mutated viral genes (preferably at least three genes encoding envelope-constituting proteins). Such virus vectors include those with deletion of at least three genes, those with mutations in at least three genes, those with mutations in at least one gene and deletion of at least two genes, and those with mutations in at least two genes and deletion of at least one gene. As examples of more preferred embodiments, vectors with deletion of the F gene with further deletion of the M and the HN (or H) gene or further mutations (for example, temperature-sensitive mutations) in the M and the HN (or H) gene are used favorably in the present invention. Furthermore, for example, vectors with deletion of the F gene with further deletion of the M or the HN (or H) gene and further mutation in the remaining M or the HN (or H) gene (for example, temperature-sensitive mutation) are also used favorably in the present invention. Such mutated-form viruses can be produced according to known methods.

For example, a temperature-sensitive mutation of the M gene of the minus-strand RNA virus includes amino acid substitution of a site arbitrarily selected from the group consisting of position 69 (G69), position 116 (T116), and position 183 (A183) of the M protein of a Sendai virus or a homologous site of another minus-strand RNA virus M protein (Inoue, M. et al., J. Virol. 2003, 77: 3238-3246). Amino acids of homologous sites in the M protein of other minus strand RNA viruses can be identified easily, but specifically, the homologous site in an M protein corresponding to G69 in the SeV M protein include G69 for human parainfluenza virus-1 (HPIV-1) (abbreviation is indicated in parenthesis), G73 for human parainfluenza virus-3 (HPIV-3), G70 for phocine distemper virus (PDV) and canine distemper virus (CDV), G71 for dolphin molbillivirus (DMV), G70 for pestedes-petits-ruminants virus (PDPR), measles virus (MV), and rinderpest virus (RPV), G81 for Hendra virus (Hendra) and Nipah virus (Nipah), G70 for human parainfluenza virus-2 (HPIV-2), E47 for human parainfluenza virus-4a (HPIV-4a) and human parainfluenza virus-4b (HPIV-4b), and E72 for mumps virus (Mumps) (the letter and number indicate the amino acid and its position). The homologous sites in each of the M proteins corresponding to T116 of the SeV M protein include T116 for human parainfluenza virus-1 (HPIV-1), T120 for human parainfluenza virus-3 (HPIV-3), T104 for phocine distemper virus (PDV) and canine distemper virus (CDV), T105 for dolphin molbillivirus (DMV), T104 for peste-des-petits-ruminants virus (PDPR), measles virus (MV), and rinderpest virus (RPV), T120 for Hendra virus (Hendra) and Nipah virus (Nipah), T117 for human parainfluenza virus-2 (HPIV-2) and simian parainfluenza virus 5 (SV5), T121 for human parainfluenza virus-4a (HPIV-4a) and human parainfluenza virus-4b (HPIV-4b), T119 for mumps virus (Mumps), and S120 for Newcastle disease virus (NDV). The homologous sites in each of the M proteins corresponding to A183 of the SeV M protein include A183 for human parainfluenza virus-1 (HPIV-1), F187 for human parainfluenza virus-3 (HPIV-3), Y171 for phocine distemper virus (PDV) and canine distemper virus (CDV), Y172 for dolphin molbillivirus (DMV), Y171 for peste-des-petits-ruminants virus (PDPR), measles virus (MV), and rinderpest virus (RPV), Y187 for Hendra virus (Hendra) and Nipah virus (Nipah), Y184 for human parainfluenza virus-2 (HPIV-2), F184 for simian parainfluenza virus 5 (SV5), F188 for human parainfluenza virus-4a (HPIV-4a) and human parainfluenza virus-4b (HPIV-4b), F186 for mumps virus (Mumps), and Y187 for Newcastle disease virus (NDV). Among the viruses mentioned above, viruses having a genome encoding a mutant M protein, in which the amino acids of any one site, preferably a combination of any two sites, or more preferably all three sites of the three sites mentioned above are substituted in the respective M proteins to other amino acids, are used preferably in the present invention.

Preferred amino acid mutations are substitution to other amino acids with a side chain having different chemical properties, and examples are substitution to an amino acid with a BLOSUM62 matrix (Henikoff, S. and Henikoff, J. G (1992) Proc. Natl. Acad. Sci. USA 89: 10915-10919) score of three or less, preferably two or less, more preferably one or less, and even more preferably 0 or less. Specifically, G69, T116, and A183 of the Sendai virus M protein or homologous sites in the M protein of other viruses can be substituted to Glu (E), Ala (A), and Ser (S), respectively. Alternatively mutations homologous to mutations in the M protein of the temperature-sensitive P253-505 measles virus strain (Morikawa, Y. et al., Kitasato Arch. Exp. Med. 1991: 64; 15-30) can also be used. Mutations can be introduced according to known mutation methods, for example, using oligonucleotides and such.

Furthermore, examples of temperature-sensitive mutations in the HN (or H) gene include amino acid substitution of a site arbitrarily selected from the group consisting of position 262 (A262), position 264 (G264), and position 461 (K461) of the HN protein of a Sendai virus or a homologous site in the M protein of other minus-strand RNA viruses (Inoue, M. et al., J. Virol. 2003, 77: 3238-3246). Viruses having a genome encoding a mutant HN protein in which the amino acids of any one of the three sites, preferably a combination of any two sites, or more preferably all three sites are substituted to other amino acids are used preferably in the present invention. As mentioned above, preferred amino acid substitutions are substitution to other amino acids with a side chain having different chemical properties. As a preferred example, A262, G264, and K461 of the Sendai virus HN protein or homologous sites in the HN protein of other viruses can be substituted to Thr (T), Arg (R), and Gly (G), respectively. Furthermore, for example, using the temperature-sensitive vaccine strain Urabe AM9 of the mumps virus as a reference, amino acids of positions 464 and 468 of the HN protein can be mutated (Wright, K. E. et al., Virus Res. 2000: 67; 49-57).

Furthermore, minus-strand RNA viruses may have mutations in the P gene and/or the L gene. Examples of such mutations are specifically, mutation of Glu at position 86 (E86) in the SeV P protein, and substitution of Leu at position 511 (L511) in the SeV P protein to other amino acids, or substitution of homologous sites in the P protein of other minus-strand RNA viruses. As mentioned above, preferred amino acid substitutions are substitutions to other amino acids with a side chain having different chemical properties. Specific examples include substitution of the amino acid at position 86 to Lys, and substitution of the amino acid at position 511 to Phe. Furthermore, examples in the L protein include substitution of Asn at position 1197 (N1197) and/or Lys at position 1795 (K1795) in the SeV L protein to other amino acids, or substitutions of homologous sites in the L protein of other minus-strand RNA viruses, and similarly as above, preferred amino acid substitutions are substitutions to other amino acids with a side chain having different chemical properties. Specific examples are substitution of the amino acid at position 1197 to Ser, and substitution of the amino acid at position 1795 to Glu. Mutations of the P gene and L gene can significantly increase the effects of sustained infectivity, suppression of release of secondary particles, or suppression of cytotoxicity. Further, combination of mutations and/or deletions of envelope protein genes can dramatically increase these effects. Furthermore, examples for the L gene include substitution of Tyr at position 1214 (Y1214) and/or substitution of Met at position 1602 (M1602) of the SeV L protein to other amino acids, or substitution of homologous sites in the L protein of other minus-strand RNA viruses, and similarly as above, preferred amino acid substitutions are substitutions to other amino acids with a side chain having different chemical properties. Specific examples are substitution of the amino acid at position 1214 to Phe, and substitution of the amino acid at position 1602 to Leu. The above-mentioned mutations can be arbitrarily combined.

For example, Sendai virus vectors in which at least G at position 69, T at position 116, and A at position 183 of the SeV M protein, at least A of position 262, G of position 264, and K of position 461 of the SeV HN protein, at least L of position 511 of the SeV P protein, and at least N of position 1197 and K of position 1795 of the SeV L protein are each substituted to other amino acids, and in which the F gene is also deficient or deleted; F-gene-deleted or -deficient vectors having substitution mutations at homologous sites in each of the homologous proteins of other minus-strand RNA viruses and having a deleted or deficient F gene; and F-gene-deleted or -deficient minus-strand RNA virus vectors whose cytotoxicity is similar to or lower than those mentioned above and/or whose temperature sensitivity is similar to or higher than those mentioned above are particularly preferred for the expression of nuclear reprogramming factors in the present invention. Specific examples of the substitutions include G69E, T116A, and A183S substitutions for the M protein, A262T, G264, and K461G substitutions for the HN protein, L511F substitution for the P protein, and N1197S and K1795E substitutions for the L protein. Genes encoding nuclear reprogramming factors can be positioned, for example, at the most upstream position (3' side) of the minus-strand RNA genome (for example, at the 3' side of the N gene). However, regarding the Myc gene, it may be positioned at other positions, for example, at the rear of the minus-strand RNA genome, that is, more towards the 5' side. For example, it may be inserted between the HN gene and the L gene.

Examples of mutations of the L protein include substitutions of an amino acids at sites arbitrarily selected from position 942 (Y942), position 1361 (L1361), and position 1558 (L1558) of the SeV L protein to other amino acids, or substitutions of homologous sites in the L protein of other minus-strand RNA viruses. Similarly as above, preferred amino acid substitutions are substitution to other amino acids with a side chain having different chemical properties. Specific examples include substitution of the amino acid of position 942 to His, substitution of the amino acid of position 1361 to Cys, and substitution of the amino acid of position 1558 to Ile. In particular, the L protein with substitutions at least at positions 942 and 1558 can be used preferably. For example, mutant L proteins in which, in addition to position 1558, position 1361 is also substituted to another amino acid are preferred as well. Furthermore, mutant L proteins in which, in addition to position 942, position 1558 and/or position 1361 are also substituted to other amino acids are favorable as well. Mutant L proteins with mutations to other amino acids at position 1558 and/or position 1361 in addition to position 942 are also preferred. These mutations can increase the temperature sensitivity of the L protein.

Examples of mutations of the P protein include substitutions of amino acids at sites arbitrarily selected from position 433 (D433), position 434 (R434), and position 437 (K437) of the SeV P protein to other amino acids, or substitutions of homologous sites in the P protein of other minus-strand RNA viruses. Similarly as above, preferred amino acid substitutions are substitution to other amino acids with a side chain having different chemical properties. Specific examples include substitution of the amino acid of position 433 to Ala (A), substitution of the amino acid of position 434 to Ala (A), and substitution of the amino acid of position 437 to Ala (A). In particular, P proteins in which all three of these sites are substituted can be used preferably. These mutations can increase the temperature sensitivity of the P protein.

F-gene-deleted or -deficient Sendai virus vectors encoding a mutant P protein in which at least at the three positions of D at position 433, R at position 434, and K at position 437 of the SeV P protein are substituted to other amino acids, and a mutant L protein in which at least the L at position 1558 of the SeV L protein is substituted (preferably a mutant L protein in which at least the L at position 1361 is also substituted to another amino acid); and F-gene-deleted or -deficient vector in which homologous sites in other minus-strand RNA viruses are mutated; and F-gene-deleted or -deficient minus-strand RNA virus vectors whose cytotoxicity is similar to or lower than those mentioned above and/or whose temperature sensitivity is similar to or higher than those mentioned above are used preferably in the present invention. In addition to the above-mentioned mutations, each of the viral proteins may have mutations on other amino acids (for example, on ten or less, five or less, four or less, three or less, two or less, or one amino acid). Since vectors comprising the above-mentioned mutations show a high temperature sensitivity, after completion of reprogramming, the vectors can be removed easily by culturing the cells at a slightly high temperature (for example, 37.5° C. to 39° C., preferably 38° C. to 39° C., or 38.5° C. to 39° C.). Nuclear reprogramming factors can be inserted into appropriate sites of a suitable genome, and for example, they are inserted at the most upstream position (3' side) of the genome (for example, at the 3' side of the NP gene). Regarding the Myc gene, it may be positioned, for example, at the 5' end side from the center of the minus-strand RNA virus genome (at the 5' end side from the gene at the center), for example, it may be inserted at the 5' side or the 3' side of the L gene, and particularly at the 3' side of the L gene (for example between HN and L).

The cytotoxicity of vectors can be measured, for example, by quantifying the release of lactate dehydrogenase (LDH) from cells. Specifically, for example, HeLa (ATCC CCL-2) or simian CV-1 (ATCC CCL70) is infected at MOI 3, and the amount of LDH released into the culture solution after three days of culture is measured. The lower the amount of LDH released, the lower the cytotoxicity. Furthermore, temperature sensitivity can be determined by measuring the speed of viral proliferation or the expression level of the installed gene at the viral host's ordinary temperature (for example, 37° C. to 38° C.). The lower the speed of viral proliferation and/or expression level of the installed gene as compared to those without mutations, the higher the temperature sensitivity is judged to be.

Furthermore, when using an envelope virus, a virus containing a protein in the envelope that is different from the envelope protein originally carried by the virus may be used. For example, by expressing a desired exogenous envelope protein in a virus-producing cell when producing the virus, a virus containing this protein can be produced. Such proteins are not particularly limited, and desired proteins, such as adhesion factors, ligands, and receptors, that confer mammalian cells with an infectious ability are used. Specific examples include the G protein of Vesicular stomatitis virus (VSV) (VSV-G). The VSV-G protein may be derived from any VSV strain, and for example, VSV-G protein derived from the Indiana serotype strain (J. Virology 39: 519-528 (1981)) may be used, but it is not limited thereto. The minus-strand RNA virus given as an example in the present invention can include arbitrary combinations of other virus-derived envelope proteins.

Reconstitution of recombinant RNA viruses carrying nuclear reprogramming factors can be carried out using well-known methods. As specific procedures, typically, the minus-strand RNA viruses cited as an example in the present invention can be produced by the steps of (a) transcribing a cDNA encoding the minus-strand RNA virus genomic RNA (minus strand) or a complementary strand thereof (plus strand) in a cell that expresses viral proteins (N, P, and L) necessary for virus particle formation, and (b) collecting a culture supernatant containing the produced viruses. Viral proteins necessary for particle formation may be expressed from the transcribed viral genomic RNA, or they may be provided in trans from sources other than genomic RNA. For example, they can be provided by introducing expression plasmids encoding the N, P, and L proteins into cells. When viral genes necessary for particle formation are lacking in the genomic RNA, those viral genes are separately expressed in virus-producing cells to complement particle formation. To express the viral proteins or the RNA genome in cells, vectors having a DNA encoding such proteins or genomic RNA linked downstream of a suitable promoter that functions in a host cell is introduced into the host cell. The transcribed genomic RNA is replicated in the presence of viral proteins, and infectious virus particles are formed. When producing a defective type of virus lacking genes such as those of the envelope proteins, the missing protein, other viral proteins that can complement the function of those proteins, or such are expressed in the virus-producing cells.

For example, production of the minus-strand RNA viruses exemplified in the present invention can be carried out by using the following known methods (WO97/16539; WO97/16538; WO00/70055; WO00/70070; WO01/18223; WO03/025570; WO2005/071092; WO2006/137517; WO2007/083644; WO2008/007581; Hasan, M. K. et al., J. Gen. Virol. 78: 2813-2820, 1997; Kato, A. et al., 1997, EMBO J. 16: 578-587 and Yu, D. et al., 1997, Genes Cells 2: 457-466; Durbin, A. P. et al., 1997, Virology 235: 323-332; Whelan, S. P. et al., 1995, Proc. Natl. Acad. Sci. USA 92: 8388-8392; Schnell. M. J. et al., 1994, EMBO J. 13: 4195-4203; Radecke, F. et al., 1995, EMBO J. 14: 5773-5784; Lawson, N. D. et al., Proc. Natl. Acad. Sci. USA 92: 4477-4481; Garcin, D. et al., 1995, EMBO J. 14: 6087-6094; Kato, A. et al., 1996, Genes Cells 1: 569-579; Baron, M. D. and Barrett, T., 1997, J. Virol. 71: 1265-1271; Bridgen, A. and Elliott, R. M., 1996, Proc. Natl. Acad. Sci. USA 93: 15400-15404; Tokusumi, T. et al. Virus Res. 2002: 86; 33-38; and Li, H.-O. et al., J. Virol. 2000: 74; 6564-6569). Minus-strand RNA viruses including parainfluenza, vesicular stomatitis virus, rabies virus, measles virus, rinderpest virus, and Sendai virus can be reconstituted from DNAs by these methods.

Examples of methods for producing plus(+)-strand RNA viruses include the following:

1) Coronavirus

Enjuanes L, Sola I, Alonso S, Escors D, Zuniga S.

Coronavirus reverse genetics and development of vectors for gene expression.

Curr Top Microbiol Immunol. 2005; 287:161-97. Review.

2) Togavirus

Yamanaka R, Zullo S A, Ramsey J, Onodera M, Tanaka R, Blaese M, Xanthopoulos K G Induction of therapeutic antitumor antiangiogenesis by intratumoral injection of genetically engineered endostatin-producing Semliki Forest virus.

Cancer Gene Ther. 2001 October; 8(10):796-802.

Datwyler D A, Eppenberger H M, Koller D, Bailey J E, Magyar J P.

Efficient gene delivery into adult cardiomyocytes by recombinant Sindbis virus.

J Mol Med. 1999 December; 77(12):859-64.

3) Picornavirus

Lee S G, Kim D Y, Hyun B H, Bae Y S.

Novel design architecture for genetic stability of recombinant poliovirus: the manipulation of G/C contents and their distribution patterns increases the genetic stability of inserts in a poliovirus-based RPS-Vax vector system.

J Virol. 2002 February; 76(4):1649-62.

Mueller S, Wimmer E.

Expression of foreign proteins by poliovirus polyprotein fusion: analysis of genetic stability reveals rapid deletions and formation of cardioviruslike open reading frames.

J Virol. 1998 January; 72(1):20-31.

4) Flavivirus

Yun S I, Kim S Y, Rice C M, Lee Y M.

Development and application of a reverse genetics system for Japanese encephalitis virus.

J Virol. 2003 June; 77(11):6450-65.

Arroyo J, Guirakhoo F, Fenner S, Zhang Z X, Monath T P, Chambers T J.

Molecular basis for attenuation of neurovirulence of a yellow fever Virus/Japanese encephalitis virus chimera vaccine (ChimeriVax-JE).

J Virol. 2001 January; 75(2):934-42.

5) Reovirus

Roner M R, Joklik W K.

Reovirus reverse genetics: Incorporation of the CAT gene into the reovirus genome.

Proc Natl Acad Sci USA. 2001 Jul. 3; 98(14):8036-41. Epub 2001 Jun. 26.

Regarding other methods for proliferation of RNA viruses and methods for producing recombinant viruses, see "Uirusu-gaku Jikken-gaku Kakuron (Detailed Virology Experiments) ", second revised edition (National Institute of Infectious Diseases Students Institute edition, Maruzen, 1982).

To the above-mentioned chromosomally non-integrating virus vectors, genes for reprogramming cells can be appropriately installed. The genes to be installed may be desired genes involved in the induction and such of various stem cells such as pluripotent stem cells from differentiated cells. For example, such genes necessary for reprogramming or genes that increase the efficiency of reprogramming can be installed. Thus, the present invention provides uses of the chromosomally non-integrating virus vectors of the present invention for introducing genes in cellular reprogramming, and uses of these vectors for expressing reprogramming factors in cells to induce reprogramming of those cells. Furthermore, the present invention provides agents containing the chromosomally non-integrating virus vectors of the present invention for introducing genes in cellular reprogramming (transfer agents, gene transfer agents) and agents containing these vectors for expressing reprogramming factors in cells. Furthermore, the present invention relates to agents containing the chromosomally non-integrating virus vectors of the present invention for expressing reprogramming factors in cells to induce reprogramming of the cells. Furthermore, when carrying out nuclear reprogramming of cells, the vectors of the present invention are also useful for expressing desired genes in these cells. Non-integrating virus vectors carrying one or more genes encoding a nuclear reprogramming factor can be utilized for cellular reprogramming according to the present invention. The present invention can be used for medical uses and for non-medical uses, and is useful in medical and non-medical embodiments. For example, the present invention can be used for therapeutic, surgical, and/or diagnostic, or non-therapeutic, non-surgical, and/or non-diagnostic purposes.

In the present invention, a nuclear reprogramming factor refers to a gene used, by itself or together with a number of factors, for inducing a differentiated state of a certain cell to change to a more undifferentiated state, or a product thereof, and includes for example, a gene used for inducing dedifferentiation of differentiated cells, or a product thereof. The nuclear reprogramming factors in the present invention include factors essential for nuclear reprogramming and accessorial factors (auxiliary factors) which increase the efficiency of nuclear reprogramming. In the present invention, desired genes to be used for nuclear reprogramming can be installed into a vector. For example, genes to be used for the production of pluripotent stem cells can be installed. Specifically, as the nuclear reprogramming factors for induction of pluripotent stem cells, for example, genes that are expressed in ES cells or early embryo but are not expressed or whose expression is decreased in many differentiated somatic cells (ES cell-specific genes and such) can be used. Such genes are preferably genes that encode transcription factors, nucleoproteins, or such. Methods for identifying nuclear programming factors are already known (WO2005/80598), and in fact, genes identified using this method have been shown to be useful in reprogramming into pluripotent stem cells (WO2007/69666).

Examples of such genes include DPPA5 (developmental pluripotency associated 5, ES cell specific gene 1 (ESG1); accession numbers NM_001025290, NM_025274, XM_236761), F-box protein 15 (Fbx15, NM_152676, NM_015798), Nanog (NM_024865, AB093574), ECAT1 (ES cell associated transcript 1; AB211062, AB211060), ERAS (ES cell expressed Ras; NM_181532, NM_181548), DNMT3L (DNA (cytosine-5-)-methyltransferase 3-like; NM_013369, NM_019448), ECAT8 (AB211063, AB211061), GDF3 (growth differentiation factor 3; NM_020634, NM_008108), SOX15 (SRY (sex determining region Y)-box 15; NM_006942, NM_009235), DPPA4 (developmental pluripotency associated 4; NM_018189, NM_028610), DPPA2 (NM_138815, NM_028615), FTHL17 (ferritin, heavy polypeptide-like 17; NM_031894, NM_031261), SALL4 (sal-like 4; NM_020436, NM_175303), Oct3/4 (also called POU5F1; NM_002701, NM_203289, NM_013633, NM_001009178), Sox2 (NM_003106, NM_011443, XM_574919), Rex-1 (ZFP42 (zinc finger protein 42 homolog); NM_174900, NM_009556), Utf1 (undifferentiated embryonic cell transcription factor 1; NM_003577, NM_009482), TCL1A (T-cell leukemia/lymphoma 1A; NM_021966, NM_009337), DPPA3 (also called Stella, NM_199286, NM_139218, XM_216263), KLF4 (Kruppel-like factor 4; NM_004235, NM_010637), catenin β1 (cadherin-associated protein beta 1; NM_001904, NM_007614; including the S33Y mutant), c-Myc (NM_002467, NM_010849; including the T58A mutant), STAT3 (signal transducer and activator of transcription 3; NM_139276, NM_213659), GRB2 (growth factor receptor-bound protein 2; NM_002086, NM_008163), and other genes which are members of the families to which these genes belong. These genes have been shown to be able to induce pluripotent stem cells upon introduction into cells (WO2007/69666). Therefore, a chromosomally non-integrating virus vector, for example, an RNA virus vector, carrying any one of these genes is useful for use in inducing dedifferentiation of cells in the present invention, and can be used favorably for induction of pluripotent stem cells in particular. These genes may be incorporated one at a time into separate vectors, or a number of genes can be integrated altogether into a single vector. Furthermore, each of the genes may be integrated into a single type of vector, or different types of vectors (including chromosomally integrated virus vectors and/or non-viral vectors) may be used in combination with chromosomally non-integrating virus vectors. In addition, individual virus vectors are packaged separately, and can be used by combining them at the time of use. Alternatively, multiple virus vectors carrying different genes can be combined in advance as a kit, or they may be mixed to produce a composition. Furthermore, one or more non-integrating virus vectors containing any combination (or all) of these genes, and kits or compositions containing these vectors can be used favorably for cellular reprogramming, particularly in the production of pluripotent stem cells. In the case of compositions, the vectors may be appropriately mixed in sterilized water, pH buffers, physiological saline solutions, culture solutions, and such. In these systems, a part of or most of the nuclear reprogramming genes can be substituted with proteins which are their expression products. Thus, the compositions and kits of the present invention may include other vectors (chromosomally integrated virus vectors and/or non-viral vectors) that express reprogramming factors and/or compounds, proteins, or such that induce reprogramming, as long as they include at least one chromosomally non-integrating virus vector. All of the factors necessary for reprogramming may be expressed from chromosomally non-integrating virus vectors, or only a portion of them may be expressed from chromosomally non-integrating virus vectors, and the rest may be provided from other vectors and/or compounds (for example, proteins or low-molecular weight compounds). Furthermore, the methods of the present invention for producing reprogrammed cells are not limited to methods in which all gene transfers are carried out using chromosomally non-integrating virus vectors. More specifically, the methods of the present invention only need to use at least one chromosomally non-integrating virus vector, and includes combined use of other vectors (chromosomally integrated virus vectors and/or non-viral vectors) expressing reprogramming factors and/or compounds that induce reprogramming and such.

The present invention relates to compositions to be used for cellular reprogramming, which include a chromosomally non-integrating virus vector as the expression vector. Furthermore, the present invention relates to use of a chromosomally non-integrating virus vector for use in reprogramming of differentiated cells. For example, the present invention provides use of a chromosomally non-integrating virus vector for introducing genes for cellular reprogramming into cells in need thereof. Furthermore, the present invention relates to methods for introducing genes in cellular reprogramming, which use chromosomally non-integrating virus vectors to introduce genes into cells in need thereof. Furthermore, the present invention also relates to compositions to be used for gene transfer in cellular reprogramming and agents to be used for gene transfer in cellular reprogramming (transfer agents to be used in gene transfer for cellular reprogramming and gene transfer agents for cellular reprogramming), which include a chromosomally non-integrating virus vector. Furthermore, the present invention relates to a use of a chromosomally non-integrating virus vector in the production of pharmaceutical agents for introducing genes for cellular reprogramming into cells in need thereof. The present invention also provides gene transfer agents (gene expression agents or expression vectors) for use in cellular reprogramming, which contain chromosomally non-integrating virus vectors. Furthermore, the present invention provides agents for introducing reprogramming genes (gene expression agents or expression vectors), which contain chromosomally non-integrating virus vectors. The present invention also provides, agents for expressing nuclear reprogramming factors (nuclear reprogramming gene-transfer agents, nuclear reprogramming gene-expression vectors) which contain chromosomally non-integrating virus vectors. Furthermore, the present invention provides pluripotent stem cell-inducing agents and pluripotent stem cell-inducing auxiliary gents, which contain chromosomally non-integrating virus vectors encoding nuclear reprogramming factors. The present invention provides use of chromosomally non-integrating virus vectors for the reprogramming of differentiated cells. The present invention also provides use of chromosomally non-integrating virus vectors in the production of pharmaceutical agents, reagents, and/or pharmaceuticals for the reprogramming of differentiated cells. The present invention also relates to use of chromosomally non-integrating virus vectors in the production of agents for introducing nuclear reprogramming factors into differentiated cells.

Herein, reprogramming may be, for example, induction of pluripotent stem cells from differentiated cells. Vectors are used by integrating genes encoding factors for reprogramming. Examples of genes encoding reprogramming factors include genes encoding any one of the above-mentioned factors or factors exemplified below.

The factors that are introduced may be selected appropriately according to the origin of the cells to be reprogrammed, and they may be derived from humans or other mammals such as mice, rats, rabbits, pigs, or primates such as monkeys. Furthermore, the genetic and protein sequences do not necessarily have to be wild-type sequences, and as long as they can induce reprogramming, they may have any mutations. In fact, examples of producing pluripotent stem cells using mutant genes are known (WO2007/69666). For example, a gene encoding an amino acid sequence with one or a small number of (for example, a few, not more than three, not more than five, not more than ten, not more than 15, not more than 20, or not more than 25) amino acid additions, deletions, substitutions, and/or insertions, and which can induce reprogramming may be used in the present invention. Furthermore, as long as biological activity (ability to induce reprogramming) is maintained, for example, polypeptides with deletions or additions of one to several residues (for example, 2, 3, 4, 5, 6, 10, 15, or 20 residues) of amino acids of the N terminus and/or the C terminus, polypeptides with substitution of one to several residues (for example, 2, 3, 4, 5, 6, 10, 15, or 20 residues) of amino acids, and such may be used. Variants which may be used include for example, fragments, analogs, and derivatives of naturally-derived proteins, and fusion proteins of naturally derived proteins with other polypeptides (for example, those with addition of heterologous signal peptides or antibody fragments). Specifically, polypeptides comprising a sequence with one or more amino acid substitutions, deletions, and/or additions in the wild-type amino acid sequence, and having a biological activity (for example, activity to induce reprogramming) equivalent to that of wild-type proteins are included. When using a fragment of a wild-type protein, normally, the fragment contains a continuous region of 70% or more, preferably 80% or more, 85% or more, more preferably 90% or more, 95% or more, or 98% or more of the wild-type polypeptide (a mature form in the case of a secretory protein).

Variants of amino acid sequences can be prepared, for example, by introducing mutations to the DNAs encoding the natural polypeptide (Walker and Gaastra, eds. Techniques in Molecular Biology (MacMillan Publishing Company, New York, 1983); Kunkel, Proc. Natl. Acad. Sci. USA 82:488-492, 1985; Kunkel et al., Methods Enzymol. 154:367-382, 1987; Sambrook et al., Molecular Cloning: A Laboratory Manual (Cold Spring Harbor Laboratory Press, Plainview, N.Y.), 1989; U.S. Pat. No. 4,873,192). An example of guidance for substituting amino acids without affecting biological activity includes the report by Dayhoff et al. (Dayhoff et al., in Atlas of Protein Sequence and Structure (Natl. Biomed. Res. Found., Washington, D.C.), 1978).

The number of amino acids that are modified is not particularly limited, but for example, it is 30% or less, preferably 25% or less, more preferably 20% or less, more preferably 15% or less, more preferably 10% or less, 5% or less, or 3% or less of all amino acids of the naturally-derived mature polypeptide, and is, for example, 15 amino acids or less, preferably ten amino acids or less, more preferably eight amino acids or less, more preferably five or less, or more preferably three amino acids or less. When substituting amino acids, activities of the protein can be expected to be maintained by substitution to an amino acid with similar side chain properties. Such substitutions are called conservative substitutions in the present invention. Examples of conservative substitutions include substitution and such among amino acids within each of the groups such as basic amino acids (such as lysine, arginine, and histidine), acidic amino acids (for example, aspartic acid and glutamic acid), uncharged polar amino acids (for example, glycine, asparagine, glutamine, serine, threonine, tyrosine, and cysteine), nonpolar amino acids (for example, alanine, valine, leucine, isoleucine, proline, phenylalanine, methionine, and tryptophan), β-branched amino acids (for example, threonine, valine, isoleucine), and aromatic amino acids (for example, tyrosine, phenylalanine, tryptophan, and histidine). Furthermore, examples include substitution among amino acids whose relationship in the BLOSUM62 substitution matrix (S. Henikoff and J. G. Henikoff, Proc. Acad. Natl. Sci. USA 89: 10915-10919, 1992) is positive.

The modified proteins exhibit a high homology to the amino acid sequence of the wild-type protein. High homology refers to amino acid sequences having, for example, 70% or higher, 75% or higher, 80% or higher, 85% or higher, 90% or higher, 93% or higher, 95% or higher, or 96% or higher identity. Amino acid sequence identity can be determined using, for example, the BLASTP program (Altschul, S. F. et al., J. Mol. Biol. 215:403-410, 1990). A search can be carried out using default parameters in the Web page of BLAST at NCBI (National Center for Biotechnology Information) (Altschul S. F. et al., Nature Genet. 3:266-272, 1993; Madden, T. L. et al., Meth. Enzymol. 266:131-141, 1996; Altschul S. F. et al., Nucleic Acids Res. 25:3389-3402, 1997; Zhang J. & Madden T. L., Genome Res. 7:649-656, 1997). Alignment of two sequences can be produced, for example, by the Blast 2 sequences program which compares two sequences (Tatiana A et al., FEMS Microbiol Lett. 174:247-250, 1999) and the identity of the sequences determined. Gaps and mismatches are treated similarly, and for example, a value of identity with respect to the entire amino acid sequence of a naturally-derived cytokine (mature form after secretion) is calculated. Specifically, the proportion of the number of matching amino acids in the total number of amino acids of the wild-type protein (mature form in the case of a secreted protein) is calculated.

Furthermore, genes can be introduced with a silent mutation such that the encoded amino acid sequence is not changed. Particularly, in AT rich genes, by substituting five or more consecutive A or T nucleotides with G or C such that the encoded amino acid sequence is not changed, high expression of genes can be stably obtained.

Examples of modified proteins or proteins used for reprogramming are proteins encoded by nucleic acids that hybridize under stringent conditions with a part or all of the coding region of a gene encoding the wild-type protein and having an activity (activity to induce reprogramming) equivalent to that of the wild-type protein. In hybridization, for example, a probe is prepared either from a nucleic acid comprising a sequence of the coding region of the wild-type protein gene or a complementary sequence thereof or from a nucleic acid which is the object of hybridization, and identification can be carried out by detecting whether or not the probe hybridizes to the other nucleic acid. Stringent hybridization conditions are, for example, conditions of performing hybridization in a solution containing 5×SSC, 7% (WN) SDS, 100 micro-g/mL denatured salmon sperm DNA, 5×Denhardt's solution (1×Denhardt's solution includes 0.2% polyvinyl pyrrolidone, 0.2% bovine serum albumin, and 0.2% Ficoll) at 60° C., preferably 65° C., and more preferably 68° C., and then washing by shaking for two hours in 2×SSC, preferably in 1×SSC, more preferably in 0.5×SSC, and more preferably in 0.1×SSC at the same temperature as hybridization.

Examples of genes particularly preferable for inducing cellular reprogramming include F-box protein 15 (Fbx15, NM_152676, NM_015798), Nanog (NM_024865, AB093574), ERAS (ES cell expressed Ras; NM_181532, NM_181548), DPPA2 (NM_138815, NM_028615), Oct3/4 (also called POU5F1; NM_002701, NM_203289, NM_013633, NM_001009178), Sox2 (NM_003106, NM_011443, XM_574919), TCL1A (T-cell leukemia/lymphoma 1A; NM_021966, NM_009337), KLF4 (Kruppel-like factor 4; NM_004235, NM_010637), catenin β1 (cadherin-associated protein beta 1; NM_001904, NM 007614; including the S33Y mutant), and c-Myc (NM_002467, NM_010849; including the T58A mutant), as well as other genes which are members of the families to which these genes belong. When these genes are introduced, the proportion of colonies showing the morphology of induced pluripotent stem cells has been reported to be higher than when the four types of genes (Oct3/4, Sox2, KLF4, and c-Myc) described next are introduced (WO2007/69666). Therefore, chromosomally non-integrating virus vectors carrying any one of these are useful for use in introducing cellular reprogramming in the present invention, and in particular, they can be used favorably for inducing pluripotent stem cells. Individual virus vectors can be used by combining them at the time of use. Furthermore, they can be combined in advance to form a kit, or they may be mixed to form a composition. Furthermore, one or more chromosomally non-integrating virus vectors containing any combination (or all) of these genes, and kits or compositions containing these vectors are also included in the present invention.

Among them, a combination of genes particularly preferred for induction of pluripotent stem cells is a combination comprising at least four types of genes which are the Sox gene, the KLF gene, the Myc gene, and the Oct gene (Takahashi, K. and Yamanaka S., Cell 126, 663-676, 2006; Lowry W E et al., Proc Natl Acad Sci USA, 105(8):2883-8, 2008; Masaki, H. et al., Stem Cell Res. 1:105-115, 2008; WO2007/69666). Herein, the Sox protein, the KLF protein, the Myc protein, and the Oct protein, and their genes refer to proteins and genes which are members belonging to the Sox family, the KLF family, the Myc family, and the Oct family, respectively. There are reports that by making adjustments so that one or more members from each of these four families are expressed, pluripotent stem cells can be induced from various differentiated cells. For example, regarding the Sox family genes, the use of any of the Sox1, Sox2, Sox3, Sox15, and Sox17 genes has been reported to be able to induce pluripotent stem cells (WO2007/69666). Regarding the KLF family as well, pluripotent stem cells could be induced with KLF4 or KLF2 (WO2007/69666). Regarding the Myc family as well, not only the wild-type c-Myc but the T58A mutant, N-Myc, and L-Myc could also induce pluripotent stem cells (WO2007/69666; Blelloch R. et al., Cell Stem Cell, 1: 245-247, 2007). This way, since genes of the families can be selected in various ways and then used, reprogramming can be induced by appropriately selecting genes from the four families mentioned above.

For example, the amount of expression of wild-type c-Myc from RNA virus vectors such as Sendai virus vectors was found to be low. However, by introducing one or more, preferably two or more, three or more, four or more, or all five mutations selected from among a378g, t1122c, t1125c, a1191g, and a1194g into wild-type cMyc, the gene can be highly expressed with stability from the vector. In the present invention, for example, a modified c-Myc gene indicated in SEQ ID NO: 45 can be used favorably. The position where the gene is inserted in the vector can be can be selected as desired.

For example, the Myc gene may be positioned at the rear (5' side) of the minus-strand RNA genome, that is, at a position that can be located faster from the 5' side than from the 3' side among the multiple protein-encoding sequences positioned on the genome (see the Examples). The Myc gene can be positioned, for example, closest to the 5' side (that is, at the first position from the 5' side), or at the second or third position from the 5' side. The Myc gene can be positioned, for example, at the second position from the 5' side of the genome, or specifically, when the L gene is positioned closest to the 5' side of the genome and the HN gene is positioned next, the Myc gene can be positioned between them. The Myc gene can have substitutions in the continuous A or T nucleotide sequence by introduction of suitable silent mutations such that the encoded amino acid sequence is not changed.

A minus-strand RNA virus vector having the Myc gene positioned at the rear (5' side) of the minus-strand RNA genome can be used in combination with other nuclear reprogramming factor-encoding minus-strand RNA virus vectors. In this case, in the other nuclear reprogramming factor-encoding minus-strand RNA virus vectors, the nuclear reprogramming factors can be positioned at the front (3' side) of the minus-strand RNA genome of the respective vectors, that is, at a position that can be located faster from the 3' side than from the 5' side among the multiple protein-encoding sequences positioned on the genome. For example, they may be positioned closest to the 3' side (that is, at the first position from the 3' side), or at the second or third position from the 3' side. For example, genes encoding nuclear reprogramming factors other than Myc (for example, the Oct gene, Klf gene, and Sox gene) are positioned at first or second, or more preferably at the first position from the 5' side of the genome in the respective minus-strand RNA virus vectors. Specifically, a gene encoding the nuclear reprogramming factor can be positioned at the most 3' end side on the 3' side of the NP gene of the genome.

From the colonies of cells which have completed reprogramming, cells from which the vectors have been removed can be selected appropriately. For example, cells from which the vectors have been naturally removed may be selected. To this end, for example, negative selection can be carried out using antibodies specific to the virus vectors (for example, anti-HN antibodies). Furthermore, when using temperature-sensitive vectors, the vectors can be removed easily by culturing at high temperatures (for example, 37.5° C. to 39° C., preferably 38° C. to 39° C., or 38.5° C. to 39° C.).

Specifically, the KLF family includes Klf1 (NM_006563, NM_010635), Klf2 (NM_016270, NM_008452), Klf4 (NM_004235, NM_010637), and Klf5 (NM_001730, NM_009769); the Myc family includes c-Myc (NM_002467, NM_010849, including the T58A mutant), N-Myc (NM_005378, NM_008709), and L-Myc (NM_005376, NM_005806); the Oct family includes Oct1A (NM_002697, NM_198934), Oct3/4 (NM_002701, NM_203289, NM_013633, NM_001009178), and Oct6 (NM_002699, NM_011141); and the Sox family includes Sox1 (NM_005986, NM_009233), Sox2 (NM_003106, NM_011443, XM_574919), Sox3 (NM_005634, NM_009237), Sox7 (NM_031439, NM_011446), Sox15 (NM_006942, NM_009235), Sox17 (NM_022454, NM_011441), and Sox18 (NM_018419, NM_009236). Chromosomally non-integrating virus vectors carrying any one of these genes are useful for use in inducing dedifferentiation of cells in the present invention, and can be used favorably for induction of pluripotent stem cells in particular.

Myc family genes are not essential for induction of pluripotent stem cells, and pluripotent stem cells can be induced using only the genes of the three families excluding the Myc family genes (Nakagawa M. et al., Nat Biotechnol. 26(1): 101-6, 2008; Wering M. et al., Cell Stem Cell 2(1):10-2, 2008; Example 5). When the Myc gene is not expressed, for example, p53 siRNA and UTF1 can be used to significantly increase the induction efficiency of pluripotent stem cells (Y. Zhao et al., Cell Stem Cell, 3 (5): 475-479, 2008; N. Maherali, and K. Hochedlinger, Cell Stem Cell, 3 (6): 595-605, 2008). Furthermore, induction of pluripotent stem cells has been also reported to be possible using only the genes of the three families excluding the KLF family genes (Park I H et al., Nature, 451(7175):141-6, 2008). In addition, by combined use of the G9a histone methyltransferase inhibitor (BIX-01294; Kubicek, S. et al., Mol. Cell 25, 473-481, 2007), induction of pluripotent stem cells has been reported to be possible from fetal NPC using only three genes, i.e., the Klf gene, the Sox gene, and the Myc gene (Shi Y et al., Cell Stem Cell, 2(6):525-8, 2008). Therefore, one or a number of chromosomally non-integrating virus vectors carrying any of the Sox gene, the KLF gene, and the Oct gene, or any of the Sox gene, the Myc gene, and the Oct gene, or a combination of the Sox gene, the Myc gene, and the Klf gene are specially useful for use in inducing cellular reprogramming in the present invention, and can be used favorably for inducing pluripotent stem cells. Virus vectors that encode the respective genes can be separately prepared individually. They can be used by combining them at the time of use. Any combination or all of them may be combined to form a kit or mixed to form a composition. Furthermore, the present invention relates to one or more chromosomally non-integrating virus vectors comprising any combination (or all) of these genes, and a kit or a composition for reprogramming which comprise these vectors. Furthermore, a portion of the recombinant vectors included in this kit can be substituted with proteins, synthetic compounds, or such having corresponding functions.

When one or several of the above-mentioned genes are, for example, already expressed endogenously in the original differentiated cells, introduction of those genes can be omitted. For example, since neural progenitor cells (NPCs) express endogenous Sox family genes, pluripotent stem cells can be induced by the introduction of only Oct3/4 and Klf4 (Shi Y et al., Cell Stem Cell, 2(6):525-8, 2008). Furthermore, induction of pluripotent stem cells from mouse embryonic fibroblasts (MEF) using three genes, Oct4, Sox2, and Esrrb (estrogen-related receptor beta, NM_004452.2, NP_004443.2, NM_011934.3, NP_036064.2) has been reported to be possible, and it has been suggested that Esrrb is able to complement the function of Klf (Feng, B. et al., Nat Cell Biol. 11(2):197-203, 2009). Furthermore, by combining a histone methyltransferase inhibitor (BIX-01294) and a calcium ion channel agonist (BayK8644), pluripotent stem cells can be induced from embryonic fibroblasts by the introduction of only Oct3/4 and Klf4 (Shi Y et al., Cell Stem Cell, 3(5):568-574, 2008). In experiments using neural stem cells (NSCs) derived from adult mouse brain, the introduction of not only the combination of Oct3/4 and Klf4, but also of only the genes of two factors, Oct3/4 and c-Myc, has been reported to be able to induce pluripotent stem cells (Kim, J. B. et al., Nature, doi: 10.1038/nature07061; Published online 29 Jun. 2008; Nature. 2008, 454(7204):646-50). Furthermore, by adjusting the culturing period, pluripotent stem cells can be induced using Oct4 alone (Jeong Beom Kim et al., Cell, 136(3): 411-419, 2009). As for chromosomally non-integrating virus vectors encoding reprogramming factors, only those necessary can be appropriately used. Furthermore, if endogenous expression of endogenous reprogramming factors is induced by the expression of other genes, by chemical treatment, or such, introduction of a vector expressing such other genes or chemical treatment may be combined with the introduction of only the chromosomally non-integrating virus vectors encoding reprogramming factors that cannot be induced by just the above treatments. In the present invention, combining vectors so that at least the three types of genes of the Oct gene, the Klf gene, and the Sox gene, at least the four types of genes of the Oct gene, the Klf gene, the Sox gene, and the Myc gene, or at least the four types of genes of the Oct gene, the Sox gene, the Nanog gene, and the Lin28 gene are expressed endogenously or exogenously includes, for example, not only states in which certain reprogramming factors are endogenously expressed in a natural state, but also includes cases where, in the case the expression of endogenous reprogramming factors can be induced by introduction of vectors expressing other genes or by chemical treatment, protein treatment, or such, combinations of these treatments are combined with chromosomally non-integrating virus vectors so that just the lacking factors are exogenously expressed.

Furthermore, besides the combinations of the four types or three types mentioned above, combinations which include each of the four types of genes of the Oct gene, the Sox gene, the NANOG gene (NM_024865, AB093574) and the LIN28 gene (NM_024674) are also useful for induction of pluripotent stem cells (Yu J. et al., Science, 318(5858):1917-20, 2007). Combinations produced by further combining the Myc gene and the KLF gene are also favorable (Liao J et at, Cell Res. 18(5):600-3, 2008). Chromosomally non-integrating virus vectors carrying any one of these genes are particularly useful in the present invention for use in the induction of cellular dedifferentiation, and can be used favorably for the induction of pluripotent stem cells. One or more chromosomally non-integrating virus vectors containing any combination (or all) of these genes, and kits or compositions comprising these vectors can also be used favorably in cellular reprogramming, and particularly in the production of pluripotent stem cells. Meanwhile, similarly as described above, when the subject cells already express a portion of these genes, vectors expressing those genes do not have to be introduced. Furthermore, a portion of the recombinant vectors included in this kit may be substituted with proteins, synthetic compounds, and such that have corresponding functions.

Other genes can be further combined to the above-described combination of genes to increase the efficiency of induction of reprogramming. Examples of such genes include TERT (NM_198253, NM_009354) and/or SV40 large T antigen (NC_001669.1, Fiers, W. (05-11-1978) Nature 273: (5658) 113-120) (Park I H. et al., Nature, 451 (7175):141-6, 2008). One or more genes selected from the group consisting of HPV16 E6, HPV 16 E7, and Bmi1 (NM_005180, NM_007552) may also be further combined. Furthermore, one or any combination of genes selected from the group consisting of Fbx15 (Mol Cell Biol. 23(8):2699-708, 2003), Nanog (Cell 113: 631-642, 2003), ERas (Nature 423, 541-545, 2003), DPPA2 (Development 130: 1673-1680, 2003), TCL1A (Development 130: 1673-1680, 2003), and β-Catenin (Nat Med 10(1): 55-63, 2004) may be expressed. In addition, one or more genes selected from the group consisting of ECAT1 (AB211062, AB211060), DPPA5 (NM_001025290, NM_025274, XM_236761), DNMT3L (NM_013369, NM_019448), ECAT8 (AB211063, AB211061), GDF3 (NM_020634, NM_008108), SOX15 (NM_006942, NM_009235), DPPA4 (NM_018189, NM_028610), FTHL17 (NM_031894, NM_031261), SALL4 (NM_020436, NM_175303), Rex-1 (NM_174900, NM_009556), Utf1 (NM_003577, NM_009482), DPPA3 (NM_199286, NM_139218, XM_216263), STAT3 (NM_139276, NM_213659), and GRB2 (NM_002086, NM_008163) may be combined. By additionally expressing these genes, induction of pluripotent stem cells may be promoted (WO2007/69666). When mature B cells are the subjects, for example, the myelocytic transcription factor C/EBPα (CCAAT/enhancer-binding-protein α) (NM_004364) can be ectopically expressed, or expression of the B cell transcription factor Pax5 (paired box 5; NM_016734) can be suppressed to promote reprogramming (Hanna J, Cell. 133(2):250-64, 2008). These factors can also be expressed using the chromosomally non-integrating virus vectors of the present invention. Furthermore, a portion of the recombinant vectors included in this kit can be substituted with proteins, synthetic compounds, and such which have corresponding functions.

Furthermore, besides expressing the above-mentioned factors, for example, by combining the addition of compounds, the efficiency of reprogramming can be increased. For example, bFGF (basic fibroblast growth factor) and/or SCF (stem cell factor) can promote the induction of pluripotent stem cells, and moreover can replace the function of c-Myc in the induction of pluripotent stem cells (WO2007/69666). Furthermore, MAP kinase inhibitors (PD98056) are also useful for establishing pluripotent stem cells that are closer to ES cells, and such (WO2007/69666). Furthermore, DNA methylase (Dnmt) inhibitors and/or histone deacetylase (HDAC) inhibitors are reported to improve the efficiency of induction of pluripotent stem cells (Huangfu D et al., Nat Biotechnol. (Published online: 22 Jun. 2008, doi:10.1038/nbt1418); Nat. Biotechnol. 26, 795-797 (2008)). For example, combined use of HDAC(VPA) enables induction of pluripotent stem cells by introduction of only two genes, Oct4 and Sox2 (Huangfu, D. et al., Nat Biotechnol. 2008 26(11):1269-75). Vectors of the present invention are useful as agents for expressing these genes or a portion of those genes. As Dnmt inhibitors, for example, 5-azacytidine and such are useful, and as HDAC inhibitors, for example, suberoylanilide hydroxamic acid (SAHA), trichostatin A (TSA), valproic acid (VPA) and such are useful. Furthermore, when using 5-azacytidine, combined use of glucocorticoid (dexamethasone) can increase the efficiency.

To reprogram cells, the above-mentioned combinations of vectors and such are introduced into cells. When a number of vectors and/or compounds are combined and introduced, the introduction is preferably carried out simultaneously, and specifically, it is preferable to complete the addition of all vectors encoding the reprogramming factors and/or compounds within 48 hours or less, preferably 36 hours or less, more preferably 24 hours or less, 18 hours or less, twelve hours or less, ten hours or less, eight hours or less, six hours or less, three hours or less, two hours or less, or one hour or less from the addition of the first vector, compound, or such. The dose of the vectors can be prepared appropriately, but infection is carried out preferably at MOI of 0.3 to 100, more preferably at MOI of 0.5 to 50, more preferably at MOI of 1 to 30, more preferably at MOI of 1 to 10, more preferably at MOI of 1 to 5, and more preferably at MOI of approximately 3. The induced pluripotent stem cells form flat colonies very similar to those of ES cells, and express alkaline phosphatase. Furthermore, the induced pluripotent stem cells may express the undifferentiated-cell markers Nanog, Oct4, and/or Sox2, and the like. The induced pluripotent stem cells preferably show TERT expression and/or telomerase activity. The present invention also relates to methods for producing cells that express alkaline phosphatase and preferably further express Nanog and/or TERT which are undifferentiated-cell markers, and to a use of chromosomally non-integrating virus vectors in the production of these cells and in the production of pharmaceutical agents for inducing these cells.

According to the present invention, colonies of pluripotent stem cells can be induced from desired cells including adult skin cells and neonatal foreskin cells, for example at an incidence rate of $0.3 \times 10^{-5}$ or more, $0.5 \times 10^{-5}$ or more, $0.8 \times 10^{-5}$ or more, or $1 \times 10^{-5}$ or more (for example, $1.7 \times 10^{-5}$ to $2.4 \times 10^{-3}$), and preferably at an incidence rate of $1.5 \times 10^{-5}$ or more, $1.7 \times 10^{-5}$ or more, $2.0 \times 10^{-5}$ or more, $2.5 \times 10^{-5}$ or more, $3 \times 10^{-5}$ or more, $4 \times 10^{-5}$ or more, $5 \times 10^{-5}$ or more, $8 \times 10^{-5}$ or more, $1 \times 10^{-4}$ or more, $2 \times 10^{-4}$ or more, $3 \times 10^{-4}$ or more, $5 \times 10^{-4}$ or more, $8 \times 10^{-4}$ or more, $1 \times 10^{-3}$ or more, $1.5 \times 10^{-3}$ or more, $2 \times 10^{-3}$ or more, or $2.3 \times 10^{-3}$ or more.

Differentiated cells which become the object of induction of reprogramming are not particularly limited, and desired somatic cells and such may be used. Production of pluripotent stem cells from somatic cells has been shown to be possible not only from cells derived from fetal mice but also from differentiated cells collected from the tail portion of adult mice, and from liver cells, and gastric mucosal cells, and this suggests that the production is not dependent on the cell type or the state of differentiation (WO2007/069666; Aoi T. et al., Science [Published Online Feb. 14, 2008]; Science. 2008; 321(5889):699-702). Induction of pluripotent stem cells has been confirmed to be possible in humans as well, from various cells such as adult facial skin-derived fibroblasts, adult synoviocytes, neonatal foreskin-derived fibroblasts, adult mesenchymal stem cells, skin cells from the palm of an adult, and embryonic cells (Takahashi K et al. (2007) Cell 131: 861-872; Park I H et al., Nature, 451(7175):141-6, 2008). Furthermore, induction of pluripotent stem cells has been reported similarly from terminally differentiated cells such as pancreatic β cells and B lymphocytes as well (Stadtfeld M et al., Curr Biol. 2008 May 21. [PubMed, PMID: 18501604]; Curr Biol. 2008; 18(12):890-4; Hanna J. et al., Cell. 133(2):250-64, 2008). These findings suggest that induction of pluripotent stem cells do not depend on the cells serving as the origin. Methods of the present invention can be applied in the induction of pluripotent stem cells from these desired somatic cells. Specifically, differentiated cells which are the object of reprogramming include fibroblasts, synoviocytes, mucosal cells of the oral cavity, stomach, or such, liver cells, bone marrow cells, tooth germ cells, and other desired cells. Furthermore, cells may be derived, for example, from cells of embryos, fetuses, newborns, children, adults, or the aged. The origin of the animals is not particularly limited, and includes mammals such as humans and non-human primates (monkeys and such), rodents such as mice and rats, and non-rodents such as bovine, pigs, and goats.

Cells produced by the methods of the present invention are useful for causing differentiation into a variety of tissues and cells, and can be used in desired examinations, research, diagnosis, tests, treatments, and such. For example, induced stem cells are expected to be utilized in stem cell therapy. For example, reprogramming is induced by using somatic cells collected from patients, and then somatic stem cells and other somatic cells that are obtained by induction of differentiation can be transplanted into patients. Methods for inducing cellular differentiation are not particularly limited, and for example, differentiation can be induced by retinoic acid treatment, treatment with a variety of growth factors/cytokines, and treatment with hormones. Furthermore, the obtained cells can be used for detecting effects of the desired pharmaceutical agents and compounds, and this enables screening of pharmaceutical agents and compounds to be carried out.

EXAMPLES

Hereinbelow, the present invention is specifically described with reference to the Examples; however, it is not to be construed as being limited thereto. All documents and other references cited herein are incorporated as part of this description.

<Construction of Sendai Virus Vectors Carrying a Foreign Gene Used in the Present Invention>

The methods for constructing Sendai virus vectors carrying a foreign gene used in the present invention are described below. Unless otherwise specified, foreign genes were introduced using the vectors. Hereinbelow, "SeV18+/TSΔF" refers to an F gene-deficient Sendai virus vector in which the M protein has the G69E, T116A, and A183S mutations; the HN protein has the A262T, G264, and K461G mutations; the P protein has the L511F mutation; and the L protein has the N1197S and K1795E mutations (WO2003/025570). This vector has an insertion site (NotI site) for an introduced gene upstream of the NP gene (on the 3' side of the genome; also referred to as "position 18+").

(1) Construction of cDNA Libraries for Isolation of the c-Myc, Sox2, KLF4, and Oct3/4 Genes Total RNA was extracted from Jurkat cells to isolate the c-Myc, Sox2, KLF4, and Oct3/4 genes. $1.0 \times 10^6$ Jurkat cells (Schneider U et al. (1977) Int J Cancer 19(5):621-6) were collected by centrifugation at 8,000 rpm and room temperature for one minute. 200 μl of a cell lysis buffer (10 mM Tris-HCl (pH 7.5), 150 mM NaCl, 1.5 mM MgCl$_2$, 0.65% NP-40) was added to the cells. After pipetting, the cells were suspended by vortexing. Following centrifugation at 6,000 rpm for three minutes, the supernatant was transferred to another 1.5-ml Eppendorf tube. 200 μl of an extraction buffer was add thereto, and this was sufficiently suspended by vortexing. Then, 400 μl of phenol/chloroform/isoamyl alcohol (25:24:1) was added thereto, and this was sufficiently suspended by vortexing. After centrifugation at 15,000 rpm and 4° C. for five minutes, the supernatant was transferred to another 1.5-ml Eppendorf tube. Then, 400 μl of isopropanol was added thereto, and this was sufficiently suspended by vortexing. This suspension was cooled at −20° C. for 30 minutes. Following centrifugation at 15,000 rpm and 4° C. for 15 minutes, the supernatant was discarded, and 1 ml of 70% ethanol was added to the precipitate. After suspension by vortexing, this was centrifuged at 15,000 rpm and 4° C. for five minutes. The supernatant was discarded, and the precipitate was dried at room temperature. Then, this was dissolved in 100 μl of nuclease-free water to prepare a Jurkat cell total RNA solution.

To isolate the KLF4 gene, total RNA was prepared from 293T/17 cells derived from human embryonic kidney cells (Human embryonic kidney subclone 17; ATCC CRL-11286; Pear, W. S. et al., 1993, Proc. Natl. Acad. Sci. USA 90:8392-8396) by the same method as described above.

To isolate the Oct3/4 gene, total RNA was prepared from NCCIT cells which are human embryonic carcinoma cells (ATCC number CRL-2073; Damjanov I, et al., Lab. Invest. 1993, 68(2): 220-32) by the same method as described above.

Using SuperScript III Reverse Transcriptase (Invitrogen, catalog No. 18080-044), cDNAs were synthesized from the prepared total RNAs. 1 μg of total RNA was mixed with 100 ng of random hexamer and 1 μl of 10 mM dNTP mixture, and the total volume was adjusted to 13 μl with nuclease-free water. After heat treatment at 65° C. for five minutes, the mixture was cooled on ice for one minute. Then, 4 μl of 5× First-Strand Buffer, 1 μl of 0.1 M DTT, 1 μl of RNaseOUT, and 1 μl of Superscript III RT were added thereto. After mixing by pipetting, the mixture was spinned down. Then, this was incubated at 25° C. for five minutes at 50° C. for 60 minutes, and then at 70° C. for 15 minutes. 180 μl of TE (pH8.0) was added thereto, and this was used as a cDNA library.

(2) Isolation of the Human Transcriptional Factor c-Myc, and Construction of a Sendai Virus Vector Plasmid Carrying c-Myc The Jurkat cDNA library was subjected to PCR (94° C. for three minutes, and 40 cycles of [98° C. for 10 seconds, 55° C. for 15 seconds, and 72° C. for two minutes], followed by 72° C. for seven minutes) using PrimeStar™ HS DNA polymerase (Takara Bio, catalog No. R010A) and the following primers:

c-Myc-21F (5'-AACCAGCAGCCTCCCGCGACG-3' (SEQ ID NO: 1)) and c-Myc 1930R (5'-AGGACATTTCTGT-TAGAAGGAATCG-3' (SEQ ID NO: 2)). The PCR product was diluted 100-fold with TE, and a 1-μl aliquot was subjected to PCR using the following primers:

c-Myc-F (5'-GATGCCCCTCAACGTTAGCTTACC-3' (SEQ ID NO: 3)) and c-Myc-R (5'-GTTACGCACAA-GAGTTCCGTAGCTG-3' (SEQ ID NO: 4)). The PCR product was separated by electrophoresis using 1% agarose gel. A band of about 1.3 kbp was excised, and the DNA was purified using a Qiaquick Gel Extraction Kit (QIAGEN, Cat. No. 28706). This was cloned into the SwaI site of pCAGGS-BSX (WO2005/071092). A clone that has the correct sequence was selected by sequencing, and thus pCAGGS-BSX-c-Myc was obtained. Then, PCR was carried out using pCAGGS-BSX-c-Myc as a template, together with the following primers: NotI-c-Myc F (5'-ATTGCGGCCGCATGCCCCTCAACGTTAGCTTCAC-3' (SEQ ID NO: 5)) and NotI-c-Myc R (5'-ATTGCGGCCGCGATGAACTTTCAC-CCTAAGTTTTTCTTACTACGGTTACGCACAAG AGTTCCGTAGCTGTTCAAGTTTGTGTTTC-3' (SEQ ID NO: 6)). The PCR product was purified using a Qiaquick PCR Purification kit (QIAGEN, catalog No. 28106), and then this was digested with NotI at 37° C. for three hours. The digest was purified using a Qiaquick PCR Purification kit (QIAGEN, catalog No. 28106), and this was cloned into the NotI site of a Bluescript plasmid vector. The gene sequence was determined by sequencing. A clone that has the correct sequence was selected, and thus pBS-KS-c-Myc was obtained. pBS-KS-c-Myc was digested with NotI at 37° C. for three hours, and this was separated by electrophoresis using 1% agarose gel. A band of about 1.5 kbp was excised, and the DNA was purified using a Qiaquick Gel Extraction Kit (QIAGEN, catalog No. 28706). The NotI fragment containing the c-Myc gene was cloned into the NotI site of the pSeV18+/TSΔF vector encoding the antigenome of a Sendai virus vector (SeV18+/TSΔF). A clone that has the correct sequence was selected by sequencing, and thus pSeV18+c-Myc/TSΔF was obtained.

(3) Isolation of the Human Transcriptional Factor SOX2 Gene and Construction of a Sendai Virus Vector Plasmid Carrying the SOX2 Gene The Jurkat cDNA library was subjected to PCR (94° C. for three minutes, and 40 cycles of [98° C. for 10 seconds, 55° C. for 15 seconds, and 72° C. for two minutes], followed by 72° C. for seven minutes) using PrimeStar HS DNA polymerase (Takara Bio, catalog No. R010A) and the following primers: SOX2-64F (5'-CAAAGTCCCGGCCGGGC-CGAGGGTCGG-3' (SEQ ID NO: 7)) and SOX2-1404R (5'-CCCTCCAGTTCGCTGTCCGGCC-3' (SEQ ID NO: 8)). The PCR product was diluted 100-fold with TE, and a 1-μl aliquot was subjected to PCR using the following primers: Sox2-F (5'-GATGTACAACATGATGGAGACGGAGC-3' (SEQ ID NO: 9)) and Sox2-R (5'-GTCACATGTGT-GAGAGGGGCAGTG-3' (SEQ ID NO: 10)). The PCR product was separated by electrophoresis using 1% agarose gel. A band of about 0.95 kbp was excised, and the DNA was purified using a Qiaquick Gel Extraction Kit (QIAGEN, Cat. No. 28706). This was cloned into the SwaI site of pCAGGS-BSX. A clone that has the correct sequence was selected by sequencing, and thus pCAGGS-BSX-SOX2 was obtained. Then, PCR was carried out using pCAGGS-BSX-SOX2 as a template, together with the following primers:

Not I Sox-2F (5'-ATTGCGGCCGCATGTACAACAT-GATGGAGACG-3' (SEQ ID NO: 11)) and Not I Sox-2R (5'-ATTGCGGCCGCGATGAACTTTCAC-CCTAAGTTTTTCTTACTACGGTCACATGTGTG AGAGGGGCAGTGTGCCGTTAATGGCCGTG-3' (SEQ ID NO: 12)). The PCR product was purified using a Qiaquick PCR Purification kit (QIAGEN, catalog No. 28106), and then digested with NotI at 37° C. for three hours. The digest was purified using a Qiaquick PCR Purification kit (QIAGEN, catalog No. 28106), and this was cloned into the NotI site of a Bluescript plasmid vector. The gene sequence was determined by sequencing. A clone that has the correct sequence was selected, and thus pBS-KS-Sox2 was obtained. pBS-KS-Sox2 was digested with NotI at 37° C. for three hours, and this was separated by electrophoresis using 1% agarose gel. A band of about 1 kbp was excised, and the DNA was purified using a Qiaquick Gel Extraction Kit (QIAGEN, catalog No. 28706). The NotI fragment containing the Sox2 gene was cloned into the NotI site of the pSeV18+/TSΔF vector. A clone that has the correct sequence was selected by sequencing, and thus pSeV18+Sox2/TSΔF was obtained.

(4) Isolation of the Human Transcriptional Factor KLF4 Gene and Construction of a Sendai Virus Vector Plasmid Carrying the KLF4 Gene The Jurkat cDNA library was subjected to PCR (94° C. for three minutes, and 40 cycles of [98° C. for 10 seconds, 55° C. for 15 seconds, and 72° C. for two minutes], followed by 72° C. for seven minutes) using PrimeStar HS DNA polymerase (Takara Bio, catalog No. R010A) and the following primers: KIF-4-35F (5'-CCACATTAATGAGGCAGCCACCTGGC-3' (SEQ ID NO: 13)) and KIF-4 1772R (5'-GCAGTGTGGGTCATATCCACTGTCTG-3' (SEQ ID NO: 14)). The PCR product was diluted 100-fold with TE, and a 1-μl aliquot was subjected to PCR using the following primers:

KIF4-F (5'-GATGGCTGTCAGCGACGCGCTGCTCCC-3' (SEQ ID NO: 15)) and KIF4-R (5'-GTTAAAAATGCCTCTTCATGTGTAAGGCGAG-3' (SEQ ID NO: 16)). The PCR product was separated by electrophoresis using 1% agarose gel. A band of about 1.4 kbp was excised, and the DNA was purified using a Qiaquick Gel Extraction Kit (QIAGEN, Cat. No. 28706). This was cloned into the SwaI site of pCAGGS-BSX to obtain pCAGGS-BSX-KLF4#19. The result of sequencing showed that pCAGGS-BSX-KLF4#19 has a single silent mutation (c19t). Thus, PCR was carried out using pCAGGS-BSX-KLF4#19 as a template, together with the following primers:

NotI-KIF4-F (5'-ATTGCGGCCGCGACATGGCTGTCAGCGACGCGCTG-3' (SEQ ID NO: 17)) and NotI-KIF4-R (5'-ATTGCGGCCGCGATGAACTTTCACCCTAAGTTTTTCTTACTACGGTTAAAAATGCCTCTTCATGTGTAAGGCGAGGTGGTC-3' (SEQ ID NO: 18)). The PCR product was purified using a Qiaquick PCR Purification kit (QIAGEN, catalog No. 28106), and this was cloned into the SwaI site of pCAGGS-BSX. A clone that has the correct sequence was selected by sequencing, and thus pCAGGS-BSX-KLF4 was obtained. Then, PCR was carried out using pCAGGS-BSX-KLF4 as a template, together with the following primers:

NotI-KIF4-F (5'-ATTGCGGCCGCGACATGGCTGTCAGCGACGCGCTG-3' (SEQ ID NO: 17)) and NotI-KIF4-R (5'-ATTGCGGCCGCGATGAACTTTCACCCTAAGTTTTTCTTACTACGGTTAAAAATGCCTCTTCATGTGTAAGGCGAGGTGGTC-3' (SEQ ID NO: 18)). The PCR product was purified using a Qiaquick PCR Purification kit (QIAGEN, catalog No. 28106), and then this was digested with NotI at 37° C. for three hours. The digest was purified using a Qiaquick PCR Purification kit (QIAGEN catalog No. 28106), and this was cloned into the NotI site of a Bluescript plasmid vector. The gene sequence was determined by sequencing. A clone that has the correct sequence was selected, and thus pBS-KS-KLF4 was obtained. pBS-KS-KLF4 was digested with NotI at 37° C. for three hours, and this was separated by electrophoresis using 1% agarose gel. A band of about 1.5 kbp was excised, and the DNA was purified using a Qiaquick Gel Extraction Kit (QIAGEN, catalog No. 28706). The NotI fragment containing the KLF4 gene was cloned into the NotI site of the pSeV18+/TSΔF vector. A clone that has the correct sequence was selected by sequencing, and thus pSeV18+KLF4/TSΔF was obtained.

(5) Isolation of the Human Transcriptional Factor Oct3/4 Gene and Construction of a Sendai Virus Vector Plasmid Carrying the Oct3/4 Gene Two regions of Oct3/4 were separately amplified by PCR. The NCCIT cDNA library was subjected to PCR (94° C. for three minutes, and 35 cycles of [98° C. for 10 seconds, 55° C. for 15 seconds, and 72° C. for one minute], followed by 72° C. for seven minutes) using PrimeStar HS DNA polymerase (Takara Bio, catalog No. R010A), together with the following primers:

Oct-3-28F (5'-CACCATGCTTGGGGCGCCTTCCTTCC-3' (SEQ ID NO: 19)) and OCT3/4 R301 (5'-CATCGGAGTTGCTCTCCACCCCGAC-3' (SEQ ID NO: 20)), or the following primers:

OCT3/4 F192 (5'-CCCGCCGTATGAGTTCTGTGG-3' (SEQ ID NO: 21)) and NotI-Oct-3/4R-DPN (5'-GCCGCGGCCGCGTTATCAGTTTGAATGCATGGGAGAGCCCAG-3' (SEQ ID NO: 22)).

The two PCR products were purified using a Qiaquick PCR Purification kit (QIAGEN, catalog No. 28106), and eluted with 100 μl of an elution buffer attached to the kit. The eluates were diluted 50-fold with TE. 1 μl each of the PCR products was combined and subjected to PCR (94° C. for three minutes, and 35 cycles of [98° C. for 10 seconds, 55° C. for 15 seconds, and 72° C. for 1.5 minutes], followed by 72° C. for seven minutes) using the following primers:

Not I-Oct-3/4F (5'-GCCGCGGCCGCACCATGGCGGGACACCTGGCTTC-3' (SEQ ID NO: 23)) and Not I-Oct-3/4R-DPN (5'-GCCGCGGCCGCGTTATCAGTTTGAATGCATGGGAGAGCCCAG-3' (SEQ ID NO: 22)).

The PCR product was purified using a Qiaquick PCR Purification kit (QIAGEN, catalog No. 28106) and cloned into the SwaI site of pCAGGS-BSX. A clone that has the correct sequence was selected by sequencing, and thus pCAGGS-BSX-Oct3/4 was obtained. Then, PCR (94° C. for three minutes, and 25 cycles of [98° C. for 10 seconds, 55° C. for 15 seconds, and 72° C. for two minutes], followed by 72° C. for seven minutes) was carried out using pCAGGS-BSX-Oct3/4 as a template, together with the following primers:

Not I-Oct-3/4F (5'-GCCGCGGCCGCACCATGGCGGGACACCTGGCTTC-3' (SEQ ID NO: 23)) and Not 1-Oct-3/4R (5'-GCCGCGGCCGCGATGAACTTTCACCCTAAGTTTTTCTTACTACGGTCAGTTTGAATGCATGGGAGAGCCCAGAGTGGTGAC-3' (SEQ ID NO: 24)). The PCR product was purified using a Qiaquick PCR Purification kit (QIAGEN, catalog No. 28106), and then this was digested with NotI at 37° C. for two hours. The digest was purified using a Qiaquick PCR Purification kit (QIAGEN, catalog No. 28106). The NotI fragment containing the Oct3/4 gene was cloned into the NotI site of the pSeV18+/TSΔF vector. A clone that has the correct sequence was selected by sequencing, and thus pSeV18+Oct3/4/TSΔF was obtained.

(6) Construction of Sendai Virus Vectors Carrying Human Transcriptional Factors

On the previous day of transfection, $10^6$ 293T/17 cells were seeded into each well of a 6-well plate, and cultured in a $CO_2$ incubator (5% $CO_2$) at 37° C. Using 15 μl A of TransIT-LT1 (Mirus), the 293T/17 cells were transfected with a mixture of: 0.5 μg of pCAGGS-NP, 0.5 μg of pCAGGS-P4C (−), 2 μg of pCAGGS-L (TDK), 0.5 μg of pCAGGS-T7, 0.5 μg of pCAGGS-F5R (WO2005/071085), and 5.0 μg of an above-described Sendai virus vector plasmid carrying a human transcriptional factor (pSeV18+c-Myc/TSΔF, pSeV18+Sox2/TSΔF, pSeV18+KLF4/TSΔF, or pSeV18+Oct3/4/TSΔF). The cells were cultured in a $CO_2$ incubator at 37° C. for two days. Then, $10^6$ cells of LLC-MK2/F/A which express the fusion protein (F protein) of Sendai virus (Li, H.-O. et al., J. Virology 74. 6564-6569 (2000); WO00/70070) were overlaid onto the transfected 293T/17 cells in each well. Then, the cells were cultured in a $CO_2$ incubator at 37° C. for one day. On the following day, the cell culture medium was removed, and the cells were washed once with 1 ml of MEM supplemented with penicillin-streptomycin (hereinafter abbreviated as PS/MEM). 1 ml of PS/MEM containing 2.5 μg/ml trypsin (hereinafter abbreviated as Try/PS/MEM) was added to each well. The cells were cultured in a $CO_2$ incubator at 32° C. for two days. The cells were continuously cultured while exchanging the medium every three to four days, and in some cases, passaging with LLC-MK2/F/A cells. An aliquot of the culture supernatant was assessed for vector collection by hemagglutination assay. The culture supernatant was harvested after sufficient hemagglutination was observed. RNA was extracted from the harvested culture supernatant using a QIAamp Viral RNA Mini Kit (QIAGEN, catalog No. 52906), and then subjected to RT-PCR that targets a region of the inserted transcription factor. Whether the obtained RT-PCR product has the correct nucleotide sequence was confirmed by sequencing. Thus, the following vectors were constructed:

(a) F gene-deficient Sendai virus vector carrying the Oct3/4 gene (hereinafter referred to as "SeV18+Oct3/4/TSΔF vector")
(b) F gene-deficient Sendai virus vector carrying the Sox2 gene (hereinafter referred to as "SeV 18+Sox2/TSΔF vector")
(c) F gene-deficient Sendai virus vector carrying the KLF4 gene (hereinafter referred to as "SeV18+Klf4/TSΔF vector")
(d) F gene-deficient Sendai virus vector carrying the c-Myc gene (hereinafter referred to as "SeV18+c-Myc/TSΔF vector")

Example 1

Preparation of ES-Like Cells Using Sendai Virus Vectors Carrying Foreign Genes

First, $8.0 \times 10^5$ cells each of human newborn foreskin-derived fibroblast (BJ) (ATCC (http://www.atcc.org); CRL-2522), human adult skin-derived fibroblast (HDF) (Applications, Inc. 106-05A-1388; derived from the cheek of a 36-year-old white female), and human fetal lung cell-derived fibroblast (MRC5; ATCC CCL-171) were cultured in DMEM (GIBCO-BRL, 11995)/10% FBS (GIBCO-BRL) in a $CO_2$ incubator (0.5% $CO_2$) at 37° C. for one day (DMEM (GIBCO-BRL, 11995)/10% FBS (GIBCO-BRL)).

After culturing, the vectors of (a) to (d) below were added at an MOI of 3 to the cultured cells.
(a) SeV18+Oct3/4/TSΔF vector
(b) SeV18+Sox2/TSΔF vector
(c) SeV18+Klf4/TSΔF vector
(d) SeV18 c-Myc/TSΔF vector After addition of the above vectors, the medium (DMEM (GIBCO-BRL; 11995)/10% FBS (GIBCO-BRL)) was exchanged on the next day.

The cells were cultured in a $CO_2$ incubator (0.5% $CO_2$) at 37° C. for seven or eight days. Then, the cells into which the vectors were introduced were detached with 0.25% trypsin. $5.0 \times 10^4$ to $1.0 \times 10^6$ cells were cultured on $5.0 \times 10^5$ mitomycin-treated feeder cells (for example, MEF) prepared in gelatin-coated 10-cm culture dishes. On the following day, the DMEM/10% FBS medium was exchanged with Primate ES Cell Culture Medium (ReproCell; RCHEMD001) supplemented with 4 ng/ml bFGF, and the cells were cultured in a $CO_2$ incubator (3% $CO_2$). The medium was exchanged every one or two days. The medium may be a feeder cell-conditioned medium.

Colonies appeared after several days. Human ES cell-like colonies became visible after about 20 days of culture (FIG. 1; derived from BJ).

As seen from the photographs shown in FIG. 1, flat colonies, which were similar to those of human ES cells and obviously distinct from those of fibroblasts (BJ) before induction, were observed (Jikken Igaku (Experimental Medicine) Vol. 26, No. 5 (suppl.) pp. 35-40, 2008). It was possible to isolate the colonies and culture them on fresh feeder cells. The cells were able to be detached using an ES cell-detaching solution (mixture of trypsin and collagenase; ReproCell, RCHETP002), passaged, and grown.

The experiments described below were further conducted to test whether the cells prepared by the above initialization experiment express undifferentiated markers characteristic of ES cells.

Example 2

Figure 2:
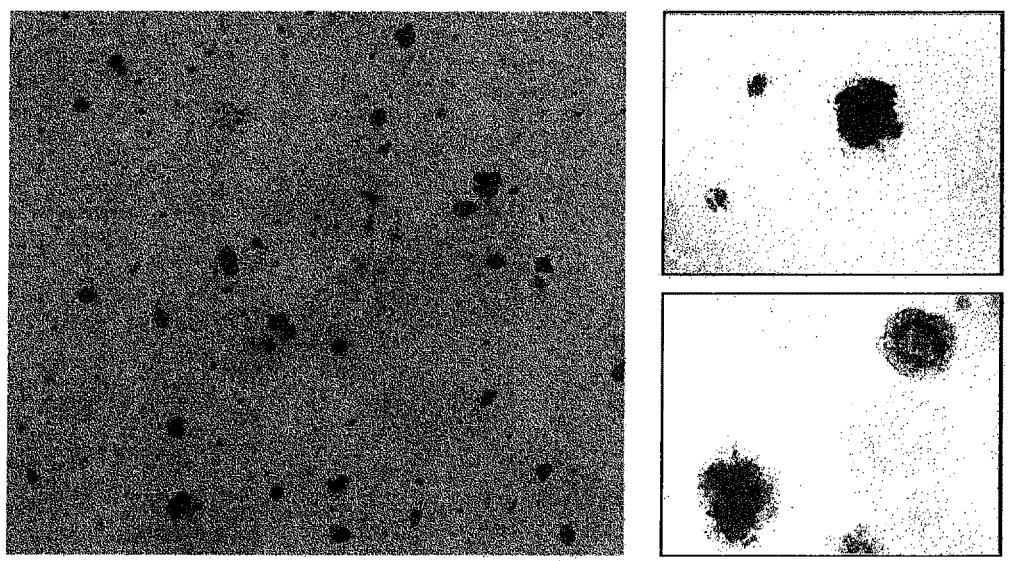
FIG. 2 shows the results of staining of the cells obtained by the methods according to the present invention by alkaline phosphatase.

Alkaline Phosphatase Staining of Cells Prepared by the Above Initialization Experiment The alkaline phosphatase activity, which is an undifferentiated marker for ES cells, was visualized by staining with NBCT/BCIP (PIERCE; NBT/BCIP, 1-Step, #34042). Colonies stained blue, which were positive for alkaline phosphatase, were observed (FIG. 2).

Example 3

Figure 3:
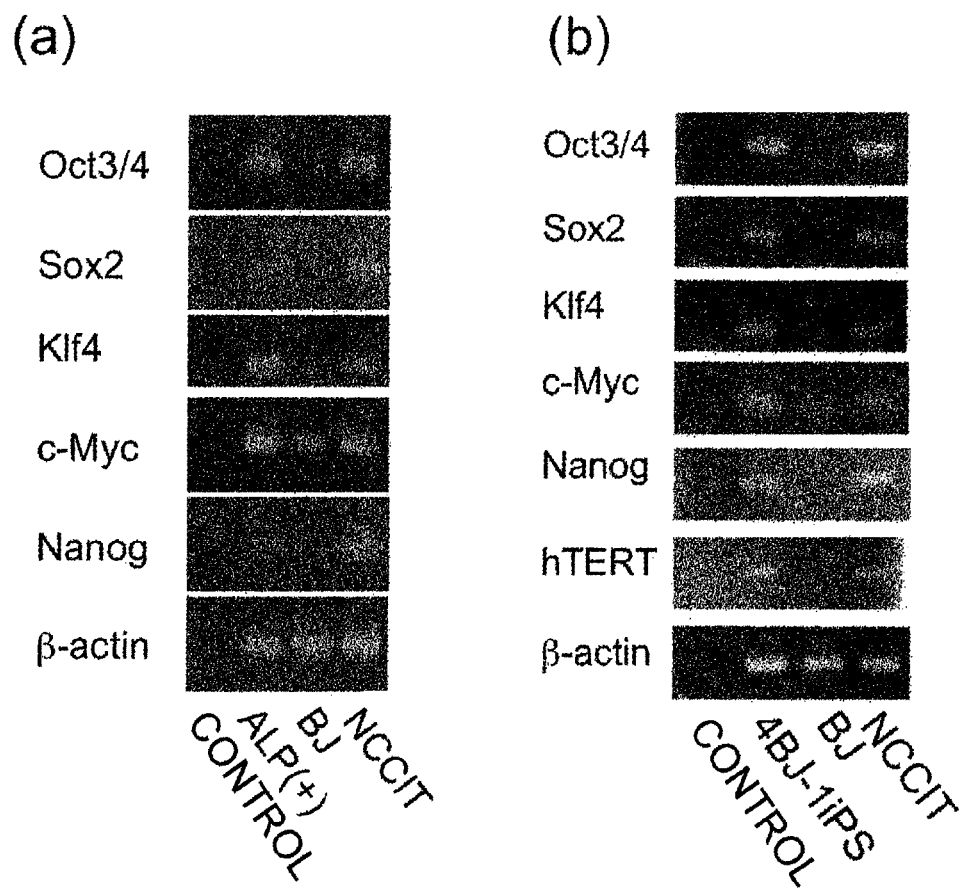
FIG. 3 shows the intracellular expression levels of specific genes of the cells obtained by the methods according to the present invention. The results of RT-PCR using mRNA prepared from the alkaline phosphatase-positive colony group (ALP(+)) (panel (a)) and mRNA prepared from a single colony (panel (b)) are shown. In these cells, expression of Oct3/4, Sox2, Klf4, and c-Myc were confirmed, and in addition, expression of Nanog which is an ES cell marker was also observed (panels (a) and (b)). Furthermore, in cells passaged from a single clone, expression of hTERT which is a telomerase activation indicator indicating infinite proliferation ability was observed (panel (b)). BJ: Cells not introduced with a vector. NCCIT: fetal carcinoma cells (positive control). The control is a negative control without template DNA.

Assessment of the Expression Levels of Specific Genes in Cells Prepared by the Above Culture Multiple alkaline phosphatase-positive colonies (ALP(+)) described above in Example 2 were mixed, and RNA was extracted from them ("ALP(+)" in FIG. 3(a)). Reverse transcription was carried out using random primers. PCR was performed using respective primers (FIG. 3(a)).

The primer sequences are shown below:

```
Fw:
5'-GATCCTCGGACCTGGCTAAGC-3'      (SEQ ID NO: 25)
and

Rv:
5'-GCTCCAGCTTCTCCTTCTCCAGC-3'   (SEQ ID NO: 26)
for Oct3/4;

Fw:
5'-AGCGCTGCACATGAAGGAGCACC-3'   (SEQ ID NO: 27)
and

Rv:
5'-ATGCGCTGGTTCACGCCCGCGCCCAGG-3' (SEQ ID NO: 28)
for Sox2;

Fw:
5'-GCTGCACACGACTTCCCCCTG-3'     (SEQ ID NO: 29)
and

Rv:
5'-GGGGATGGAAGCCGGGAGGAAGCGG-3' (SEQ ID NO: 30)
for KLF4;

Fw:
5'-TCTCAACGACAGCAGCTCGC-3'      (SEQ ID NO: 31)
and
```

```
Rv:
5'-CAGGAGCCTGCCTCTTTTCCACAGA-3'   (SEQ ID NO: 32)
for c-myc;

Fw:
5'-TACCTCAGCCTCCAGCAGAT-3'        (SEQ ID NO: 33)
and

Rv:
5'-TGCGTCACACCATTGCTATT-3'        (SEQ ID NO: 34)
for Nanog;
and

Fw:
5'-CAACCGCGAGAAGATGAC-3'          (SEQ ID NO: 35)
and

Rv:
5'-AGGAAGGCTGGAAGAGTG-3'          (SEQ ID NO: 36)
for β-actin.
```

Furthermore, single ES-like cell colonies were isolated and RT-PCR was carried out by the same method as described above ("4BJ-1iPS" in FIG. 3(b)). At the same time, hTERT expression was also assessed using the following primers:

```
Fw:
5'-TGCCCGGACCTCCATCAGAGCCAG-3'    (SEQ ID NO: 37)
and

Rv:
5'-TCAGTCCAGGATGGTCTTGAAGTCTG-3'. (SEQ ID NO: 38)
```

The c-Myc expression level was elevated, and the expression of introduced genes (Oct3/4, Sox2, and Klf4), which was not detectable in fibroblasts (BJ) before induction, was detected. It was also revealed that the expression of Nanog, which is an ES cell marker, was induced ("ALP(+)" in FIG. 3(a)) as in embryonic carcinoma cells (NCCIT) as a positive control. Nanog is a newly identified homeo-domain protein (Cell, Vol. 113, 631-642, 2003), which is specifically expressed in pluripotent stem cells such as ES and EG cells, and early embryos. Nanog is involved in the signal transduction system for the pluripotency and maintenance of autonomous replication ability. Furthermore, the cells derived from single colonies were demonstrated to express the undifferentiated ES cell marker genes and hTERT, which is an indicator for telomerase activation that shows the ability of infinite proliferation ("4BJ-1iPS" in FIG. 3(b)). The above findings support that the cells isolated from the colonies were pluripotent stem cells.

Example 4

Preparation of Inducible Pluripotent Stem Cells Using Mutant c-Myc

Preparation of the Human Transcriptional Factor c-Myc with Silent Mutations Introduced (Hereinafter Referred to as "c-rMyc")

PCR was carried out (94° C. for three minutes, and 25 cycles of [98° C. for 30 seconds, 55° C. for 30 seconds, and 72° C. for six minutes], followed by 72° C. for seven minutes) using pBS-KS-c-Myc as a template, together with PrimeStar HS DNA polymerase (Takara Bio, catalog No. R010A) and the following six primers for mutagenesis:
(c-rMyc1-F (5'-CGGACGACGAGACCTTCATCAAGAA-CATCATCATCCAGGACTG-3' (SEQ ID NO: 39)), c-rMyc1-R (5'-CAGTCCTGGATGATGATGTTCT-TGATGAAGGTCTCGTCGTCCG-3' (SEQ ID NO: 40)), c-rMyc2-F (5'-GAACGAGCTAAAACGGAGCTTCT-TCGCCCTGCGTGACCAGATCC-3' (SEQ ID NO: 41)), c-rMyc2-R (5'-GGATCTGGTCACGCAGGGCGAA-GAAGCTCCGTTTTAGCTCGTTC-3' (SEQ ID NO: 42)), c-rMyc3-F (5'-CCCAAGGTAGTTATCCTTAA-GAAGGCCACAGCATACATCCTGTC-3' (SEQ ID NO: 43)), and c-rMyc3-R (5'-GACAGGATGTATGCTGTG-GCCTTCTTAAGGATAACTACCTTGGG-3' (SEQ ID NO: 44))). The PCR product was treated with DpnI at 37° C. for two hours. E. coli DH5α (ToYoBo, Code No. DNA-903) was transformed with 5 µl of the reaction mixture. 16 E. coli colonies were isolated and mini-prep was performed. A clone that has the correct sequence was selected by sequencing, and thus pBS-KS-c-rMyc was obtained. pBS-KS-c-rMyc was digested with NotI at 37° C. for three hours, and separated by electrophoresis using 1% agarose gel. A band of about 1.5 kbp was excised, and the DNA was purified using a Qiaquick Gel Extraction Kit (QIAGEN, catalog No. 28706). The NotI fragment containing the c-rMyc gene was cloned into the NotI site of the pSeV (HNL)TSΔF vector. A clone that has the correct sequence was selected by sequencing, and thus pSeV(HNL)-c-rMyc/TSΔF was obtained. The nucleotide and amino acid sequences of c-rMyc are shown in SEQ ID NOs: 45 and 46, respectively. c-rMyc has the a378g, t1122c, t1125c, a1191g, and a1194g mutations.

pSeV(HNL)/TSΔF was constructed as follows. PCR was carried out (94° C. for one minute, and 30 cycles of [94° C. for 30 seconds, 55° C. for one minute, and 68° C. for 22 minutes], followed by 68° C. for seven minutes) using Litmus SalIN-heIfrg PmutMtsHNts ΔF-GFP (International Publication No. WO2003/025570) as a template, together with the following primers:
del GFP-Pac F (5'-GAGGTCGCGCGTTAAT-TAAGCTTTCACCTCAAACAAGCACAGATCATGG-3' (SEQ ID NO: 47)) and del GFP-Pac R (5'-GCAT-GTTTCCCAAGGGGAGAGTTAATTAACCAAGCACT CACAAGGGAC-3' (SEQ ID NO: 48)). The PCR product was treated in succession with PacI and DpnI. The resulting product was self-ligated. A plasmid that has the correct sequence without the GFP gene was selected by sequencing, and thus Litmus SalINheIfrg PmutMtsHNts ΔF-GFP delGFP was obtained. PCR was carried out (94° C. for three minutes, and 25 cycles of [98° C. for 10 seconds, 55° C. for 15 seconds, and 72° C. for 12 minutes], followed by 72° C. for seven minutes) using Litmus SalINheIfrg Pmut-MtsHNts ΔF-GFP delGFP as a template, together with the following primers:
HNLNOTI-F:5'-GGGTGAATGGGAAGCGGCCGCTAG-GTCATGGATGG-3' (SEQ ID NO: 49) and HNLNOTI-R: 5'-CCATCCATGACCTAGCGGCCGCTTC-CCATTCACCC-3' (SEQ ID NO: 50). The PCR product was digested with DpnI, and then E. coli DH5α (ToYoBo, Code No. DNA-903) was transformed with 20 µl of the reaction mixture. Six E. coli colonies were isolated and mini-prep was performed. A plasmid that has the inserted NotI sequence was selected by NotI digestion. Then, a clone that has the correct sequence was selected by sequencing. Thus, Litmus SalINheIfrg PmutMtsHNts (HNL)-dF was obtained. Then, Litmus SalINheIfrg Pmut-MtsHNts(HNL)-dF was digested with SalI and NheI. The resulting fragment was ligated to a fragment prepared by SalI/NheI digestion of the pSeV/ΔSalINheIfrg Lmut plasmid (International Publication No. WO2003/025570) whose L gene has two mutations. Thus, pSeV (HNL)/ TSΔF was obtained. This vector encodes the same viral proteins as SeV18+/TSΔF, and has an insertion site (NotI site) for an introduced gene between the HN and L genes.

Preparation of a Sendai Virus Vector Carrying c-rMyc (the SeV(HNL)-c-rMyc/TSΔF Vector)

On the previous day of transfection, $10^6$ 293T/17 cells were seeded into each well of a 6-well plate, and cultured in a $CO_2$ incubator (5% $CO_2$) at 37° C. Using 15 μl of TransIT-LT1 (Mirus), the 293T/17 cells were transfected with a mixture of: 0.5 μg of pCAGGS-NP, 0.5 μg of pCAGGS-P4C (−), 2 μg of pCAGGS-L (TDK), 0.5 μg of pCAGGS-T7, 0.5 μg of pCAGGS-F5R, and 0.5 μl of the Sendai virus vector plasmid pSeV(HNL)-c-rMyc/TSΔF described above that carries the human transcriptional factor c-rMyc. The cells were cultured in a $CO_2$ incubator at 37° C. for two days. Then, $10^6$ LLC-MK2/F/A cells which express the fusion protein (F protein) of Sendai virus were overlaid onto the transfected 293T/17 cells in each well, and the cells were cultured in a $CO_2$ incubator at 37° C. for one day. On the following day, the cell culture medium was removed, and the cells were washed once with 1 ml of MEM supplemented with penicillin-streptomycin (hereinafter abbreviated as PS/MEM). 1 ml of PS/MEM containing 2.5 μg/ml trypsin (hereinafter abbreviated as Try/PS/MEM) was added to each well. The cells were cultured in a $CO_2$ incubator at 32° C. for two days. The cells were continuously cultured while exchanging the medium every three to four days, and in some cases, passaging with LLC-MK2/F/A cells. An aliquot of the culture supernatant was assessed for vector collection by hemagglutination assay. The culture supernatant was harvested after sufficient hemagglutination was observed. RNA was extracted from the harvested culture supernatant using a QIAamp Viral RNA Mini Kit (QIAGEN, catalog No. 52906), and subjected to RT-PCR that targets a region of inserted c-rMyc. Whether the obtained RT-PCR product has the correct nucleotide sequence was confirmed by sequencing. Thus, the SeV(HNL)-c-rMyc/TSΔF vector was obtained.

Example 5 iPS Induction Efficiency of Sendai Virus Vectors Carrying Reprogramming Factors

The iPS induction efficiency of Sendai virus vectors carrying reprogramming factors is shown in the Table. The number of ES-like colonies formed is shown along with the number of Sendai virus-infected cells overlaid onto feeder cells. The experiment was carried out as described in Example 1, except that the above c-rMyc-carrying vector was additionally used.

Of the reprogramming factors, Oct3/4, Sox2, Klf4, and c-Myc, modified c-Myc (c-rMyc) maximized the number of colonies formed, when it was inserted into the HNL site of the vector. The induction efficiency was about ten times greater than that achieved by using retroviral vectors. Meanwhile, even when the three factors excluding Myc were used, iPS induction was possible utilizing the Sendai virus vectors. Furthermore, using the Sendai virus vectors, iPS cells could be induced not only from human newborn foreskin-derived cells (BJ) but also from human adult skin-derived cells (HDF) with an efficiency comparable to that of BJ. This result demonstrates that the methods of the present invention, which are simpler than conventional methods, allow high efficiency iPS cell induction.

TABLE 1

| Parental strain | Origin | Number of cells seeded | Number of ES-like colonies | c-Myc |
|---|---|---|---|---|
| BJ | Human newborn foreskin | $5 \times 10^5$ | 14 | Wild type |
| HDF | Human adult skin (face) | $5 \times 10^5$ | 25 | Wild type |
| BJ | | $5 \times 10^4$ | 28 | Wild type |
| BJ | | $3.5 \times 10^4$ | 58 | Wild type |
| BJ | | $3.5 \times 10^4$ | 67 | HNL-rMyc |
| BJ | | $5 \times 10^4$ | 118 | HNL-rMyc |
| BJ | | $3.5 \times 10^5$ | 6 | Without Myc |

"Wild type" indicates the SeV18 + c-Myc/TSΔF vector carrying the wild-type c-Myc gene.
"HNL-rMyc" indicates the pSeV(HNL)-c-rMyc/TSΔF vector carrying the silent mutant c-rMyc gene between the HN and L genes, which is described in Example 4.

Example 6

Figure 4:
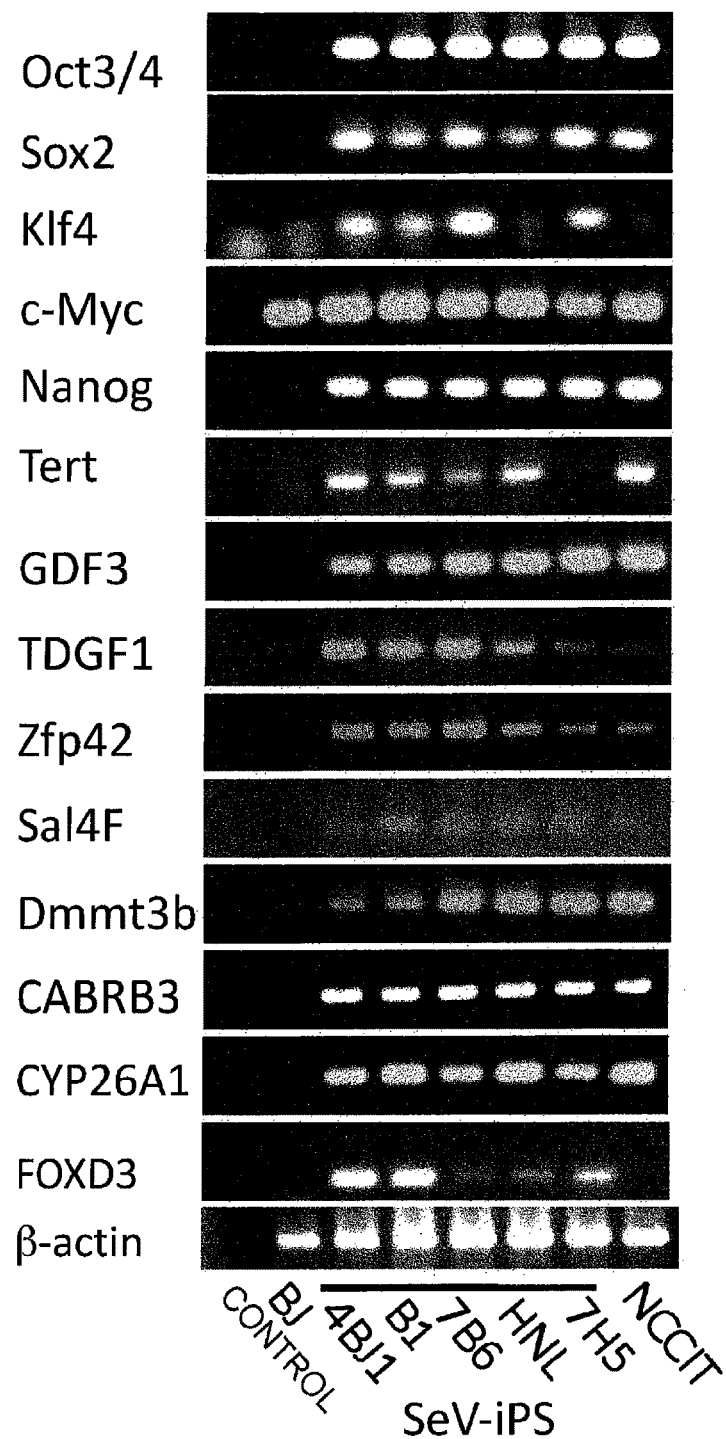
FIG. 4 shows the expression of ES marker in the cells obtained by the methods according to the present invention. BJ: Cells not introduced with a vector. NCCIT: fetal carcinoma cells (positive control). The control is a negative control without template DNA.

ES Marker Expression in iPS Cells iPS cells induced by the Sendai virus vectors carrying reprogramming factors were assessed for ES marker expression. iPS cells were induced as described in Example 1, except that the above c-rMyc-carrying vector was additionally used. ES cell-like colonies were isolated using a stem cell knife (NIPPON MEDICAL & CHEMICAL INSTRUMENTS CO.) under a microscope, and then passaged. RNA was extracted from each strain, and RT reaction and PCR were carried out in the same way as in FIG. 3. RT-PCR was performed to assess the expression of ES cell markers such as Oct3/4, Nanog, Tert, and the following eight genes: GDF3, TDGF1, Zfp42, Sal4F, Dmmt3b, CABRB3, CYP26A1, and FoxD3 (Adewumi, O. et al., Characterization of human embryonic stem cell lines by the International Stem Cell Initiative. Nat. Biotechnol. 25, 803-816, 2007), and the expression of the reprogramming factors, Sox2, Klf4, and c-Myc. The method is as described in Example 3. It was demonstrated that all five clones expressed all of the markers (FIG. 4).

The primers used are listed below:

```
TERT F2847
(TGCCCGGACCTCCATCAGAGCCAG (SEQ ID NO: 37))
and

TERT R3399
(TCAGTCCAGGATGGTCTTGAAGTCTG (SEQ ID NO: 38))
for TERT;

GDF3 F
(GGCGTCCGCGGGAATGTACTTC (SEQ ID NO: 51))
and

GDF3 R
(TGGCTTAGGGGTGGTCTGGCC (SEQ ID NO: 52))
for GDF3;

TDGF1-F1
(ATGGACTGCAGGAAGATGGCCCGC (SEQ ID NO: 53))
and

TDGF1-R567
(TTAATAGTAGCTTTGTATAGAAAGGC (SEQ ID NO: 54))
for TDGF1;

Zfp42-F1
(ATGAGCCAGCAACTGAAGAAACGGGCAAAG (SEQ ID NO: 55))
and
```

-continued

Zfp42-R933
(CTACTTTCCCTCTTGTTCATTCTTGTTCG (SEQ ID NO: 56))
for Zfp42;

SalI4 F
(AAACCCCAGCACATCAACTC (SEQ ID NO: 57))
and

SalI4 R
(GTCATTCCCTGGGTGGTTC (SEQ ID NO: 58))
for SalI4;

Dnmt3b F
(GCAGCGACCAGTCCTCCGACT (SEQ ID NO: 59))
and

Dnmt3b R
(AACGTGGGGAAGGCCTGTGC (SEQ ID NO: 60))
for Dmmt3b;

GABRB3 F
(CTTGACAATCGAGTGGCTGA (SEQ ID NO: 61))
and

GABRB3 R
(TCATCCGTGGTGTAGCCATA (SEQ ID NO: 62))
for GABRB3;

CYP26A1 F
(AACCTGCACGACTCCTCGCACA (SEQ ID NO: 63))
and

CYP26A1 R
(AGGATGCGCATGGCGATTCG (SEQ ID NO: 64))
for CYP26A1;

FoxD3-F418
(GTGAAGCCGCCTTACTCGTAC (SEQ ID NO: 65))
and

FoxD3-R770
(CCGAAGCTCTGCATCATGAG (SEQ ID NO: 66))
for FOXD3;

F6
(ACAAGAGAAAAAACATGTATGG (SEQ ID NO: 67))
and

OCT3/4 R259
(GAGAGGTCTCCAAGCCGCCTTGG (SEQ ID NO: 68))
for SeV-Oct3/4;

Sox2-F294
(AGCGCTGCACATGAAGGAGCACC (SEQ ID NO: 27))
and

R150
(AATGTATCGAAGGTGCTCAA (SEQ ID NO: 69))
for SeV-Sox2;

F6
(ACAAGAGAAAAAACATGTATGG (SEQ ID NO: 67))
and

KIF4-R405
(CGCGCTGGCAGGGCCGCTGCTCGAC (SEQ ID NO: 70))
for SeV-Klf4;

F6
(ACAAGAGAAAAAACATGTATGG (SEQ ID NO: 67))
and c-rMyc406
(TCCACATACAGTCCTGGATGATGATG (SEQ ID NO: 71))
for SeV-c-Myc;
and F8424
(TAACTGACTAGCAGGCTTGTCG (SEQ ID NO: 72))
and c-rMyc406
(TCCACATACAGTCCTGGATGATGATG (SEQ ID NO: 71))
for c-Myc/HNL.

Example 7

Telomerase Activity of iPS Cells

Telomerase activity was assayed to assess the ability of infinite proliferation of the iPS cells induced with the Sendai virus vectors carrying reprogramming factors. iPS cells were induced as described in Example 1, except that the above c-rMyc-carrying vector (referred to as HNL) was additionally used. A TRAPEZE™ Telomerase Detection Kit (CHEMICON, Cat. No. S7700) was used to detect the telomerase activity. The cells were harvested, and 200 μl of 1× CAPS lysis buffer attached to the kit was added thereto. The cells were suspended by pipetting. This was incubated on ice for 30 minutes, and then centrifuged in a refrigerated microfuge at 12,000 rpm and 4° C. for 20 minutes. 160 μl of the supernatant was transferred to another Eppendorf tube, and this cell lysate was assessed for its protein concentration. Before the assay, an aliquot of the cell lysate including 1 μg of protein was placed into an Eppendorf tube and heated at 85° C. for ten minutes. 1 μg each of the heat-treated and non-treated samples was used for TRAP assay. For each assay, a reaction mixture was prepared by combining the following: 5.0 μl of 10×TRAP reaction buffer, 1.0 μl of 50× dNTP mix, 1.0 μl of TS primer, 10 μl of TRAP primer mix, 40.6 μl of [cell lysate (1 μg of protein) and water], and 0.4 μl of Taq polymerase. PCR was carried out as follows: 30° C. for 30 minutes, followed by 30 cycles of [94° C. for 30 seconds, 59° C. for 30 seconds, and 72° C. for 60 seconds]. 6× loading dye was added to the PCR reaction mixture. 20 μl of this was loaded onto 10% or 12.5% polyacrylamide gel. The gel after electrophoresis was stained with ethidium bromide.

Figure 5:
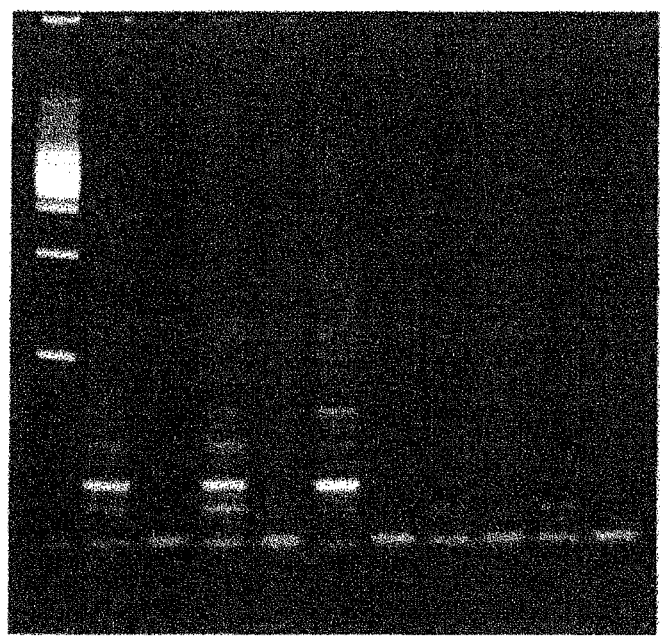
FIG. 5 shows the results of detecting telomerase activity in cells obtained by the methods according to the present invention.

All iPS clones exhibited telomerase activity. The activity was not detected in the parental BJ and HDF lines which are controls, and heat-treated iPS cells (FIG. 5).

Example 8

Pluripotency of iPS Cells

Figure 6:
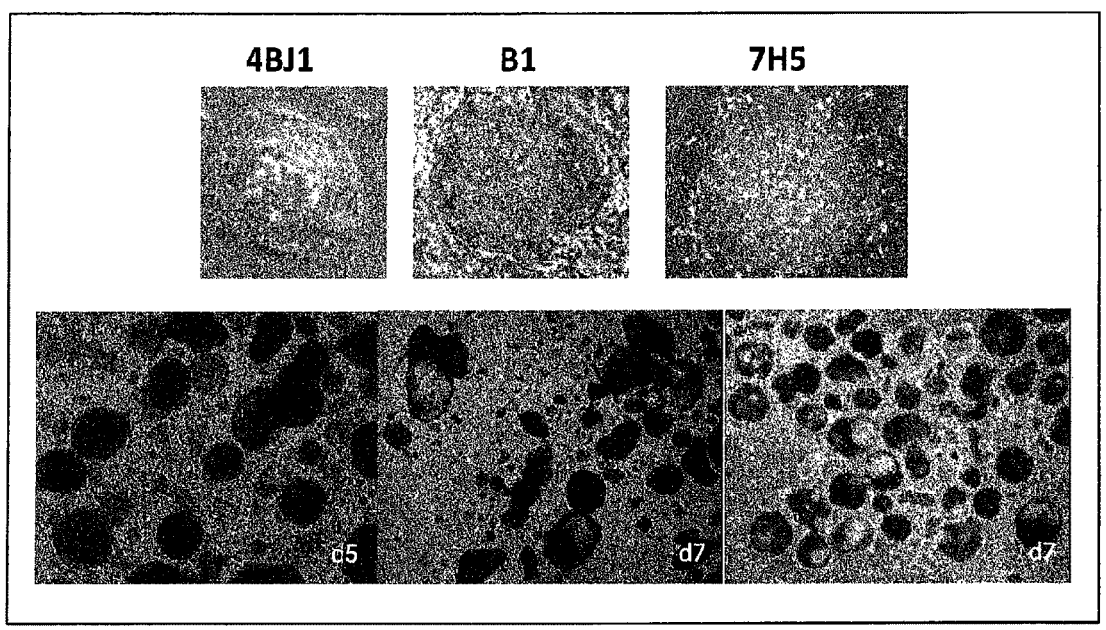
FIG. 6 shows the pluripotency of the cells obtained by the methods according to the present invention. Results of experiments on embryoid body formation are shown.

An in vitro embryoid body formation experiment was conducted to assess the pluripotency of iPS cells induced with the Sendai virus vectors carrying reprogramming factors. iPS cells were induced as described in Example 1. Colonies of three iPS clones, 4BJ1, B1 (derived from BJ), and 7H5 (derived from HDF), were detached from dishes using collagenase IV (Invitrogen, 17104-019). The cell masses were transferred into MPC-coated wells (Nunc, 145383) and incubated for several days in suspension culture in RPMI 1640 supplemented with 10% FBS. Embryoid body formation was observed under a microscope. iPS cells induced with the Sendai virus vectors had differentiation ability, and all the iPS cells formed embryoid bodies. Many cystic embryoid bodies at a more differentiated stage were observed on day seven (FIG. 6).

Figure 7:
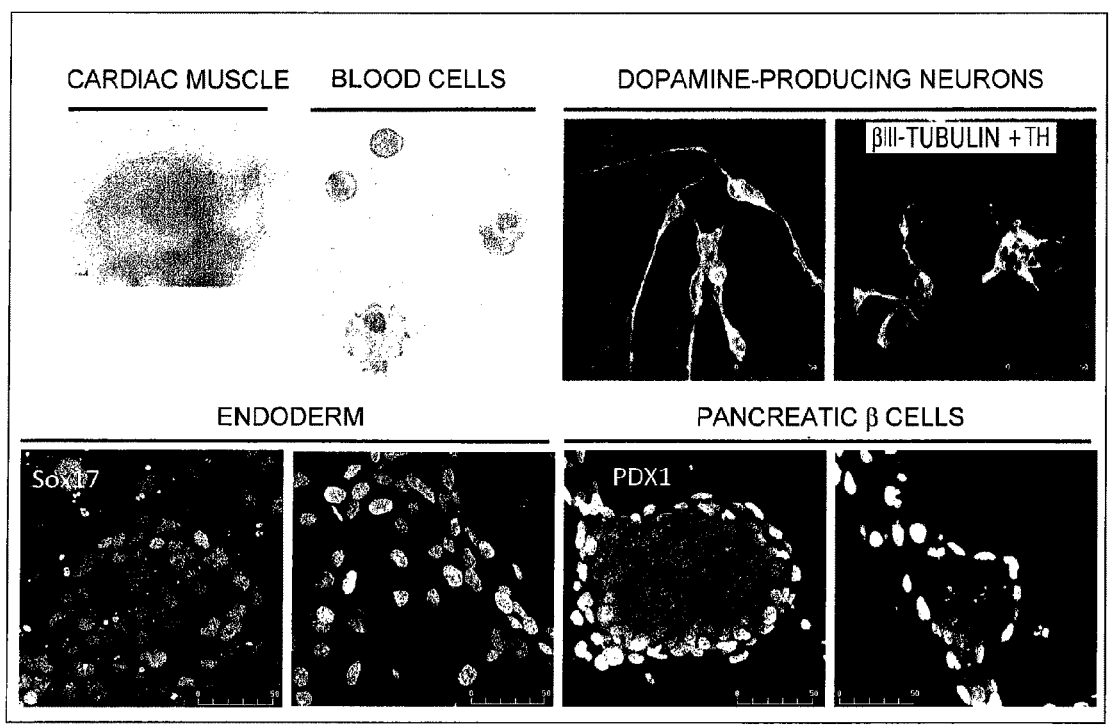
FIG. 7 shows the pluripotency (in vitro) of the cells obtained by the methods according to the present invention. It shows in vitro differentiation of virus-free induced pluripotent stem (iPS) cells induced by the vectors of the present invention from human BJ cells into useful cells derived from the mesoderm (myocardial and blood cells), ectoderm (TH-positive dopamine-producing neuron), endoderm (Sox17-positive cells and PDX-positive pancreatic β cells).

Furthermore, to show the pluripotency for triploblastic differentiation of iPS cells induced with the Sendai virus vectors (SeV-iPS), the cells were induced in vitro for differentiation into cardiac muscle cells (mesoderm), dopamine-producing neurons (ectoderm), and pancreatic cells (endoderm). SeV-iPS clones from which SeV vectors were removed were detached from feeder cells using 1 mg/ml collagenase IV. For cardiac muscle cell induction, the cells were incubated for six days in suspension culture in NPC-coated plates containing DMEM supplemented with 20% FBS and 0.1 mM vitamin C. After formation of embryoid bodies, they were transferred into plates coated with 0.1% gelatin, and cultured for one week. Thus, pulsing cardiac muscle was obtained (Takahashi, T. et. al., Circulation 107, 1912-1916, 2003). For dopamine-producing neuron induction, iPS cells were isolated in the same manner, and seeded onto confluent PA6 feeder cells (RIKEN BRC) in 0.1% gelatin-coated plates. The cells were cultured for 16 days in GMEM (Invitrogen) supplemented with 10% KSR, 2 mM L-glutamine and nonessential amino acids, and 2-mercaptoethanol at a final concentration of $1\times10^{-4}$ M. After fixation with 10% formalin solution, the cells were stained with an anti-βIII tubulin antibody (SantaCruz; 2G10) and an anti-tyrosine hydroxylase antibody (Chemicon; P07101) to assess whether they are dopamine-producing neurons (Kawasaki, H. et al., Neuron 28, 31-40 (2000)). For pancreatic cell induction, SeV-iPS cells were cultured for four days on MMC-treated MEF feeder cells in RPMI 1640 supplemented with 2% FBS and 100 ng/ml activin A (R&D Systems). Then, the cells further cultured for eight days in DMEM/F12 medium supplemented with N2 and B27 supplements, 2 mM L-glutamine and nonessential amino acids, $1\times10^{-4}$M 2-mercaptoethanol, and 0.5 mg/ml BSA (Invitrogen). The cells were fixed with 10% formalin solution, and stained with an anti-PDX antibody (R&D Systems; AF2419) and an anti-SOX17 antibody (R&D Systems; 245013) to detect pancreatic β cells and endodermal cells, respectively (D'Amour, K. A. et al., Nat. Biotechnol. 23, 1534-1541 (2005)) (FIG. 7).

Figure 8:
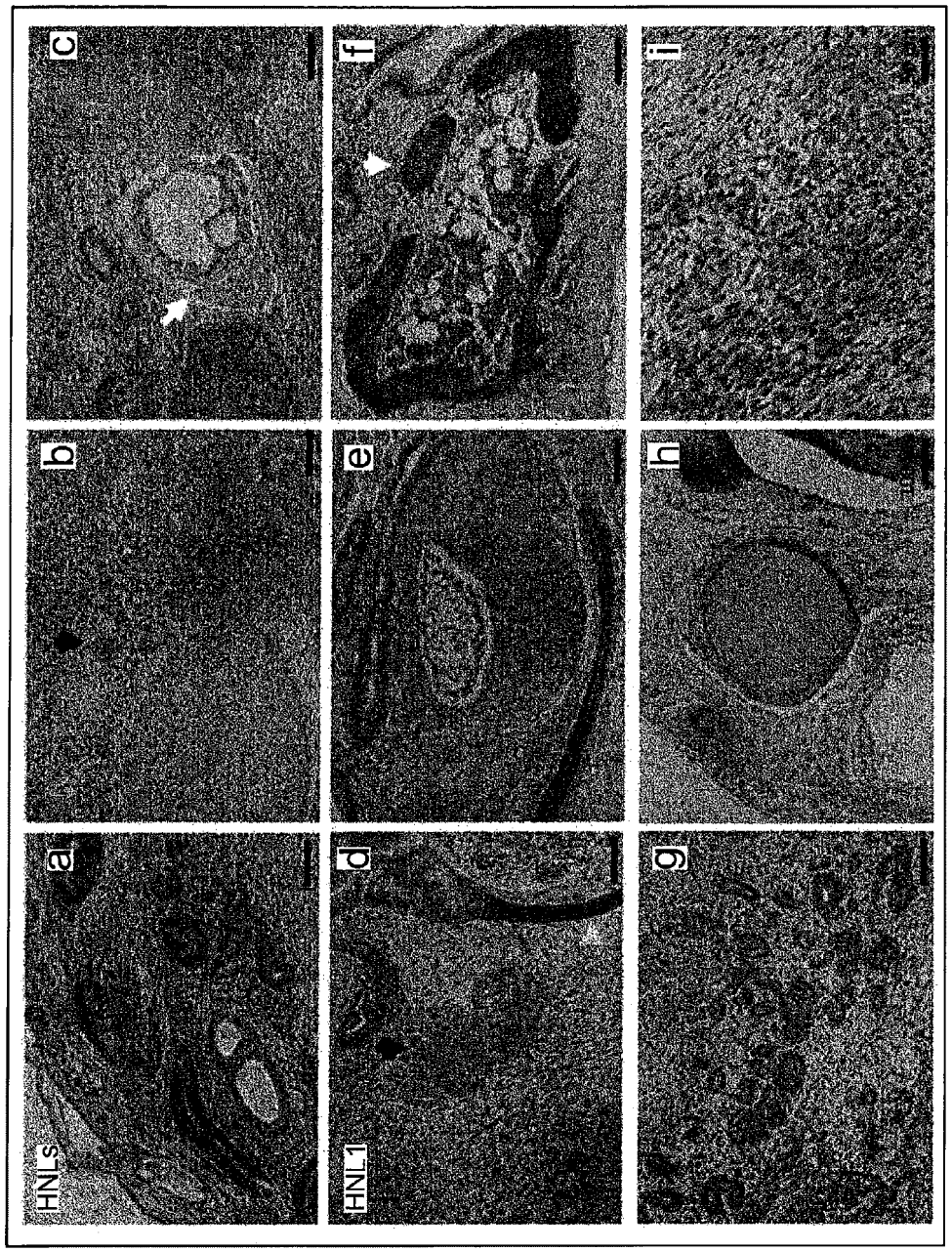
FIG. 8 shows the pluripotency (in vitro) of cells obtained by the methods according to the present invention. Teratoma produced by subcutaneous administration to immunodeficient mice of virus-free iPS cells, NHLs and NHL1, induced by the vectors of the present invention from human BJ cells. a: various differentiated tissues. b: cartilage and secretory cell (black arrow). c: bone tissue. d: secretory tissue (black arrow) and retina-like tissue (white arrow) differentiated from the neuroepithelium. e: transitional epithelial tissue (center). f: cartilage and myeloid tissue (white arrow). g: gastrointestinal-like tissue. h: spherical tissue. i: myocardial-like tissue

Furthermore, the in vitro pluripotency was confirmed by teratoma formation in immunodeficient mice. SeV-iPS cells were subcutaneously inoculated into SCID mice. Tumor formation was observed after about one month. Then, after about two months, samples were collected and fixed with 10% formalin, and embedded in paraffin. Tissue sections were stained with hematoxylin/eosin to assess the triploblastic differentiation (FIG. 8).

Example 9

Promoter Analysis of iPS Cells

Figure 9:
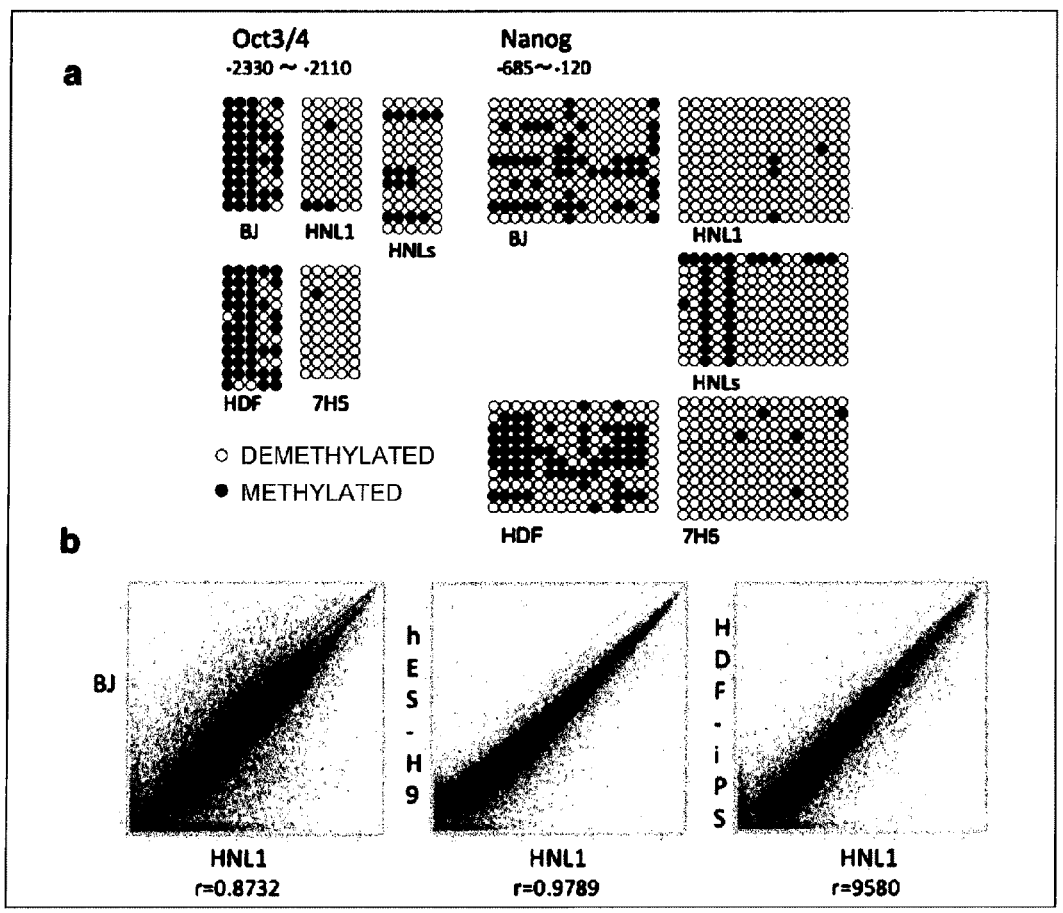
FIG. 9 shows the epigenetics of the cells obtained by the methods according to the present invention. a: The activated state of the human ES cell-specific promoter region was analyzed by the bisulfite sequencing method for each of Oct3/4 and Nanog. The activated demethylated regions are indicated by white circles and methylated regions are indicated by black circles. Analyses were carried out on SeV-iPS clones, HNL1 and HNLs, derived from the parent human neonatal foreskin cell line BJ and on SeV-iPS clone 7115 derived from human adult skin cells HDF. All SeV-iPS cells showed activation of the corresponding promoters in both regions. b: Gene expression analyses by microarray were carried out on the virus-free iPS cell HNL1 induced by SeV from human BJ cells, and comparison with BJ cells which are the parent cell line and human ES cell line H9 was performed. The correlation coefficient is indicated as r. As a result, compared to the already reported retrovirus-induced human iPS cell HDF-iPS, SeV-iPS which became free of foreign genes showed a profile closer to that of human ES cell line H9 (correlation coefficient r=0.9789).

To assess whether the Oct3/4 and Nanog gene promoters, which are expressed in ES cells, are also activated in iPS cells, methylation analysis was performed by the bisulfite sequencing method described below. The result showed that the Oct3/4 promoter (region from −2330 to −2110) and Nanog promoter (region from −685 to −120) were highly demethylated in each SeV-iPS cell clone, while the promoters were highly methylated in the parental BJ and HDF lines as the controls. Thus, the Oct3/4 and Nanog promoters were demonstrated to be activated in SeV-iPS cells as in ES cells (FIG. 9).
(Bisulfite Sequencing Method)

Genomic DNA was extracted from iPS cells using a QIAamp DNA Mini Kit (50) (QIAGEN, catalog No. 51304) according to the protocol appended to the kit. Then, 1 µg of the extracted genomic DNA was modified with bisulfite using a BisulFast DNA Modification Kit for Methylated DNA Detection (Toyobo, catalog No. MDD-101) according to the attached protocol. PCR was carried out using the bisulfite-modified genomic DNA as a template, together with specific primers that target the promoter regions of the Oct3/4 and Nanog genes. The PCR product was separated by agarose gel electrophoresis. The bands of interest were purified using a QIAquick Gel Extraction Kit (QIAGEN, catalog No. 28704). The purified PCR product was TA-cloned using pGEM-T Easy Vector System I (Promega, catalog No. A1360) according to the attached protocol. Then, colony PCR was carried out using specific primers that target the promoter regions of the Oct3/4 and Nanog genes. About ten clones that gave a band of the correct size were selected by agarose gel electrophoresis. Plasmid DNAs were extracted from the clones by mini-prep, and sequenced using the T7 and SP6 primers. Methylation of the promoter regions was assessed by comparing the sequences with the target sequences after bisulfite modification.

PCR primers for amplification of the Oct3/4 gene promoter region and colony PCR (J. Biol. Chem., 2005, Vol. 280, 6257-6260):

```
                                             (SEQ ID NO: 73)
mOct4-5F:    5'-AATAGATTTTGAAGGGGAGTTTAGG-3';
and (SEQ ID NO: 74)
mOct4-5R:    5'-TTCCTCCTTCCTCTAAAAAACTCA-3'
```

PCR primers for amplification of the Nanog gene promoter region and colony PCR (Stem cell Research, Vol. 1, 105-115; Cell, 2007, Vol. 131, 861-72):

```
Nanog-z1-L:
                                             (SEQ ID NO: 75)
5'-GGAATTTAAGGTGTATGTATTTTTTATTTT-3';
and mehNANOG-F1-AS:
                                             (SEQ ID NO: 76)
5'-AACCCACCCTTATAAATTCTCAATTA-3'
```

Sequencing Primers:

```
T7:
5'-TAATACGACTCACTATAGGG-3';      (SEQ ID NO: 77)
and

SP6:
5'-CATACGATTTAGGTGACACTATAG-3'   (SEQ ID NO: 78)
```

Kit Used:
BisulFast DNA Modification Kit for Methylated DNA Detection (Toyobo, catalog No. MDD-101)

Example 10

Gene Expression Analysis of iPS Cells

The gene expression profile of iPS cells induced with the Sendai virus vectors (SeV-iPS cells) was compared to those of the parental BJ cell line, human ES cells, and previously established human iPS cells (GSM241846; Takahashi, K. et al., Cell, 131, 1-12, 2007). Total RNAs were extracted from SeV-iPS and BJ cells using an RNeasy Mini Kit (Qiagen). Cyanine dye-labeled cRNAs were synthesized from cDNAs using a Quick Amp Labeling Kit (Agilent). The cRNAs were hybridized with the Whole Human Genome Oligo Microarray (4×44K) for 17 hours using a Gene Expression Hybridization Kit (Agilent). After washing, the images of the DNA microarray were scanned using an Agilent Microarray Scanner. Fluorescent signal at each spot was digitized and analyzed by Feature Extraction Software (v.9.5.3.1). A total of 41078 probes on the chip, excluding those overlapped, were analyzed (BIO MATRIX RESEARCH). The gene expression in SeV-iPS cells was compared to the gene expression in the following controls, whose information was obtained from GEO DetaSets: human ES cells, hES-H9 (GSM194390; Teser P. J., et al., Nature 448, 196-199, 2007), and human iPS cells, hiPS induced from HDF (GSM241846; Takahashi, K. et al., Cell, 131, 1-12, 2007). The result showed that the correlation of SeV-iPS with BJ was r=8732, with human ES cells was r=0.9658, and with human iPS cells was r=0.9580. The Nanog, Sox2, and Oct3/4 genes, which are expressed in ES cells, were also expressed in SeV-iPS. While there was no correlation with BJ, the profiles of SeV-iPS and human ES cells or human iPS cells were located on the correlation line, and they completely matched (FIG. 9).

Example 11

Preparation of Vectors into Which Temperature-Dependent Inactivation Mutations are Introduced (Method for Preparing Vectors)
Construction of Plasmids for Preparing Sendai Virus Vectors into Which Temperature-Dependent Inactivation Mutations are Introduced PCR was carried out (94° C. for three minutes, and 25 cycles of [98° C. for 10 seconds, 55° C. for 15 seconds, and 72° C. for 11 minutes], followed by 72° C. for seven minutes) using Litmus SalINheIfrg PmutMtsHNts ΔF-GFP (WO2003/025570) as a template, together with the following:
the combination of: L Y942H-F (5'-CAAATGTTGGAG-GATTCAACCACATGTCTACATCTAGATG-3' (SEQ ID NO: 79)) and L Y942H-R (5'-CATCTAGATGTAGACAT-GTGGTTGAATCCTCCAACATTTG-3' (SEQ ID NO: 80)); and
the combination of: L Y942H-F, L Y942H-R, P2-F (5'-CAT-CACAGCTGCAGGTGGCGCGACTGACAAC-3' (SEQ ID NO: 81)), and P2-R (5'-GTTGTCAGTCGCGCCAC-CTGCAGCTGTGATG-3' (SEQ ID NO: 82)). The PCR products were digested with DpnI at 37° C. for one hour. E. coli DH5α (ToYoBo, Code No. DNA-903) was transformed with 20 µl of the reaction mixture. Colonies formed were isolated and mini-prep was performed. Then, clones that have the correct sequences were selected by sequencing, and thus Litmus38TSΔF-GFP-LY942H and Litmus38TSΔF-GFP-P2LY942H were obtained.

Litmus38TSΔF-GFP-P2LY942H was digested with StuI, and then this was separated by agarose gel electrophoresis. A band of 1.9 kbp was excised, and the DNA was purified. Litmus SalINheIfrg PmutMtsHNts ΔF-GFP was digested with StuI, and then this was separated by agarose gel electrophoresis. A band of 9.8 kbp was excised, and the DNA was purified. The two purified fragments were ligated together to construct Litmus38TSΔF-GFP-P2.

Litmus38TSΔF-GFP-P2LY942H was digested with NcoI, and then this was separated by agarose gel electrophoresis. A band of 7.1 kbp was excised, and the DNA was purified. Litmus SalINheIfrg PmutMtsHNts ΔF-GFP delGFP was digested with NcoI, and then this was separated by agarose gel electrophoresis. A band of 3.7 kbp was excised, and the DNA was purified. The purified DNAs were ligated together. The structure of the product was confirmed by colony PCR and double digestion with NcoI and PacI. Thus, Litmus38TSΔF-P2LY942HΔGFP was obtained.

pSeV(HNL)/TSΔF was digested with NcoI, and then this was separated by agarose gel electrophoresis. A band of 3.7 kbp was excised, and the DNA was purified. The resulting fragment was ligated to the above 7.1-kbp NcoI fragment from Litmus38TSΔF-GFP-P2LY942H to prepare Litmus38TSΔF-P2LY942H(HNL)ΔGFP.

Litmus38TSΔF-GFP-P2 was digested with NcoI, and then this was separated by agarose gel electrophoresis. A band of 7.1 kbp was excised, and the DNA was purified. The resulting fragment was ligated to the above NcoI-digested and purified fragment (3.7 kbp) from Litmus SalINheIfrg PmutMtsHNts ΔF-GFP delGFP and NcoI-digested and purified fragment (3.7 kbp) from pSeV(HNL)/TSΔF to construct Litmus38TSΔF-P2ΔGFP and Litmus38TSΔF-P2(HNL)ΔGFP, respectively.

PCR was carried out (94° C. for three minutes, and 25 cycles of 198° C. for 10 seconds, 55° C. for 15 seconds, and 72° C. for nine minutes], followed by 72° C. for 7 minutes) using pSeV/ΔSalINheIfrg Lmut (WO2003/025570) as a template, together with the following:
the combination of: L L1361C-F (5'-GGTTCCTTAGG-GAAGCCATGTATATTGCACTTACATCTTA-3' (SEQ ID NO: 83)) and L L1361C-R (5'-TAAGATGTAAGTG-CAATATACATGGCTTCCCTAAGGAACC-3' (SEQ ID NO: 84));
the combination of: L L1558I-F (5'-CCTGTGTATGGGC-CTAACATCTCAAATCAGGATAAGATAC-3' (SEQ ID NO: 85)) and L L1558I-R (5'-GTATCTTATCCT-GATTTGAGATGTTAGGCCCATACACAGG-3' (SEQ ID NO: 86)); and
the combination of L L1361C-F, L L1361C-R, L L1558I-F, and L L1558I-R. The PCR products were digested with DpnI at 37° C. for one hour. E. coli DH5α (ToYoBo, Code No. DNA-903) was transformed with 20 µl of the reaction mixture. Colonies formed were isolated and mini-prep was performed. Clones that have the correct sequences were selected by sequencing, and thus pSeV/TSΔF-Linker L1361C, pSeV/TSΔF-Linker L1558I, and pSeV/TSΔF-Linker L1361CL1558I were obtained.

Litmus38TSΔF-P2LY942H(HNL)ΔGFP and pSeV/TSΔF-Linker L1361CL1558I were each digested with SalI and NheI, and then the digests were separated by agarose gel electrophoresis. Bands of 8.0 kbp and 8.3 kbp, respectively, were excised, and the DNAs were purified. The purified fragments were ligated together to construct pSeV(HNL)/TS8ΔF.

pSeV(HNL)/TS8ΔF and pSeV(HNL)/TSΔF were digested with NotI and XhoI, and the digests were separated by agarose gel electrophoresis. Bands of 4.9 kbp and 11.4 kbp, respectively, were excised, and the DNAs were purified. The purified fragments were ligated together to construct pSeV (HNL)/TS7ΔF. pBS-KS-c-rMyc was digested with NotI. The resulting NotI fragment containing the c-rMyc gene was excised and purified, and then this was inserted into the NotI site of the pSeV(HNL)/TS7ΔF vector to construct pSeV (HNL)-c-rMyc/TS7ΔF.

Litmus38TSΔF-P2LY942HΔGFP and pSeV/TSΔF-Linker L1361CL1558I were each digested with SalI and NheI, and then the digests were separated by agarose gel electrophoresis. Bands of 8.0 kbp and 8.3 kbp, respectively, were excised, and the DNAs were purified. The purified fragments were ligated together to construct pSeV18+BSSHII/TS8ΔF. pSeV18+BSSHII/TS8ΔF and pSeV18+Oct3/4/TSΔF were each digested with AatII and SphI, and bands of 15.2 kbp and 2.3 kbp, respectively, were excised, and the DNAs were purified. The purified fragments were ligated together to construct pSeV18+Oct3/4/TS8ΔF. pSeV18+Oct3/4/TS8ΔF and pSeV18+/TSΔF were each digested with PadI and SphI, and then the digests were separated by agarose gel electrophoresis. Bands of 13.3 kbp and 4.2 kbp, respectively, were excised, and the DNAs were purified. The purified fragments were ligated together to construct pSeV18+ Oct3/4/TS7ΔF. Then, pSeV18+Oct3/4/TS7ΔF was digested with NotI, and then this was separated by agarose gel electrophoresis. A band of 16.4 kbp was excised, and the DNA was purified. The purified fragment was ligated to the NotI fragments each containing the Sox2, KLF4, or c-rMyc gene, which were excised by NotI digestion from pBS-KS-Sox2, pBS-KS-KLF4, and pBS-KS-c-rMyc described above, respectively, and then purified. Thus, pSeV18+Sox2/TS7ΔF, pSeV18+KLF4/TS7ΔF, and pSeV18+c-rMyc/TS7ΔF were obtained.

Litmus38TSΔF-P2(HNL)ΔGFP and pSeV/TSΔF-Linker L1361C were each digested with SalI and NheI, and then the digests were separated by agarose gel electrophoresis. Bands of 8.0 kbp and 8.3 kbp, respectively, were excised, and the DNAs were purified. The purified fragments were ligated together to construct pSeV (HNL)/TS14ΔF. pBS-KS-c-rMyc was digested with NotI. The resulting NotI fragment containing the c-rMyc gene was excised and purified, and then this was inserted into the NotI site of pSeV(HNL)/TS14ΔF to construct pSeV(HNL)-c-rMyc/TS14ΔF. Litmus38TSΔF-P2 (HNL)ΔGFP and pSeV/TSΔF-Linker L1558I were each digested with SalI and NheI, and then the digests were separated by agarose gel electrophoresis. Bands of 8.0 kbp and 8.3 kbp, respectively, were excised, and the DNAs were purified. The purified fragments were ligated together to construct pSeV(HNL)/TS13ΔF. pBS-KS-c-rMyc was digested with NotI. The resulting NotI fragment containing the c-rMyc gene was excised and purified, and then this was inserted into the NotI site of pSeV(HNL)/TS13ΔF to construct pSeV (HNL)-c-rMyc/TS13ΔF.

Litmus38TSΔF-P2(HNL)ΔGFP and pSeV/TSΔF-Linker L1361CL1558I were each digested with SalI and NheI, and then the digests were separated by agarose gel electrophoresis. Bands of 8.0 kbp and 8.3 kbp, respectively, were excised, and the DNAs were purified. The purified fragments were ligated together to construct pSeV(HNL)/TS15ΔF. pBS-KS-c-rMyc was digested with NotI. The resulting NotI fragment containing the c-rMyc gene was excised and purified, and then this was inserted into the NotI site of pSeV(HNL)/TS15ΔF to construct pSeV(HNL)-c-rMyc/TS15ΔF.

Litmus38TSΔF-P2ΔGFP and pSeV/TSΔF-Linker L1361C were each digested with SalI and NheI, and then the digests were separated by agarose gel electrophoresis. Bands of 8.0 kbp and 8.3 kbp, respectively, were excised, and the DNAs were purified. The purified fragments were ligated together to construct pSeV18+BSSHII/TS14ΔF. pSeV18+BSSHII/TS14ΔF was digested with AatII and SphI, and a band of 15.2 kbp was excised, and the DNA was purified. The purified fragment was ligated to the above AatII-SphI fragment (2.3 kbp) from pSeV18+Oct3/4/TSΔF to construct pSeV18+Oct3/4/TS14ΔF. Then, pSeV18+Oct3/4/TS14ΔF was digested with NotI, and then this was separated by agarose gel electrophoresis. A band of 16.4 kbp was excised, and the DNA was purified. The purified fragment was ligated to the NotI fragments each containing the Sox2, KLF4, or c-rMyc gene, which were excised by NotI digestion from pBS-KS-Sox2, pBS-KS-KLF4, and pBS-KS-c-rMyc described above, respectively, and then purified. Thus, pSeV18+Sox2/TS14ΔF, pSeV18+KLF4/TS14ΔF, and pSeV18+c-rMyc/TS14ΔF were obtained.

Litmus38TSΔF-P2ΔGFP and pSeV/TSΔF-Linker L1558I were each digested with SalI and NheI, and then the digests were separated by agarose gel electrophoresis. Bands of 8.0 kbp and 8.3 kbp, respectively, were excised, and the DNAs were purified. The purified fragments were ligated together to construct pSeV18+BSSHII/TS13ΔF. pSeV18+BSSHII/ TS13ΔF was digested with AatII and SphI, and a band of 15.2 kbp was excised, and the DNA was purified. The purified fragment was ligated to the above AatII-SphI fragment (2.3 kbp) from pSeV18+Oct3/4/TSΔF to construct pSeV18+ Oct3/4/TS13ΔF. Then, pSeV18+Oct3/4/TS13ΔF was digested with NotI, and then this was separated by agarose gel electrophoresis. A band of 16.4 kbp was excised, and the DNA was purified. The purified fragment was ligated to the above NotI fragments each containing the Sox2, KLF4, or c-rMyc gene. Thus, pSeV18+Sox2/TS13ΔF, pSeV18+KLF4/ TS13ΔF, and pSeV18+c-rMyc/TS13ΔF were obtained.

Litmus38TSΔF-P2ΔGFP and pSeV/TSΔF-Linker L1361CL1558I were each digested with SalI and NheI, and then the digests were separated by agarose gel electrophoresis. Bands of 8.0 kbp and 8.3 kbp, respectively, were excised, and the DNAs were purified. The purified fragments were ligated together to construct pSeV18+BSSHII/TS15ΔF. pSeV18+BSSHII/TS15ΔF was digested with AatII and SphI, and a band of 15.2 kbp was excised, and the DNA was purified. The purified fragment was ligated to the above AatII-SphI fragment (2.3 kbp) from pSeV18+Oct3/4/TSΔF to construct pSeV18+Oct3/4/TS15ΔF. Then, pSeV18+Oct3/4/TS15ΔF was digested with NotI, and then this was separated by agarose gel electrophoresis. A band of 16.4 kbp was excised, and the DNA was purified. The purified fragment was ligated to the above NotI fragments each containing the Sox2, KLF4, or c-rMyc gene. Thus, pSeV18+Sox2/TS15ΔF, pSeV18+KLF4/TS15ΔF, and pSeV18+c-rMyc/TS15ΔF were obtained.

Litmus38TSΔF-P2(HNL)ΔGFP and pSeV/ΔSalINheIfrg Lmut were each digested with SalI and NheI, and then the digests were separated by agarose gel electrophoresis. Bands of 8.0 kbp and 8.3 kbp, respectively, were excised, and the DNAs were purified. The purified fragments were ligated together to construct pSeV (HNL)/TS12ΔF. pBS-KS-c-rMyc was digested with NotI. The resulting NotI fragment containing the c-rMyc gene was excised and purified, and then this was inserted into the NotI site of pSeV(HNL)/TS12ΔF to construct pSeV(HNL)-c-rMyc/TS12ΔF. Litmus38TSΔF-P2ΔGFP and pSeV/ΔSalINheIfrg Lmut were each digested with SalI and NheI, and then the digests were separated by agarose gel electrophoresis. Bands of 8.0 kbp and 8.3 kbp, respectively, were excised, and the DNAs were purified. The purified fragments were ligated together to construct pSeV18+BSSHII/TS12ΔF. pSeV18+BSSHII/TS12ΔF was digested with AatII and SphI, and a band of 15.2 kbp was excised, and the DNA was purified. The purified fragment was ligated to the above AatII-SphI fragment (2.3 kbp) from pSeV18+Oct3/4/TSΔF to construct pSeV18+Oct3/4/ TS12ΔF. Then, pSeV18+Oct3/4/TS12ΔF was digested with NotI, and then this was separated by agarose gel electrophoresis. A band of 16.4 kbp was excised, and the DNA was purified. The purified fragment was ligated to the above NotI fragments each containing the Sox2, KLF4, or c-rMyc gene. Thus, pSeV18+Sox2/TS12ΔF, pSeV18+KLF4/TS12ΔF, and pSeV18+c-rMyc/TS12ΔF were obtained.

(Collection of F Gene-Deficient Sendai Virus Vectors into Which Temperature-Dependent Inactivation Mutations are Introduced)

On the previous day of transfection, $10^6$ 293T/17 cells were seeded into each well of a 6-well plate, and cultured in a $CO_2$ incubator (5% $CO_2$) at 37° C. Using 15 μl of TransIT-LT1 (Mirus), the 293T/17 cells were transfected with a mixture of: 0.5 μg of pCAGGS-NP, 0.5 μg of pCAGGS-P4C (−), 2 μg of pCAGGS-L (TDK), 0.5 μg of pCAGGS-T7, 0.5 μg of pCAGGS-F5R (WO2005/071085), and 0.5 μg of the above F gene-deficient Sendai virus vector plasmid into which temperature-dependent inactivation mutants are introduced, and that carries a human transcriptional factor. The cells were cultured in a $CO_2$ incubator at 37° C. for two to three days. Then, $10^6$ LLC-MK2/F/A cells which express the fusion protein (F protein) of Sendai virus were overlaid onto the transfected 293T/17 cells in each well, and the cells were cultured in a $CO_2$ incubator at 37° C. for one day. On the following day, the cell culture medium was removed, and the cells were washed once with 1 ml of MEM supplemented with penicillin-streptomycin (hereinafter abbreviated as PS/MEM). 1 ml of PS/MEM containing 2.5 µ/ml trypsin (hereinafter abbreviated as Try/PS/MEM) was added to each well. The cells were cultured in a $CO_2$ incubator at 32° C. The cells were continuously cultured while exchanging the medium every three to four days, and in some cases, passaging with LLC-MK2/F/A cells. An aliquot of the culture supernatant was assessed for vector collection by hemagglutination assay. The culture supernatant was harvested after sufficient hemagglutination was observed. RNA was extracted from the harvested culture supernatant using a QIAamp Viral RNA Mini Kit (QIAGEN, catalog No. 52906), and subjected to RT-PCR that targets a region of the inserted gene. Whether the obtained RT-PCR product has the correct nucleotide sequence was confirmed by sequencing. Thus, F gene-deficient Sendai virus vectors into which temperature-dependent inactivation mutations are introduced, and which carry various human transcriptional factors, were obtained.

Example 12

Vector Removal

Colonies in which a SeV vector was naturally removed from SeV-iPS cells, were obtained. Furthermore, Sendai virus-free clones were obtained by temperature shift to 39° C. after induction of iPS at 37° C. using the temperature-sensitive vectors. SeV-free clones were also obtained by negative selection with an anti-HN antibody using as an indicator the HN antigen, which is expressed on the cell surface upon SeV infection.

1. Natural Removal

Figure 10:
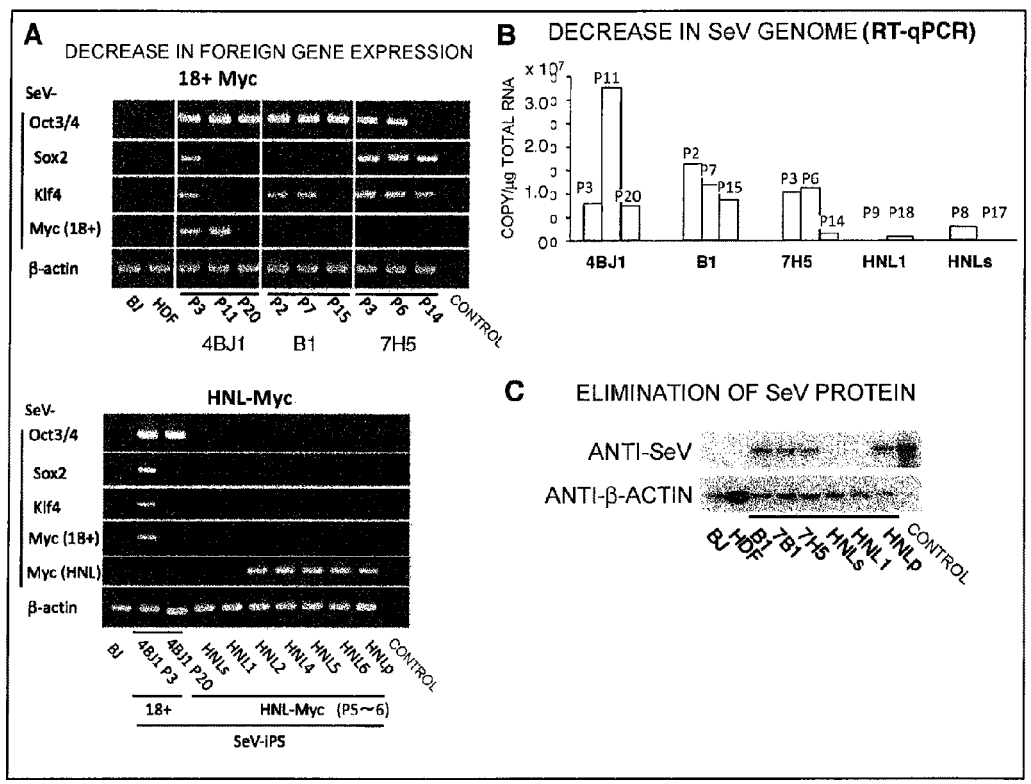
FIG. 10 shows elimination of the introduced foreign genes and Sendai virus (SeV) vectors through cell proliferation. This is a figure showing that the introduced foreign genes and Sendai virus (SeV) vectors become diluted/eliminated as the cells proliferate. (A) Decrease in expression of the introduced foreign genes in SeV-iPS cells derived from neonatal cells (BJ) or from adult cells (HDF) (BJ-derived clones using 18+c-Myc: 4BJ1, B1; HDF-derived clone: 7H5; BJ-derived clones using HNL-c-Myc: HNLs, HNL1 to 6, HNLp) were measured over time by RT-PCR using primers recognizing the sequence of the vector portion (P refers to the passage number). As the passage progressed, the four introduced reprogramming factors decreased to three and then to two. The tendency observed was that when the foreign gene was introduced to position 18+, c-Myc was deleted first, and when c-Myc was introduced to position HNL, c-Myc remained until the end, and combinations among the four vectors were suggested to have certain replicative advantages. Furthermore, clones HNLs and HNL1 induced with HNL-c-Myc were completely free of foreign genes. (B) Decrease of the SeV genome in iPS cells over time. In a manner similar to A, decrease in the SeV genome over time in each of the iPS cell clones was measured by quantitative RT-PCR. As a result, decrease of the SeV genome as the passage progressed was confirmed by quantitative PCR as well, and disappearance of the SeV genome in the HNL1 and HNLs clones was made clear. (C) Elimination of the SeV protein in iPS cells. Elimination of the SeV-derived gene in HNL1 and HNLs observed in A and B was observed in Western blotting using anti-SeV antibodies as well, and not only the genome but also the SeV-derived protein was confirmed to be eliminated.

Passage culture of SeV-iPS cells led to an increase in the number of cells from which the vectors were naturally removed. RNA was extracted from cells of the SeV-iPS colonies. RT-PCR was carried out to assess the expression of foreign genes derived from SeV. When SeV-Oct3/4, Sox2, Klf4, and c-Myc (c-rMyc or c-Myc) were inserted at position 18+ (the 3' end of the NP gene that is located at the most 3' end of the genome) (SeV18+Oct3/4/TSΔF, SeV18+Sox2/TSΔF, SeV18+Klf4/TSΔF, and SeV18+c-Myc/TSΔF (or SeV18+c-rMyc/TSΔF), respectively), the foreign genes were diluted via cell division, and often, only one or two of the genes remained to be expressed. Wild-type c-Myc was eliminated first due to its lower replicability. On the other hand, when c-rMyc was inserted at the position of HNL (HNL-c-rMyc/ TSΔF), the cells often retained the Myc gene-carrying vector alone due to its higher replicability than the vectors into which a factor of interest was inserted at position 18+. Even clones from which all of the introduced foreign reprogramming factors were completely removed were obtained. The complete removal was demonstrated not only by RT-PCR but also at the protein level by Western blotting using an anti-SeV-NP antibody (FIG. 10). The RT-PCR primers used are as described in Example 6.

2. Removal with an Anti-HN Antibody

Figure 11:
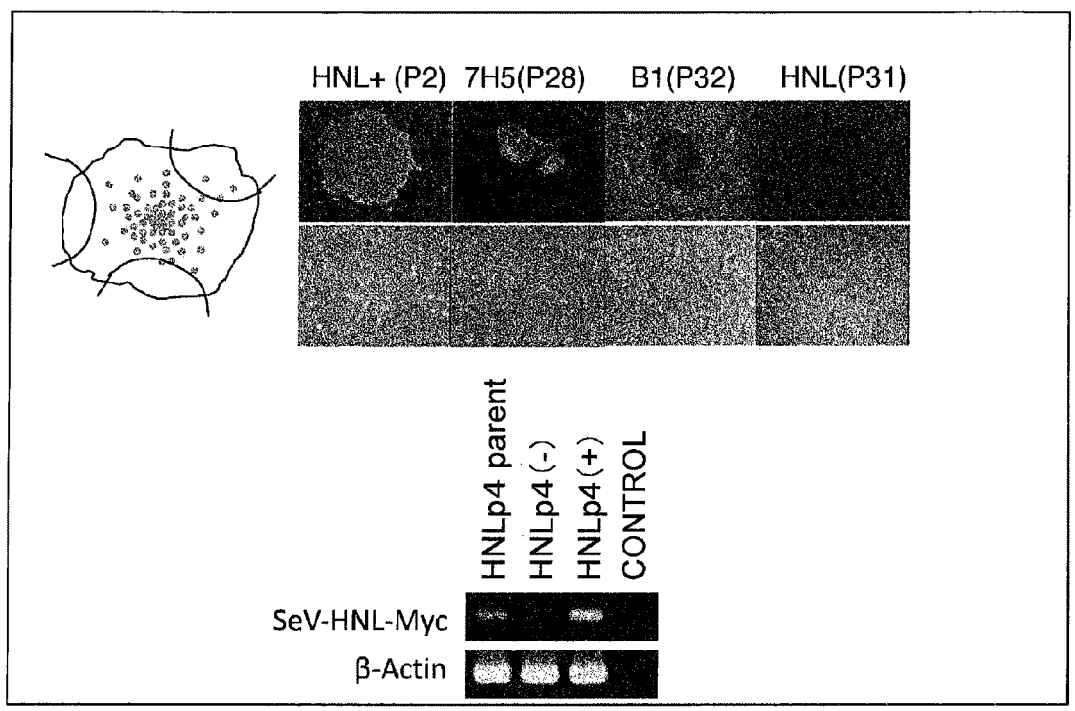
FIG. 11 shows collection of virus vector-negative cell population using anti-virus protein antibodies. (Top panels) Virus vector dilution in the iPS colonies is shown. Staining of SeV-iPS cell colonies using anti-FIN antibodies suggested that SeV-positive cells and SeV-negative cells coexist in the colonies, and as shown in the schematic diagram on the left, by selecting a portion with few virus particles, negative population can be collected (P: passage number). (Lower panels) It was actually possible to remove SeV-positive cells using anti-HN antibodies by using HN antigens that appear on the surface of SeV-infected cells as indicators. The SeV-iPS cell population (cell line in which c-Myc/SeV remains: NHLp4 parent) was reacted with the anti-HN antibodies, this was bound to IMag (BD) magnet beads, the negative fraction was collected, and RT-PCR was used to confirm that this is SeV negative (HNL4p−). It was also possible to concentrate the SeV-positive population (HNL4p+).

SeV vectors are naturally removed by dilution via cell division and passaging. Alternatively, SeV vector-free cells can be actively collected. Utilizing an anti-HN antibody, SeV vector-removed cells can be obtained using as an indicator the HN antigen, which is expressed on the cell surface upon SeV infection. Cells were disaggregated into small populations by collagenase IV and trypsin treatment and suspension procedure. The cells were reacted with the anti-HN monoclonal antibody IL4.1 on ice for 30 minutes. After washing with medium, the cells were reacted with a secondary antibody, for example, an anti-mouse IgG1 antibody bound to magnetic beads (Anti-Mouse IgG1 Particles; BD) on ice for 30 minutes. The unbound fraction was collected using a magnet (IMagnet Cell Separation Magnet; BD) (negative selection). Thus, a cell population with impaired SeV vector expression was obtained. Vector-free iPS cells were isolated by repeating the above treatments (FIG. 11). Alternatively, an anti-HN antibody-negative cell population can be isolated by FACS.

3. Temperature-Sensitive Vector-Based Technique for SeV Removal

TS 7: L (Y942H/L1361C/L1558I)
TS 13: P (D433A/R434A/K437A), L (L1558I)
TS 14: P (D433A/R434A/K437A), L (L1361C)
TS 15: P (D433A/R434A/K437A), L (L1361C/L1558I)

The above mutations were introduced into the SeV18+/TSΔF vector. The resulting vectors are temperature-sensitive, and their replication is inhibited by temperature shift. Specifically, an inserted gene is expressed at the highest level at 32° C., and also expressed at 35 to 36° C., and expressed at a slightly lower level at 37° C., but not expressed at 38.5 or 39° C.

The reprogramming factors were inserted into these vectors in the same manner as described above. iPS cells were induced at 37° C., and the temperature was shifted after production of the iPS cells, and SeV could be readily removed from the cells.

4. Higher Replicability of HNL-Myc

Figure 12:
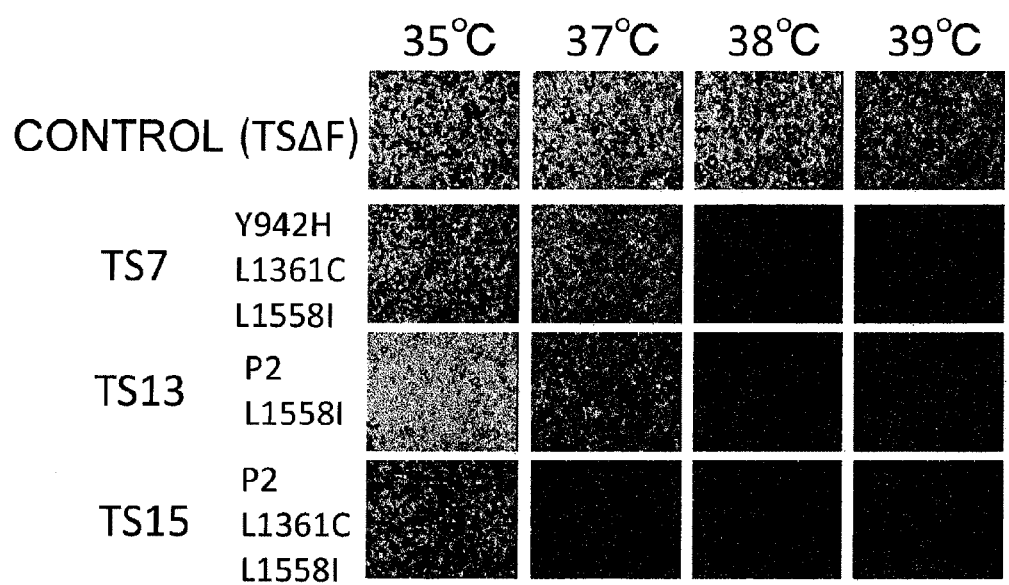
FIG. 12 shows the properties of the new temperature-sensitive strains. The TS strain used in Example 1 has low cytotoxicity at 37° C., but expression of the carried GFP protein showed relatively little change even when the temperature was shifted from 35° C. to 39° C. (control TS/ΔF). However, the newly constructed TS7 (Y942H, L1361C, and L15581) did not show GFP expression at 38° C. or higher, TS13 (P2, L15581) showed lower expression at 37° C. than at 35° C., and TS15 (P2, L1361C, L15581) showed hardly any GFP expression at 37° C.
Figure 13:
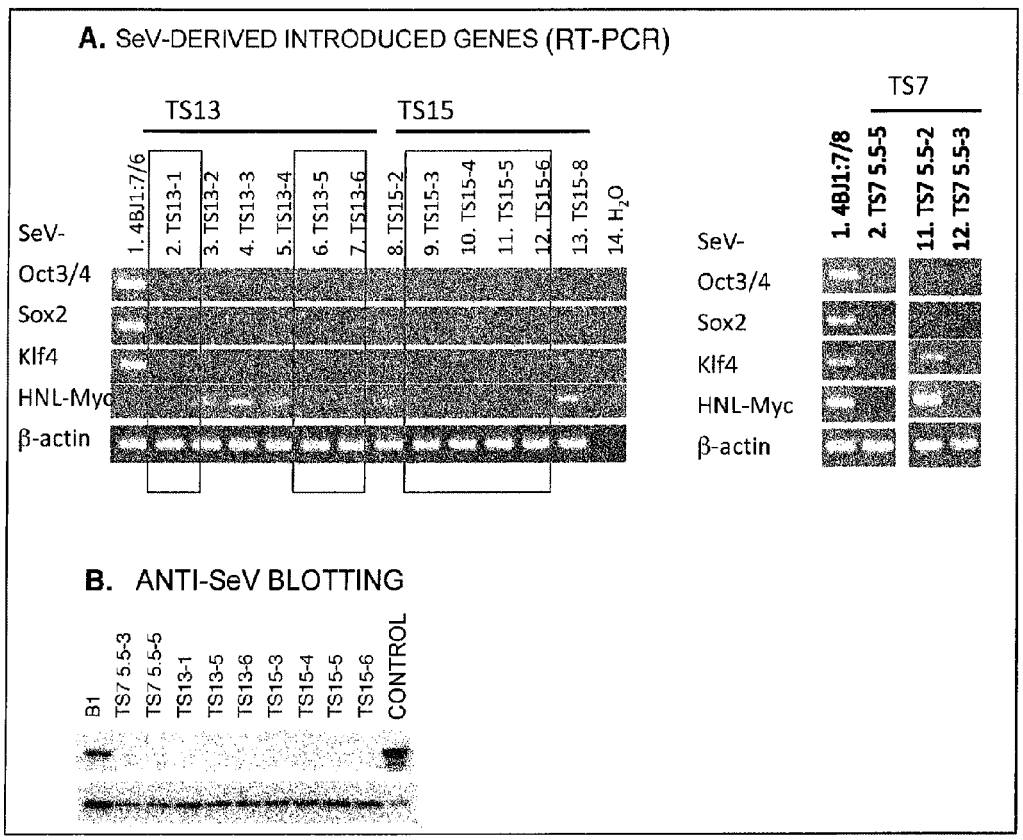
FIG. 13 shows human iPS cell induction using the temperature-sensitive strains TS7, TS13, and TS15/ΔF/SeV and virus removal. A. ΔF/TS/SeV carrying c-Myc at the HNL position (between the HN gene and the L gene) of TS7, TS13, or TS15, and ΔF/TS/SeV carrying Oct3/4, Sox2, and KLF4 installed in TS were infected simultaneously into neonatal foreskin cells BJ to induce human iPS cells. A. Half or more of the isolated iPS cells became free of foreign genes as a result of RT-PCR. B. When the SeV protein in the iPS cell clones free of foreign genes was checked, the clones were completely virus-free at the protein level as well. (4BJ1 and B1: SeV-expressing iPS cells; control: SeV-infected LLC-MK2 cells).

As described in section 1, when SeV-18+Oct3/4, Klf4, Sox2, and SeV-HNL-c-rMyc were used in combination to induce iPS, SeV-HNL-c-rMyc in which the c-rMyc gene is inserted between HN and L was more advantageous in replication than the SeV vectors carrying the other factors inserted at position 18+ (upstream of the NP gene). Furthermore, since c-Myc is beneficial for cell growth, of the four factors inserted into SeV, only SeV-HNL-c-rMyc was finally retained. SeV-iPS cells induced with SeV-HNL-c-rMyc were easily established as clones because they have superior proliferation ability. In addition, only one vector was retained, and it tended to be naturally removed. Thus, only the vector for HNL-c-rMyc needs to be temperature-sensitive to achieve the removal by temperature shift using temperature-sensitive strains. In fact, the HNL-c-rMyc vector finally remained could be removed by temperature shift (FIGS. 12 and 13).

Figure 14:
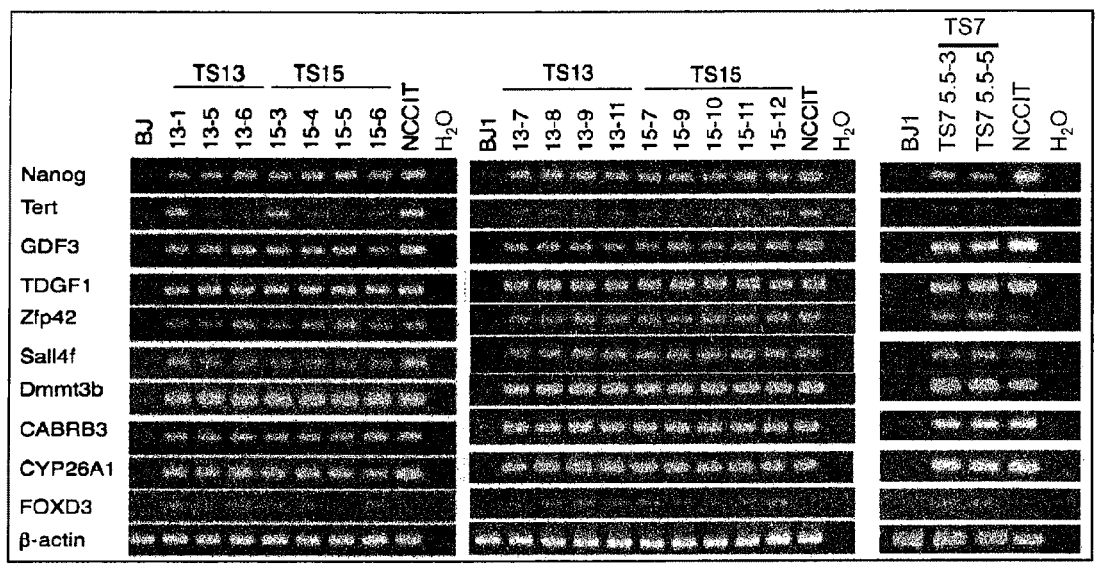
FIG. 14 shows ES marker expression of human iPS cells induced by temperature-sensitive strains TS7, TS13, and TS15/ΔF/SeV. Expression of ES markers was verified by RT-PCR for iPS cell clones confirmed to be foreign genes and virus-free in the experiment indicated in FIG. 13. In all of the virus-free iPS cells, expression of all of the investigated ES markers was confirmed.

5. Preparation of iPS Cells from Which Temperature-Sensitive SeV Vectors are Readily Removable When iPS cells are induced from fibroblasts (BJ cells) using the TS vectors each having Oct3/4, Klf4, or Sox2 as an insert at position 18+ and the above-described vector (TS7ΔF, TS13ΔF, or TS15ΔF) having the c-rMyc gene as an insert between HN and L of TS7, TS13, or TS15, only the temperature-sensitive SeV-HNL-Myc is retained because of its superior replicability as described above. Furthermore, when the cells have SeV-HNL-Myc alone, the last vector retained is rapidly eliminated, because the expression level of the temperature-sensitive strain is lower at 37° C.

iPS was thus induced. The number of clones that became SeV vector-free within one month after induction was four out of six when using TS/18+Oct3/4, Sox2, Klf4/TSΔF, and TS13ΔF/HNL-c-rMyc in combination; three out of six when using TS/18+Oct3/4, Sox2, Klf4/TSΔF, and TS15ΔF/HNL-c-rMyc in combination; and two out of twelve when using TS/18+ Oct3/4, Sox2, Klf4/TSΔF, and TS7ΔF/HNL-c-rMyc in combination (FIG. 13). All of the obtained SeV-free clones expressed the human ES cell-specific markers (FIG. 14).

This method allows simple preparation of SeV-free and intact iPS cells without damaging the chromosome.

Example 13

As described in section 5 of Example 12, iPS cells can be induced using not only the above-described TSΔF vectors but also TS7ΔF, TS13ΔF, and TS15ΔF into which the reprogramming factors (Oct3/4, Sox2, Klf4, and c-Myc) are inserted. Using an L mutant (Y1214F) with another ΔF vector backbone (WO2008/096811), whether iPS cells can also be induced in the same manner was tested as follows.
(Construction of LmΔF/SeV)
Plasmid Construction pSeV 18+LacZ/ΔF-1214 (WO2008/096811) was digested with NotI, and this was purified. Then, the resulting fragment was ligated, and a plasmid without the lacZ gene was selected. Thus, pSeV18+/ΔF-1214 (also referred to as "Lm (Y1214F) ΔF/SeV", or simply, "LmΔF/SeV") was obtained.

Next, pSeV18+/ΔF-1214 was digested with NotI, and this was purified.

The above-mentioned NotI fragments of the four reprogramming factors Oct3/4, Klf4, Sox2, and c-rMyc were each inserted into the above vector to construct the plasmids pSeV18+Oct3/4/ΔF-1214, pSeV18+Sox2/ΔF-1214, pSeV18+KLF4/ΔF-1214, and pSeV18+c-rMyc/ΔF-1214 for preparation of viral vectors.
Collection of LmΔF/SeV Sendai Virus Vectors On the previous day of transfection, $10^6$ 293T/17 cells were seeded into each well of a 6-well plate, and cultured in a $CO_2$ incubator (5% $CO_2$) at 37° C. Using 15 µl of TransIT-LT1 (Mirus), the 293T/17 cells were transfected with a mixture of: 0.5 µg of pCAGGS-NP, 0.5 µg of pCAGGS-P4C(-), 2 µg of pCAGGS-L (TDK), 0.5 µg of pCAGGS-T7, 0.5 µg of pCAGGS-F5R (WO2005/071085), and 0.5 µg of an LmΔF/SeV Sendai virus vector plasmid carrying an above-described human transcriptional factor. The cells were cultured in a $CO_2$ incubator at 37° C. for two to three days. Then, $10^6$ LLC-MK2/F/A cells which express the fusion protein (F protein) of Sendai virus were overlaid onto the transfected 293T/17 cells in each well, and the cells were cultured in a $CO_2$ incubator at 37° C. for one day. On the following day, the cell culture medium was removed, and the cells were washed once with 1 ml of MEM supplemented with penicillin-streptomycin (hereinafter abbreviated as PS/MEM). 1 ml of PS/MEM containing 2.5 µg/ml trypsin (hereinafter abbreviated as Try/PS/MEM) was added to each well. The cells were cultured in a $CO_2$ incubator at 32° C. The cells were continuously cultured while exchanging the medium every three to four days, and in some cases, passaging with LLC-MK2/F/A cells. An aliquot of the culture supernatant was assessed for vector collection by hemagglutination assay. The culture supernatant was harvested after sufficient hemagglutination was observed. RNA was extracted from the harvested culture supernatant using a QIAamp Viral RNA Mini Kit (QIAGEN catalog No. 52906), and subjected to RT-PCR that targets a region of the inserted gene. Whether the RT-PCR product has the correct nucleotide sequence was confirmed by sequencing. Thus, LmΔF/SeV Sendai virus vectors carrying various human transcriptional factors were obtained.

Figure 15:
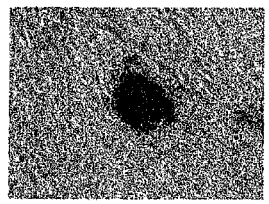
FIG. 15 shows SeV-iPS cells induced by other SeV vectors or reprogramming factors. (A) When iPS cell induction was performed by installing Oct3/4, Sox2, Oct4, and Nanog onto Lm(Y1214F) ΔF/SeV, which has a different vector backbone from TS ΔF/SeV used in Example 1, alkaline phosphatase (ALP)-positive ES-like cell colonies were obtained. (B) iPS cell induction by the four Thomson factors (Oct3/4, Sox2, Nanog, Lin28 ΔF/TS/SeV). iPS cells were induced by factors other than the four Yamanaka factors (Oct3/4, Sox2, Klf4, c-Myc) (left panel), which are the four Thomson factors (Oct3/4, Sox2, Nanog, Lin28 ΔF/TS/SeV) (right panel).
Figure 15:
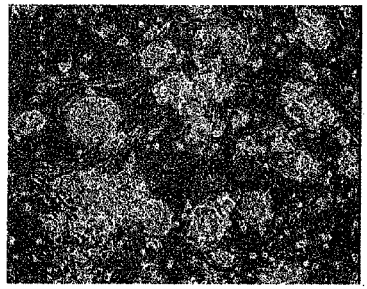
Figure 15:
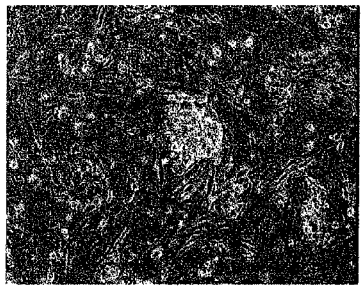

The four reprogramming factors Oct3/4, Klf4, Sox2, and c-rMyc (TSΔF) were inserted into LmΔF/SeV at position 18+ in the same manner to construct viral vectors.

iPS cells were induced from human fibroblast BJ cells by infecting them with LmΔF/SeV carrying the four factors in the same way as with the TSΔF SeV vectors. As a result, iPS-like colonies were formed in the same manner as when using TSΔF/SeV, and the cells expressed ALP which is an ES marker (FIG. 15A). This indicates that iPS can be induced using not only one type of vector backbone, but also other Sendai virus vector backbones.

Example 14

Method for Inducing iPS without Feeder Cells

Because the Sendai virus vectors express the reprogramming factors at high levels, iPS can be induced without feeder cells instead of using the conventional method of induction on feeder cells. Cells were infected with SeV carrying the reprogramming factors, and induced without feeder in plastic dishes for 15 days after infection. When iPS-like colonies were formed, the culture medium was changed from DMEM/10% FBS to an ES cell medium. After the colonies became sufficiently large, the cells were detached from the dishes using collagenase IV, and then plated onto fresh feeder cells. Thus, iPS cells could be established.

Example 15 iPS Induction Using Thomson's Four Factors (Oct3/4, Sox2, Lin28, and Nanog)

iPS cells could also be induced from human fibroblasts by using TSΔF/SeV carrying Thomson's four factors (Oct3/4, Sox2, Lin28, and Nanog) (Yu J et al., Science. 2007, 318 (5858):1917-20), instead of Yamanaka's four factors (Oct3/4, Sox2, Klf4, and c-Myc) (Takahashi, K. and Yamanaka S., Cell 126, 663-676, 2006) (FIG. 15B). An example of construction of Nanog and Lin28 vectors is described below.
(1) Isolation of the Human Transcriptional Factor Nanog, Construction of a Sendai Virus Vector Plasmid Carrying Nanog, and Preparation of a Sendai Virus Vector Carrying Nanog A cDNA library of NCCIT cells was subjected to PCR using PrimeStar™ HS DNA polymerase (Takara Bio, catalog No. R010A) and the following primers: NANOF-F (5'-CCACCATGAGTGTGGATCCAGCTTGTCC-3' (SEQ ID NO: 87)) and NANOF-R (5'-CTCACACGTCTTCAGGT-TGCATGTTC-3' (SEQ ID NO: 88)). The PCR product was purified using a Qiaquick PCR Purification kit (QIAGEN, catalog No. 28106), and this was cloned into the EcoRV site of a Bluescript plasmid vector. The gene sequence was determined by sequencing. A clone that has the correct sequence was selected, and thus pBS-KS-Nanog was obtained.

Then, PCR was carried out using pBS-KS-Nanog as a template, together with the following primers: NotI-Nanog-F (5'-GCGCGGCCGCACCACCATGAGTGTG-GATCCAGCTTGTCC-3' (SEQ ID NO: 89)) and NotI-Nanog-R (5'-GCGCGGCCGCGATGAACTTTCAC-CCTAAGTTTTTCTTACTACGGTCACACGTCTTC AGGTTGCATGTTCATGGAGTAGTTTAG-3' (SEQ ID NO: 90)). The PCR product was purified using a Qiaquick PCR Purification kit (QIAGEN, catalog No. 28106), and then this was digested with NotI. The digest was purified using a Qiaquick PCR Purification kit (QIAGEN, catalog No. 28106), and this was cloned into the NotI site of the pSeV18+/

TSΔF vector. A clone that has the correct sequence was selected by sequencing, and thus pSeV18+Nanog/TSΔF was obtained. Using this plasmid, an F gene-deficient Sendai virus vector carrying the Nanog gene (hereinafter referred to as "SeV18+ Nanog/TSΔF vector") was prepared by the above-described method.

(2) Isolation of Human Lin28, Construction of a Sendai Virus Vector Plasmid Carrying Nanog, and Construction of a Sendai Virus Vector Carrying Lin28

A cDNA library of NCCIT cells was subjected to PCR using PrimeStar™ HS DNA polymerase (Takara Bio, catalog No. R010A) and the following primers: LIN28-F (5'-CCAC-CATGGGCTCCGTGTCCAACCAGC-3' (SEQ ID NO: 91)) and LIN28-R (5'-GTCAATTCTGTGCCTCCGGGAGC-3' (SEQ ID NO: 92)). The PCR product was purified using a Qiaquick PCR Purification kit (QIAGEN, catalog No. 28106), and this was cloned into the EcoRV site of a Bluescript plasmid vector. The gene sequence was determined by sequencing. A clone that has the correct sequence was selected, and thus pBS-KS-Lin28 was obtained. Then, PCR was carried out using pBS-KS-Lin28 as a template, together with the following primers: NotI-Lin28-F (5'-GCGCGGC-CGCACCACCATGGGCTCCGTGTCCAACCAGC-3' (SEQ ID NO: 93)) and NotI-Lin28-R (5'-GCGCGGCCGC-GATGAACTTTCACCCTAAGTTTTTCT-TACTACGGTCAATTCTGTGCCT CCGGGAGCAGGG-TAGGGCTGTG-3' (SEQ ID NO: 94)). The PCR product was purified using a Qiaquick PCR Purification kit (QIAGEN, catalog No. 28106), and then this was digested with NotI. The digest was purified using a Qiaquick PCR Purification kit (QIAGEN, catalog No. 28106), and this was cloned into the NotI site of the pSeV18+/TSΔF vector. A clone that has the correct sequence was selected by sequencing, and thus pSeV18+Lin 28/TSΔF was obtained. Using this plasmid, an F gene-deficient Sendai virus vector carrying the Lin28 gene (herein referred to as "SeV18+Lin 28/TSΔF vector") was prepared by the above-described method.

INDUSTRIAL APPLICABILITY

The present invention allows production of ES-like cells (pluripotent stem cells) without integrating genes into the chromosome of host cells. Since no foreign gene is integrated into the chromosome of the produced cells, they are advantageous in tests and research. Furthermore, it is expected that immunological rejection and ethical problems in disease treatments, as well as the risk of tumorigenesis due to genetic toxicity can be avoided.

The invention claimed is:

1. A method of producing an induced pluripotent stem cell (iPSC), comprising introducing one or more Sendai virus vectors encoding at least Oct3/4 and Sox2 into a differentiated cell, and culturing said cell under conditions to obtain a reprogrammed iPSC.

2. The method of claim 1, wherein said one or more Sendai virus vectors encodes at least Oct3/4, Klf4, and Sox2, or at least Oct3/4, Sox2, Nanog, and Lin28.

3. The method of claim 1, wherein said one or more Sendai virus vectors encodes at least Oct3/4, Klf4, Sox2, and c-Myc, or at least Oct3/4, Klf4, Sox2, and L-Myc.

4. The method of claim 1, wherein said one or more Sendai virus vectors are temperature sensitive Sendai virus vectors, and wherein said method further comprises removing said one or more Sendai virus vectors by culturing the cell at 37.5° C. to 39° C. after reprogramming.

* * * * *

UNITED STATES PATENT AND TRADEMARK OFFICE
CERTIFICATE OF CORRECTION

PATENT NO. : 9,127,256 B2  
APPLICATION NO. : 13/054022  
DATED : September 8, 2015  
INVENTOR(S) : Fusaki et al.

Page 1 of 2

It is certified that error appears in the above-identified patent and that said Letters Patent is hereby corrected as shown below:

In the specification

Column 7, Line 49, replace "clone 7115" with --clone 7H5--.

Column 8, Line 28, replace "anti-FIN" with --anti-HN--.

Column 8, Line 47, replace "L15581" with --L1558I--.

Column 8, Line 49, replace "L15581" with --L1558I--.

Column 8, Line 50, replace "L15581" with --L1558I--.

Column 12, Line 33, replace "HPIV-3" with --BPIV-3--.

Column 13, Line 6, replace "detective" with --defective--.

Column 15, Line 37, replace "(or II)" with --(or H)--.

Column 24, Line 33, replace "7% (WN)" with --7% (W/V)--.

Column 27, Line 67, replace "Liao Jet al" with --Liao J et al--.

Column 28, Line 20, replace "NC" with --NM--.

Column 29, Line 11, replace "(SAIIA)" with --(SAHA)--.

Column 30, Line 8, replace "IIanna J." with --Hanna J.--.

Column 31, Line 60, replace "(SEQ 1D NO: 3))" with --(SEQ ID NO: 3))--.

Column 34, Line 58, replace "TransIT" with --TransIT--.

Column 38, Line 40, replace "Pad" with --PacI--.

Signed and Sealed this  
Eighth Day of March, 2016

Michelle K. Lee  
*Director of the United States Patent and Trademark Office*

CERTIFICATE OF CORRECTION (continued)
U.S. Pat. No. 9,127,256 B2

In the specification

Column 46, Line 14, replace "198°C" with --[98°C--.

Column 48, Line 62, replace "TranslT" with --TransIT--.

Column 51, Line 37, replace "TranslT" with --TransIT--.

SEQUENCE LISTING

```
<160> NUMBER OF SEQ ID NOS: 94

<210> SEQ ID NO 1
<211> LENGTH: 21
<212> TYPE: DNA
<213> ORGANISM: Artificial
<220> FEATURE:
<223> OTHER INFORMATION: an artificially synthesized primer

<400> SEQUENCE: 1
aaccagcagc ctcccgcgac g                                              21

<210> SEQ ID NO 2
<211> LENGTH: 25
<212> TYPE: DNA
<213> ORGANISM: Artificial
<220> FEATURE:
<223> OTHER INFORMATION: an artificially synthesized primer

<400> SEQUENCE: 2
aggacatttc tgttagaagg aatcg                                          25

<210> SEQ ID NO 3
<211> LENGTH: 25
<212> TYPE: DNA
<213> ORGANISM: Artificial
<220> FEATURE:
<223> OTHER INFORMATION: an artificially synthesized primer

<400> SEQUENCE: 3
gatgcccctc aacgttagct tcacc                                          25

<210> SEQ ID NO 4
<211> LENGTH: 25
<212> TYPE: DNA
<213> ORGANISM: Artificial
<220> FEATURE:
<223> OTHER INFORMATION: an artificially synthesized primer

<400> SEQUENCE: 4
```

```
gttacgcaca agagttccgt agctg                                              25

<210> SEQ ID NO 5
<211> LENGTH: 34
<212> TYPE: DNA
<213> ORGANISM: Artificial
<220> FEATURE:
<223> OTHER INFORMATION: an artificially synthesized primer

<400> SEQUENCE: 5
attgcggccg catgcccctc aacgttagct tcac                                    34

<210> SEQ ID NO 6
<211> LENGTH: 85
<212> TYPE: DNA
<213> ORGANISM: Artificial
<220> FEATURE:
<223> OTHER INFORMATION: an artificially synthesized primer

<400> SEQUENCE: 6
attgcggccg cgatgaactt tcaccctaag tttttcttac tacggttacg cacaagagtt        60
ccgtagctgt tcaagtttgt gtttc                                              85

<210> SEQ ID NO 7
<211> LENGTH: 27
<212> TYPE: DNA
<213> ORGANISM: Artificial
<220> FEATURE:
<223> OTHER INFORMATION: an artificially synthesized primer

<400> SEQUENCE: 7
caaagtcccg gccgggccga gggtcgg                                            27

<210> SEQ ID NO 8
<211> LENGTH: 23
<212> TYPE: DNA
<213> ORGANISM: Artificial
<220> FEATURE:
<223> OTHER INFORMATION: an artificially synthesized primer

<400> SEQUENCE: 8
ccctccagtt cgctgtccgg ccc                                                23

<210> SEQ ID NO 9
<211> LENGTH: 26
<212> TYPE: DNA
<213> ORGANISM: Artificial
<220> FEATURE:
<223> OTHER INFORMATION: an artificially synthesized primer

<400> SEQUENCE: 9
gatgtacaac atgatggaga cggagc                                             26

<210> SEQ ID NO 10
<211> LENGTH: 24
<212> TYPE: DNA
<213> ORGANISM: Artificial
<220> FEATURE:
<223> OTHER INFORMATION: an artificially synthesized primer

<400> SEQUENCE: 10
gtcacatgtg tgagaggggc agtg                                               24

<210> SEQ ID NO 11
<211> LENGTH: 32
```

```
<212> TYPE: DNA
<213> ORGANISM: Artificial
<220> FEATURE:
<223> OTHER INFORMATION: an artificially synthesized primer

<400> SEQUENCE: 11
attgcggccg catgtacaac atgatggaga cg                                    32

<210> SEQ ID NO 12
<211> LENGTH: 85
<212> TYPE: DNA
<213> ORGANISM: Artificial
<220> FEATURE:
<223> OTHER INFORMATION: an artificially synthesized primer

<400> SEQUENCE: 12
attgcggccg cgatgaactt tcaccctaag tttttcttac tacggtcaca tgtgtgagag      60
gggcagtgtg ccgttaatgg ccgtg                                            85

<210> SEQ ID NO 13
<211> LENGTH: 26
<212> TYPE: DNA
<213> ORGANISM: Artificial
<220> FEATURE:
<223> OTHER INFORMATION: an artificially synthesized primer

<400> SEQUENCE: 13
ccacattaat gaggcagcca cctggc                                           26

<210> SEQ ID NO 14
<211> LENGTH: 26
<212> TYPE: DNA
<213> ORGANISM: Artificial
<220> FEATURE:
<223> OTHER INFORMATION: an artificially synthesized primer

<400> SEQUENCE: 14
gcagtgtggg tcatatccac tgtctg                                           26

<210> SEQ ID NO 15
<211> LENGTH: 27
<212> TYPE: DNA
<213> ORGANISM: Artificial
<220> FEATURE:
<223> OTHER INFORMATION: an artificially synthesized primer

<400> SEQUENCE: 15
gatggctgtc agcgacgcgc tgctccc                                          27

<210> SEQ ID NO 16
<211> LENGTH: 31
<212> TYPE: DNA
<213> ORGANISM: Artificial
<220> FEATURE:
<223> OTHER INFORMATION: an artificially synthesized primer

<400> SEQUENCE: 16
gttaaaaatg cctcttcatg tgtaaggcga g                                     31

<210> SEQ ID NO 17
<211> LENGTH: 35
<212> TYPE: DNA
<213> ORGANISM: Artificial
<220> FEATURE:
<223> OTHER INFORMATION: an artificially synthesized primer
```

<400> SEQUENCE: 17
attgcggccg cgacatggct gtcagcgacg cgctg    35

<210> SEQ ID NO 18
<211> LENGTH: 81
<212> TYPE: DNA
<213> ORGANISM: Artificial
<220> FEATURE:
<223> OTHER INFORMATION: an artificially synthesized primer

<400> SEQUENCE: 18
attgcggccg cgatgaactt tcaccctaag tttttcttac tacggttaaa aatgcctctt    60
catgtgtaag gcgaggtggt c    81

<210> SEQ ID NO 19
<211> LENGTH: 26
<212> TYPE: DNA
<213> ORGANISM: Artificial
<220> FEATURE:
<223> OTHER INFORMATION: an artificially synthesized primer

<400> SEQUENCE: 19
caccatgctt ggggcgcctt ccttcc    26

<210> SEQ ID NO 20
<211> LENGTH: 25
<212> TYPE: DNA
<213> ORGANISM: Artificial
<220> FEATURE:
<223> OTHER INFORMATION: an artificially synthesized primer

<400> SEQUENCE: 20
catcggagtt gctctccacc ccgac    25

<210> SEQ ID NO 21
<211> LENGTH: 21
<212> TYPE: DNA
<213> ORGANISM: Artificial
<220> FEATURE:
<223> OTHER INFORMATION: an artificially synthesized primer

<400> SEQUENCE: 21
cccgccgtat gagttctgtg g    21

<210> SEQ ID NO 22
<211> LENGTH: 42
<212> TYPE: DNA
<213> ORGANISM: Artificial
<220> FEATURE:
<223> OTHER INFORMATION: an artificially synthesized primer

<400> SEQUENCE: 22
gccgcggccg cgttatcagt ttgaatgcat gggagagccc ag    42

<210> SEQ ID NO 23
<211> LENGTH: 34
<212> TYPE: DNA
<213> ORGANISM: Artificial
<220> FEATURE:
<223> OTHER INFORMATION: an artificially synthesized primer

<400> SEQUENCE: 23
gccgcggccg caccatggcg ggacacctgg cttc    34

```
<210> SEQ ID NO 24
<211> LENGTH: 81
<212> TYPE: DNA
<213> ORGANISM: Artificial
<220> FEATURE:
<223> OTHER INFORMATION: an artificially synthesized primer

<400> SEQUENCE: 24
gccgcggccg cgatgaactt tcaccctaag tttttcttac tacggtcagt ttgaatgcat    60
gggagagccc agagtggtga c                                              81

<210> SEQ ID NO 25
<211> LENGTH: 21
<212> TYPE: DNA
<213> ORGANISM: Artificial
<220> FEATURE:
<223> OTHER INFORMATION: an artificially synthesized primer

<400> SEQUENCE: 25
gatcctcgga cctggctaag c                                              21

<210> SEQ ID NO 26
<211> LENGTH: 23
<212> TYPE: DNA
<213> ORGANISM: Artificial
<220> FEATURE:
<223> OTHER INFORMATION: an artificially synthesized primer

<400> SEQUENCE: 26
gctccagctt ctccttctcc agc                                            23

<210> SEQ ID NO 27
<211> LENGTH: 23
<212> TYPE: DNA
<213> ORGANISM: Artificial
<220> FEATURE:
<223> OTHER INFORMATION: an artificially synthesized primer

<400> SEQUENCE: 27
agcgctgcac atgaaggagc acc                                            23

<210> SEQ ID NO 28
<211> LENGTH: 27
<212> TYPE: DNA
<213> ORGANISM: Artificial
<220> FEATURE:
<223> OTHER INFORMATION: an artificially synthesized primer

<400> SEQUENCE: 28
atgcgctggt tcacgcccgc gcccagg                                        27

<210> SEQ ID NO 29
<211> LENGTH: 21
<212> TYPE: DNA
<213> ORGANISM: Artificial
<220> FEATURE:
<223> OTHER INFORMATION: an artificially synthesized primer

<400> SEQUENCE: 29
gctgcacacg acttccccct g                                              21

<210> SEQ ID NO 30
<211> LENGTH: 25
<212> TYPE: DNA
<213> ORGANISM: Artificial
<220> FEATURE:
```

<223> OTHER INFORMATION: an artificially synthesized primer

<400> SEQUENCE: 30
ggggatggaa gccgggagga agcgg                                    25

<210> SEQ ID NO 31
<211> LENGTH: 20
<212> TYPE: DNA
<213> ORGANISM: Artificial
<220> FEATURE:
<223> OTHER INFORMATION: an artificially synthesized primer

<400> SEQUENCE: 31
tctcaacgac agcagctcgc                                          20

<210> SEQ ID NO 32
<211> LENGTH: 25
<212> TYPE: DNA
<213> ORGANISM: Artificial
<220> FEATURE:
<223> OTHER INFORMATION: an artificially synthesized primer

<400> SEQUENCE: 32
caggagcctg cctctttttcc acaga                                   25

<210> SEQ ID NO 33
<211> LENGTH: 20
<212> TYPE: DNA
<213> ORGANISM: Artificial
<220> FEATURE:
<223> OTHER INFORMATION: an artificially synthesized primer

<400> SEQUENCE: 33
tacctcagcc tccagcagat                                          20

<210> SEQ ID NO 34
<211> LENGTH: 20
<212> TYPE: DNA
<213> ORGANISM: Artificial
<220> FEATURE:
<223> OTHER INFORMATION: an artificially synthesized primer

<400> SEQUENCE: 34
tgcgtcacac cattgctatt                                          20

<210> SEQ ID NO 35
<211> LENGTH: 18
<212> TYPE: DNA
<213> ORGANISM: Artificial
<220> FEATURE:
<223> OTHER INFORMATION: an artificially synthesized primer

<400> SEQUENCE: 35
caaccgcgag aagatgac                                            18

<210> SEQ ID NO 36
<211> LENGTH: 18
<212> TYPE: DNA
<213> ORGANISM: Artificial
<220> FEATURE:
<223> OTHER INFORMATION: an artificially synthesized primer

<400> SEQUENCE: 36
aggaaggctg gaagagtg                                            18

```
<210> SEQ ID NO 37
<211> LENGTH: 24
<212> TYPE: DNA
<213> ORGANISM: Artificial
<220> FEATURE:
<223> OTHER INFORMATION: an artificially synthesized primer

<400> SEQUENCE: 37
tgcccggacc tccatcagag ccag                                           24

<210> SEQ ID NO 38
<211> LENGTH: 26
<212> TYPE: DNA
<213> ORGANISM: Artificial
<220> FEATURE:
<223> OTHER INFORMATION: an artificially synthesized primer

<400> SEQUENCE: 38
tcagtccagg atggtcttga agtctg                                         26

<210> SEQ ID NO 39
<211> LENGTH: 43
<212> TYPE: DNA
<213> ORGANISM: Artificial
<220> FEATURE:
<223> OTHER INFORMATION: an artificially synthesized primer

<400> SEQUENCE: 39
cggacgacga gaccttcatc aagaacatca tcatccagga ctg                      43

<210> SEQ ID NO 40
<211> LENGTH: 43
<212> TYPE: DNA
<213> ORGANISM: Artificial
<220> FEATURE:
<223> OTHER INFORMATION: an artificially synthesized primer

<400> SEQUENCE: 40
cagtcctgga tgatgatgtt cttgatgaag gtctcgtcgt ccg                      43

<210> SEQ ID NO 41
<211> LENGTH: 44
<212> TYPE: DNA
<213> ORGANISM: Artificial
<220> FEATURE:
<223> OTHER INFORMATION: an artificially synthesized primer

<400> SEQUENCE: 41
gaacgagcta aaacggagct tcttcgccct gcgtgaccag atcc                     44

<210> SEQ ID NO 42
<211> LENGTH: 44
<212> TYPE: DNA
<213> ORGANISM: Artificial
<220> FEATURE:
<223> OTHER INFORMATION: an artificially synthesized primer

<400> SEQUENCE: 42
ggatctggtc acgcagggcg aagaagctcc gttttagctc gttc                     44

<210> SEQ ID NO 43
<211> LENGTH: 44
<212> TYPE: DNA
<213> ORGANISM: Artificial
<220> FEATURE:
<223> OTHER INFORMATION: an artificially synthesized primer
```

-continued

<400> SEQUENCE: 43
cccaaggtag ttatccttaa gaaggccaca gcatacatcc tgtc                          44

<210> SEQ ID NO 44
<211> LENGTH: 44
<212> TYPE: DNA
<213> ORGANISM: Artificial
<220> FEATURE:
<223> OTHER INFORMATION: an artificially synthesized primer

<400> SEQUENCE: 44
gacaggatgt atgctgtggc cttcttaagg ataactacct tggg                          44

<210> SEQ ID NO 45
<211> LENGTH: 1317
<212> TYPE: DNA
<213> ORGANISM: Artificial
<220> FEATURE:
<223> OTHER INFORMATION: a silent mutant human c-myc (a378g, t1122c,
      t1125c, a1191g, and a1194g)
<220> FEATURE:
<221> NAME/KEY: CDS
<222> LOCATION: (1)..(1317)

<400> SEQUENCE: 45

```
atg ccc ctc aac gtt agc ttc acc aac agg aac tat gac ctc gac tac        48
Met Pro Leu Asn Val Ser Phe Thr Asn Arg Asn Tyr Asp Leu Asp Tyr
1               5                   10                  15 gac tcg gtg cag ccg tat ttc tac tgc gac gag gag gag aac ttc tac        96
Asp Ser Val Gln Pro Tyr Phe Tyr Cys Asp Glu Glu Glu Asn Phe Tyr
            20                  25                  30 cag cag cag cag cag agc gag ctg cag ccc ccg gcg ccc agc gag gat       144
Gln Gln Gln Gln Gln Ser Glu Leu Gln Pro Pro Ala Pro Ser Glu Asp
        35                  40                  45 atc tgg aag aaa ttc gag ctg ctg ccc acc ccg ccc ctg tcc cct agc       192
Ile Trp Lys Lys Phe Glu Leu Leu Pro Thr Pro Pro Leu Ser Pro Ser
    50                  55                  60 cgc cgc tcc ggg ctc tgc tcg ccc tcc tac gtt gcg gtc aca ccc ttc       240
Arg Arg Ser Gly Leu Cys Ser Pro Ser Tyr Val Ala Val Thr Pro Phe
65                  70                  75                  80 tcc ctt cgg gga gac aac gac ggc ggt ggc ggg agc ttc tcc acg gcc       288
Ser Leu Arg Gly Asp Asn Asp Gly Gly Gly Gly Ser Phe Ser Thr Ala
                85                  90                  95 gac cag ctg gag atg gtg acc gag ctg ctg gga gga gac atg gtg aac       336
Asp Gln Leu Glu Met Val Thr Glu Leu Leu Gly Gly Asp Met Val Asn
            100                 105                 110 cag agt ttc atc tgc gac ccg gac gac gag acc ttc atc aag aac atc       384
Gln Ser Phe Ile Cys Asp Pro Asp Asp Glu Thr Phe Ile Lys Asn Ile
        115                 120                 125 atc atc cag gac tgt atg tgg agc ggc ttc tcg gcc gcc gcc aag ctc       432
Ile Ile Gln Asp Cys Met Trp Ser Gly Phe Ser Ala Ala Ala Lys Leu
    130                 135                 140 gtc tca gag aag ctg gcc tcc tac cag gct gcg cgc aaa gac agc ggc       480
Val Ser Glu Lys Leu Ala Ser Tyr Gln Ala Ala Arg Lys Asp Ser Gly
145                 150                 155                 160 agc ccg aac ccc gcc cgc ggc cac agc gtc tgc tcc acc tcc agc ttg       528
Ser Pro Asn Pro Ala Arg Gly His Ser Val Cys Ser Thr Ser Ser Leu
                165                 170                 175 tac ctg cag gat ctg agc gcc gcc gcc tca gag tgc atc gac ccc tcg       576
Tyr Leu Gln Asp Leu Ser Ala Ala Ala Ser Glu Cys Ile Asp Pro Ser
            180                 185                 190 gtg gtc ttc ccc tac cct ctc aac gac agc agc tcg ccc aag tcc tgc       624
Val Val Phe Pro Tyr Pro Leu Asn Asp Ser Ser Ser Pro Lys Ser Cys
```

```
            Val Val Phe Pro Tyr Pro Leu Asn Asp Ser Ser Ser Pro Lys Ser Cys
                195                 200                 205 gcc tcg caa gac tcc agc gcc ttc tct ccg tcc tcg gat tct ctg ctc        672
Ala Ser Gln Asp Ser Ser Ala Phe Ser Pro Ser Ser Asp Ser Leu Leu
210                 215                 220 tcc tcg acg gag tcc tcc ccg cag ggc agc ccc gag ccc ctg gtg ctc        720
Ser Ser Thr Glu Ser Ser Pro Gln Gly Ser Pro Glu Pro Leu Val Leu
225                 230                 235                 240 cat gag gag aca ccg ccc acc acc agc agc gac tct gag gag gaa caa        768
His Glu Glu Thr Pro Pro Thr Thr Ser Ser Asp Ser Glu Glu Glu Gln
                245                 250                 255 gaa gat gag gaa gaa atc gat gtt gtt tct gtg gaa aag agg cag gct        816
Glu Asp Glu Glu Glu Ile Asp Val Val Ser Val Glu Lys Arg Gln Ala
            260                 265                 270 cct ggc aaa agg tca gag tct gga tca cct tct gct gga ggc cac agc        864
Pro Gly Lys Arg Ser Glu Ser Gly Ser Pro Ser Ala Gly Gly His Ser
        275                 280                 285 aaa cct cct cac agc cca ctg gtc ctc aag agg tgc cac gtc tcc aca        912
Lys Pro Pro His Ser Pro Leu Val Leu Lys Arg Cys His Val Ser Thr
290                 295                 300 cat cag cac aac tac gca gcg cct ccc tcc act cgg aag gac tat cct        960
His Gln His Asn Tyr Ala Ala Pro Pro Ser Thr Arg Lys Asp Tyr Pro
305                 310                 315                 320 gct gcc aag agg gtc aag ttg gac agt gtc aga gtc ctg aga cag atc       1008
Ala Ala Lys Arg Val Lys Leu Asp Ser Val Arg Val Leu Arg Gln Ile
                325                 330                 335 agc aac aac cga aaa tgc acc agc ccc agg tcc tcg gac acc gag gag       1056
Ser Asn Asn Arg Lys Cys Thr Ser Pro Arg Ser Ser Asp Thr Glu Glu
            340                 345                 350 aat gtc aag agg cga aca cac aac gtc ttg gag cgc cag agg agg aac       1104
Asn Val Lys Arg Arg Thr His Asn Val Leu Glu Arg Gln Arg Arg Asn
        355                 360                 365 gag cta aaa cgg agc ttc ttc gcc ctg cgt gac cag atc ccg gag ttg       1152
Glu Leu Lys Arg Ser Phe Phe Ala Leu Arg Asp Gln Ile Pro Glu Leu
370                 375                 380 gaa aac aat gaa aag gcc ccc aag gta gtt atc ctt aag aag gcc aca       1200
Glu Asn Asn Glu Lys Ala Pro Lys Val Val Ile Leu Lys Lys Ala Thr
385                 390                 395                 400 gca tac atc ctg tcc gtc caa gca gag gag caa aag ctc att tct gaa       1248
Ala Tyr Ile Leu Ser Val Gln Ala Glu Glu Gln Lys Leu Ile Ser Glu
                405                 410                 415 gag gac ttg ttg cgg aaa cga cga gaa cag ttg aaa cac aaa ctt gaa       1296
Glu Asp Leu Leu Arg Lys Arg Arg Glu Gln Leu Lys His Lys Leu Glu
            420                 425                 430 cag cta cgg aac tct tgt gcg                                           1317
Gln Leu Arg Asn Ser Cys Ala
        435

<210> SEQ ID NO 46
<211> LENGTH: 439
<212> TYPE: PRT
<213> ORGANISM: Artificial
<220> FEATURE:
<223> OTHER INFORMATION: Synthetic Construct

<400> SEQUENCE: 46

Met Pro Leu Asn Val Ser Phe Thr Asn Arg Asn Tyr Asp Leu Asp Tyr
1               5                   10                  15

Asp Ser Val Gln Pro Tyr Phe Tyr Cys Asp Glu Glu Glu Asn Phe Tyr
            20                  25                  30
```

```
Gln Gln Gln Gln Ser Glu Leu Gln Pro Pro Ala Pro Ser Glu Asp
        35                  40                  45

Ile Trp Lys Lys Phe Glu Leu Leu Pro Thr Pro Pro Leu Ser Pro Ser
 50                  55                  60

Arg Arg Ser Gly Leu Cys Ser Pro Ser Tyr Val Ala Val Thr Pro Phe
 65                  70                  75                  80

Ser Leu Arg Gly Asp Asn Asp Gly Gly Gly Ser Phe Ser Thr Ala
                 85                  90                  95

Asp Gln Leu Glu Met Val Thr Glu Leu Leu Gly Gly Asp Met Val Asn
            100                 105                 110

Gln Ser Phe Ile Cys Asp Pro Asp Asp Glu Thr Phe Ile Lys Asn Ile
            115                 120                 125

Ile Ile Gln Asp Cys Met Trp Ser Gly Phe Ser Ala Ala Lys Leu
130                 135                 140

Val Ser Glu Lys Leu Ala Ser Tyr Gln Ala Ala Arg Lys Asp Ser Gly
145                 150                 155                 160

Ser Pro Asn Pro Ala Arg Gly His Ser Val Cys Ser Thr Ser Ser Leu
                165                 170                 175

Tyr Leu Gln Asp Leu Ser Ala Ala Ala Ser Glu Cys Ile Asp Pro Ser
            180                 185                 190

Val Val Phe Pro Tyr Pro Leu Asn Asp Ser Ser Ser Pro Lys Ser Cys
            195                 200                 205

Ala Ser Gln Asp Ser Ser Ala Phe Ser Pro Ser Ser Asp Ser Leu Leu
            210                 215                 220

Ser Ser Thr Glu Ser Ser Pro Gln Gly Ser Pro Glu Pro Leu Val Leu
225                 230                 235                 240

His Glu Glu Thr Pro Pro Thr Thr Ser Asp Ser Glu Glu Gln
                245                 250                 255

Glu Asp Glu Glu Glu Ile Asp Val Val Ser Val Glu Lys Arg Gln Ala
            260                 265                 270

Pro Gly Lys Arg Ser Glu Ser Gly Ser Pro Ser Ala Gly Gly His Ser
            275                 280                 285

Lys Pro Pro His Ser Pro Leu Val Leu Lys Arg Cys His Val Ser Thr
290                 295                 300

His Gln His Asn Tyr Ala Ala Pro Pro Ser Thr Arg Lys Asp Tyr Pro
305                 310                 315                 320

Ala Ala Lys Arg Val Lys Leu Asp Ser Val Arg Val Leu Arg Gln Ile
                325                 330                 335

Ser Asn Asn Arg Lys Cys Thr Ser Pro Arg Ser Ser Asp Thr Glu Glu
                340                 345                 350

Asn Val Lys Arg Arg Thr His Asn Val Leu Glu Arg Gln Arg Asn
                355                 360                 365

Glu Leu Lys Arg Ser Phe Phe Ala Leu Arg Asp Gln Ile Pro Glu Leu
            370                 375                 380

Glu Asn Asn Glu Lys Ala Pro Lys Val Val Ile Leu Lys Lys Ala Thr
385                 390                 395                 400

Ala Tyr Ile Leu Ser Val Gln Ala Glu Glu Gln Lys Leu Ile Ser Glu
                405                 410                 415

Glu Asp Leu Leu Arg Lys Arg Arg Glu Gln Leu Lys His Lys Leu Glu
            420                 425                 430

Gln Leu Arg Asn Ser Cys Ala
            435
```

```
<210> SEQ ID NO 47
<211> LENGTH: 49
<212> TYPE: DNA
<213> ORGANISM: Artificial
<220> FEATURE:
<223> OTHER INFORMATION: an artificially synthesized primer

<400> SEQUENCE: 47
gaggtcgcgc gttaattaag ctttcacctc aaacaagcac agatcatgg            49

<210> SEQ ID NO 48
<211> LENGTH: 48
<212> TYPE: DNA
<213> ORGANISM: Artificial
<220> FEATURE:
<223> OTHER INFORMATION: an artificially synthesized primer

<400> SEQUENCE: 48
gcatgtttcc caaggggaga gttaattaac caagcactca caagggac             48

<210> SEQ ID NO 49
<211> LENGTH: 35
<212> TYPE: DNA
<213> ORGANISM: Artificial
<220> FEATURE:
<223> OTHER INFORMATION: an artificially synthesized primer

<400> SEQUENCE: 49
gggtgaatgg gaagcggccg ctaggtcatg gatgg                           35

<210> SEQ ID NO 50
<211> LENGTH: 35
<212> TYPE: DNA
<213> ORGANISM: Artificial
<220> FEATURE:
<223> OTHER INFORMATION: an artificially synthesized primer

<400> SEQUENCE: 50
ccatccatga cctagcggcc gcttcccatt caccc                           35

<210> SEQ ID NO 51
<211> LENGTH: 22
<212> TYPE: DNA
<213> ORGANISM: Artificial
<220> FEATURE:
<223> OTHER INFORMATION: an artificially synthesized primer

<400> SEQUENCE: 51
ggcgtccgcg ggaatgtact tc                                         22

<210> SEQ ID NO 52
<211> LENGTH: 21
<212> TYPE: DNA
<213> ORGANISM: Artificial
<220> FEATURE:
<223> OTHER INFORMATION: an artificially synthesized primer

<400> SEQUENCE: 52
tggcttaggg gtggtctggc c                                          21

<210> SEQ ID NO 53
<211> LENGTH: 24
<212> TYPE: DNA
<213> ORGANISM: Artificial
<220> FEATURE:
<223> OTHER INFORMATION: an artificially synthesized primer
```

```
<400> SEQUENCE: 53
atggactgca ggaagatggc ccgc                                              24

<210> SEQ ID NO 54
<211> LENGTH: 26
<212> TYPE: DNA
<213> ORGANISM: Artificial
<220> FEATURE:
<223> OTHER INFORMATION: an artificially synthesized primer

<400> SEQUENCE: 54
ttaatagtag ctttgtatag aaaggc                                            26

<210> SEQ ID NO 55
<211> LENGTH: 30
<212> TYPE: DNA
<213> ORGANISM: Artificial
<220> FEATURE:
<223> OTHER INFORMATION: an artificially synthesized primer

<400> SEQUENCE: 55
atgagccagc aactgaagaa acgggcaaag                                        30

<210> SEQ ID NO 56
<211> LENGTH: 29
<212> TYPE: DNA
<213> ORGANISM: Artificial
<220> FEATURE:
<223> OTHER INFORMATION: an artificially synthesized primer

<400> SEQUENCE: 56
ctactttccc tcttgttcat tcttgttcg                                         29

<210> SEQ ID NO 57
<211> LENGTH: 20
<212> TYPE: DNA
<213> ORGANISM: Artificial
<220> FEATURE:
<223> OTHER INFORMATION: an artificially synthesized primer

<400> SEQUENCE: 57 aaacccccagc acatcaactc                                                  20

<210> SEQ ID NO 58
<211> LENGTH: 19
<212> TYPE: DNA
<213> ORGANISM: Artificial
<220> FEATURE:
<223> OTHER INFORMATION: an artificially synthesized primer

<400> SEQUENCE: 58
gtcattccct gggtggttc                                                    19

<210> SEQ ID NO 59
<211> LENGTH: 21
<212> TYPE: DNA
<213> ORGANISM: Artificial
<220> FEATURE:
<223> OTHER INFORMATION: an artificially synthesized primer

<400> SEQUENCE: 59
gcagcgacca gtcctccgac t                                                 21

<210> SEQ ID NO 60
<211> LENGTH: 20
```

<212> TYPE: DNA
<213> ORGANISM: Artificial
<220> FEATURE:
<223> OTHER INFORMATION: an artificially synthesized primer

<400> SEQUENCE: 60
aacgtgggga aggcctgtgc                                          20

<210> SEQ ID NO 61
<211> LENGTH: 20
<212> TYPE: DNA
<213> ORGANISM: Artificial
<220> FEATURE:
<223> OTHER INFORMATION: an artificially synthesized primer

<400> SEQUENCE: 61
cttgacaatc gagtggctga                                          20

<210> SEQ ID NO 62
<211> LENGTH: 20
<212> TYPE: DNA
<213> ORGANISM: Artificial
<220> FEATURE:
<223> OTHER INFORMATION: an artificially synthesized primer

<400> SEQUENCE: 62
tcatccgtgg tgtagccata                                          20

<210> SEQ ID NO 63
<211> LENGTH: 22
<212> TYPE: DNA
<213> ORGANISM: Artificial
<220> FEATURE:
<223> OTHER INFORMATION: an artificially synthesized primer

<400> SEQUENCE: 63
aacctgcacg actcctcgca ca                                       22

<210> SEQ ID NO 64
<211> LENGTH: 20
<212> TYPE: DNA
<213> ORGANISM: Artificial
<220> FEATURE:
<223> OTHER INFORMATION: an artificially synthesized primer

<400> SEQUENCE: 64
aggatgcgca tggcgattcg                                          20

<210> SEQ ID NO 65
<211> LENGTH: 21
<212> TYPE: DNA
<213> ORGANISM: Artificial
<220> FEATURE:
<223> OTHER INFORMATION: an artificially synthesized primer

<400> SEQUENCE: 65
gtgaagccgc cttactcgta c                                        21

<210> SEQ ID NO 66
<211> LENGTH: 20
<212> TYPE: DNA
<213> ORGANISM: Artificial
<220> FEATURE:
<223> OTHER INFORMATION: an artificially synthesized primer

<400> SEQUENCE: 66
ccgaagctct gcatcatgag                                              20

<210> SEQ ID NO 67
<211> LENGTH: 22
<212> TYPE: DNA
<213> ORGANISM: Artificial
<220> FEATURE:
<223> OTHER INFORMATION: an artificially synthesized primer

<400> SEQUENCE: 67
acaagagaaa aaacatgtat gg                                           22

<210> SEQ ID NO 68
<211> LENGTH: 23
<212> TYPE: DNA
<213> ORGANISM: Artificial
<220> FEATURE:
<223> OTHER INFORMATION: an artificially synthesized primer

<400> SEQUENCE: 68
gagaggtctc caagccgcct tgg                                          23

<210> SEQ ID NO 69
<211> LENGTH: 20
<212> TYPE: DNA
<213> ORGANISM: Artificial
<220> FEATURE:
<223> OTHER INFORMATION: an artificially synthesized primer

<400> SEQUENCE: 69
aatgtatcga aggtgctcaa                                              20

<210> SEQ ID NO 70
<211> LENGTH: 25
<212> TYPE: DNA
<213> ORGANISM: Artificial
<220> FEATURE:
<223> OTHER INFORMATION: an artificially synthesized primer

<400> SEQUENCE: 70
cgcgctggca gggccgctgc tcgac                                        25

<210> SEQ ID NO 71
<211> LENGTH: 26
<212> TYPE: DNA
<213> ORGANISM: Artificial
<220> FEATURE:
<223> OTHER INFORMATION: an artificially synthesized primer

<400> SEQUENCE: 71
tccacataca gtcctggatg atgatg                                       26

<210> SEQ ID NO 72
<211> LENGTH: 22
<212> TYPE: DNA
<213> ORGANISM: Artificial
<220> FEATURE:
<223> OTHER INFORMATION: an artificially synthesized primer

<400> SEQUENCE: 72
taactgacta gcaggcttgt cg                                           22

<210> SEQ ID NO 73
<211> LENGTH: 25
<212> TYPE: DNA
<213> ORGANISM: Artificial

```
<220> FEATURE:
<223> OTHER INFORMATION: an artificially synthesized sequence

<400> SEQUENCE: 73
aatagatttt gaagggagt ttagg                                              25

<210> SEQ ID NO 74
<211> LENGTH: 24
<212> TYPE: DNA
<213> ORGANISM: Artificial
<220> FEATURE:
<223> OTHER INFORMATION: an artificially synthesized sequence

<400> SEQUENCE: 74
ttcctccttc ctctaaaaaa ctca                                              24

<210> SEQ ID NO 75
<211> LENGTH: 30
<212> TYPE: DNA
<213> ORGANISM: Artificial
<220> FEATURE:
<223> OTHER INFORMATION: an artificially synthesized sequence

<400> SEQUENCE: 75
ggaatttaag gtgtatgtat tttttatttt                                        30

<210> SEQ ID NO 76
<211> LENGTH: 26
<212> TYPE: DNA
<213> ORGANISM: Artificial
<220> FEATURE:
<223> OTHER INFORMATION: an artificially synthesized sequence

<400> SEQUENCE: 76
aacccaccct tataaattct caatta                                            26

<210> SEQ ID NO 77
<211> LENGTH: 20
<212> TYPE: DNA
<213> ORGANISM: Artificial
<220> FEATURE:
<223> OTHER INFORMATION: an artificially synthesized sequence

<400> SEQUENCE: 77
taatacgact cactataggg                                                   20

<210> SEQ ID NO 78
<211> LENGTH: 24
<212> TYPE: DNA
<213> ORGANISM: Artificial
<220> FEATURE:
<223> OTHER INFORMATION: an artificially synthesized sequence

<400> SEQUENCE: 78
catacgattt aggtgacact atag                                              24

<210> SEQ ID NO 79
<211> LENGTH: 40
<212> TYPE: DNA
<213> ORGANISM: Artificial
<220> FEATURE:
<223> OTHER INFORMATION: an artificially synthesized sequence

<400> SEQUENCE: 79
caaatgttgg aggattcaac cacatgtcta catctagatg                             40
```

<210> SEQ ID NO 80
<211> LENGTH: 40
<212> TYPE: DNA
<213> ORGANISM: Artificial
<220> FEATURE:
<223> OTHER INFORMATION: an artificially synthesized sequence

<400> SEQUENCE: 80
catctagatg tagacatgtg gttgaatcct ccaacatttg                40

<210> SEQ ID NO 81
<211> LENGTH: 31
<212> TYPE: DNA
<213> ORGANISM: Artificial
<220> FEATURE:
<223> OTHER INFORMATION: an artificially synthesized sequence

<400> SEQUENCE: 81
catcacagct gcaggtggcg cgactgacaa c                         31

<210> SEQ ID NO 82
<211> LENGTH: 31
<212> TYPE: DNA
<213> ORGANISM: Artificial
<220> FEATURE:
<223> OTHER INFORMATION: an artificially synthesized sequence

<400> SEQUENCE: 82
gttgtcagtc gcgccacctg cagctgtgat g                         31

<210> SEQ ID NO 83
<211> LENGTH: 40
<212> TYPE: DNA
<213> ORGANISM: Artificial
<220> FEATURE:
<223> OTHER INFORMATION: an artificially synthesized sequence

<400> SEQUENCE: 83
ggttccttag ggaagccatg tatattgcac ttacatctta                40

<210> SEQ ID NO 84
<211> LENGTH: 40
<212> TYPE: DNA
<213> ORGANISM: Artificial
<220> FEATURE:
<223> OTHER INFORMATION: an artificially synthesized sequence

<400> SEQUENCE: 84
taagatgtaa gtgcaatata catggcttcc ctaaggaacc                40

<210> SEQ ID NO 85
<211> LENGTH: 40
<212> TYPE: DNA
<213> ORGANISM: Artificial
<220> FEATURE:
<223> OTHER INFORMATION: an artificially synthesized sequence

<400> SEQUENCE: 85
cctgtgtatg ggcctaacat ctcaaatcag gataagatac                40

<210> SEQ ID NO 86
<211> LENGTH: 40
<212> TYPE: DNA
<213> ORGANISM: Artificial
<220> FEATURE:
<223> OTHER INFORMATION: an artificially synthesized sequence

<400> SEQUENCE: 86
gtatcttatc ctgatttgag atgttaggcc catacacagg                              40

<210> SEQ ID NO 87
<211> LENGTH: 28
<212> TYPE: DNA
<213> ORGANISM: Artificial
<220> FEATURE:
<223> OTHER INFORMATION: an artificially synthesized sequence

<400> SEQUENCE: 87
ccaccatgag tgtggatcca gcttgtcc                                           28

<210> SEQ ID NO 88
<211> LENGTH: 26
<212> TYPE: DNA
<213> ORGANISM: Artificial
<220> FEATURE:
<223> OTHER INFORMATION: an artificially synthesized sequence

<400> SEQUENCE: 88
ctcacacgtc ttcaggttgc atgttc                                             26

<210> SEQ ID NO 89
<211> LENGTH: 39
<212> TYPE: DNA
<213> ORGANISM: Artificial
<220> FEATURE:
<223> OTHER INFORMATION: an artificially synthesized sequence

<400> SEQUENCE: 89
gcgcggccgc accaccatga gtgtggatcc agcttgtcc                               39

<210> SEQ ID NO 90
<211> LENGTH: 83
<212> TYPE: DNA
<213> ORGANISM: Artificial
<220> FEATURE:
<223> OTHER INFORMATION: an artificially synthesized sequence

<400> SEQUENCE: 90
gcgcggccgc gatgaacttt caccctaagt ttttcttact acggtcacac gtcttcaggt        60
tgcatgttca tggagtagtt tag                                                83

<210> SEQ ID NO 91
<211> LENGTH: 27
<212> TYPE: DNA
<213> ORGANISM: Artificial
<220> FEATURE:
<223> OTHER INFORMATION: an artificially synthesized sequence

<400> SEQUENCE: 91
ccaccatggg ctccgtgtcc aaccagc                                            27

<210> SEQ ID NO 92
<211> LENGTH: 23
<212> TYPE: DNA
<213> ORGANISM: Artificial
<220> FEATURE:
<223> OTHER INFORMATION: an artificially synthesized sequence

<400> SEQUENCE: 92
gtcaattctg tgcctccggg agc                                                23

```
<210> SEQ ID NO 93
<211> LENGTH: 38
<212> TYPE: DNA
<213> ORGANISM: Artificial
<220> FEATURE:
<223> OTHER INFORMATION: an artificially synthesized sequence

<400> SEQUENCE: 93
gcgcggccgc accaccatgg gctccgtgtc caaccagc                              38

<210> SEQ ID NO 94
<211> LENGTH: 80
<212> TYPE: DNA
<213> ORGANISM: Artificial
<220> FEATURE:
<223> OTHER INFORMATION: an artificially synthesized sequence

<400> SEQUENCE: 94
gcgcggccgc gatgaacttt caccctaagt ttttcttact acggtcaatt ctgtgcctcc      60
gggagcaggg tagggctgtg                                                  80
```